US011155871B2

(12) United States Patent
Gruen et al.

(10) Patent No.: US 11,155,871 B2
(45) Date of Patent: Oct. 26, 2021

(54) ASSESSING RISK OF READING AND LANGUAGE IMPAIRMENT

(71) Applicant: Yale University, New Haven, CT (US)

(72) Inventors: Jeffrey R. Gruen, Hamden, CT (US); Natalie R. Powers, Bar Harbor, ME (US)

(73) Assignee: Yale University, New Haven, CT (US)

( * ) Notice: Subject to any disclaimer, the term of this patent is extended or adjusted under 35 U.S.C. 154(b) by 640 days.

(21) Appl. No.: 14/441,076

(22) PCT Filed: Nov. 7, 2013

(86) PCT No.: PCT/US2013/069015
§ 371 (c)(1),
(2) Date: May 6, 2015

(87) PCT Pub. No.: WO2014/074755
PCT Pub. Date: May 15, 2014

(65) Prior Publication Data
US 2015/0299792 A1 Oct. 22, 2015
US 2017/0152558 A9 Jun. 1, 2017

Related U.S. Application Data

(60) Provisional application No. 61/723,774, filed on Nov. 7, 2012.

(51) Int. Cl.
*C12Q 1/68* (2018.01)
*C12Q 1/6883* (2018.01)
*G09B 19/00* (2006.01)

(52) U.S. Cl.
CPC ........... *C12Q 1/6883* (2013.01); *G09B 19/00* (2013.01); *C12Q 2600/118* (2013.01); *C12Q 2600/156* (2013.01); *C12Q 2600/16* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 5,525,467 A | 6/1996 | Anand | |
| 6,060,240 A | 5/2000 | Kamb et al. | |
| 6,323,009 B1 | 11/2001 | Lasken et al. | |
| 7,355,022 B2 | 4/2008 | Kere et al. | |
| 2003/0118998 A1 | 6/2003 | Dean et al. | |
| 2008/0318217 A1* | 12/2008 | Gruen | C12Q 1/6883 435/6.11 |
| 2014/0051076 A1 | 2/2014 | Gruen et al. | |

FOREIGN PATENT DOCUMENTS

WO    WO 2006/032021 A2    3/2006

OTHER PUBLICATIONS

Cope et al; Am J. Hum. Genet. vol. 76, pp. 581-591; 2005.*
Pushkarev et al; Nature Biotechnology, vol. 27, pp. 847-850 and pp. 1-2 of Online methods.*
U.S. Appl. No. 13/967,291, filed Aug. 14, 2013, Published, 2014-0051076.
PCT/US2005/033114, Oct. 12, 2006, International Search Report and Written Opinion.
PCT/US2005/033114, Mar. 20, 2007, International Preliminary Report on Patentability.
PCT/US2013/069015, Feb. 20, 2014, International Search Report and Written Opinion.
PCT/US2013/069015, May 21, 2015, International Preliminary Report on Patentability.
EP 13 792 839.6, Feb. 9, 2017, European Office Action.
European Office Action for Application No. EP 13 792 839.6, dated Feb. 9, 2017.
Ahern, Biochemical, reagents kits offer scientists good return on investment. The Scientist. 1995; 9(15):20-28.
Ahn et al., Peaks of linkage are localized by a BAC/PAC contig of the 6p reading disability locus. Genomics. Nov. 2001;78(1-2):19-29.
Beaver et al., Association between the A1 allele of the DRD2 gene and reduced verbal abilities in adolescence and early adulthood. J Neural Transm (Vienna). Jul. 2010;117(7):827-30. doi: 10.1007/s00702-010-0421-8. Epub Jun. 9, 2010.
Benson et al., GenBank. Nucleic Acids Res. Jan. 2009;37(Database issue):D26-31. doi: 10.1093/nar/gkn723. Epub Oct. 21, 2008.
Brkanac et al., Evaluation of candidate genes for DYX1 and DYX2 in families with dyslexia. Am J Med Genet B Neuropsychiatr Genet. Jun. 5, 2007;144B(4):556-60.
Cardon et al., Quantitative trait locus for reading disability on chromosome 6. Science. Oct. 14, 1994;266(5183):276-9. Erratum in: Science. Jun. 16, 1995;268(5217):1553.
Cope et al., Variants in the DYX2 locus are associated with altered brain activation in reading-related brain regions in subjects with reading disability. Neuroimage. Oct. 15, 2012;63(1):148-56. doi: 10.1016/j.neuroimage.2012.06.037. Epub Jun. 27, 2012.
Cope et al., Strong evidence that KIAA0319 on chromosome 6p is a susceptibility gene for developmental dyslexia. Am J Hum Genet. Apr. 2005;76(4):581-91. Epub Feb. 16, 2005.
Couto et al., Association of reading disabilities with regions marked by acetylated H3 histones in KIAA0319. Am J Med Genet B Neuropsychiatr Genet. Mar. 5, 2010;153B(2):447-62. doi: 10.1002/ajmg.b.30999.
De Backer et al., Genomic profiling of the response of Candida albicans to itraconazole treatment using a DNA microarray. Antimicrob Agents Chemother. Jun. 2001;45(6):1660-70.

(Continued)

*Primary Examiner* — Jehanne S Sitton
(74) *Attorney, Agent, or Firm* — Wolf, Greenfield & Sacks, P.C.

(57) ABSTRACT

Described herein are the association BV677278 (READ1) with reading disability and language impairment, as well as the synergistic interaction of DCDC2 risk haplotypes or alleles with KIAA0319 risk allele.

21 Claims, 7 Drawing Sheets

Specification includes a Sequence Listing.

(56) References Cited

OTHER PUBLICATIONS

Deffenbacher et al., Refinement of the 6p21.3 quantitative trait locus influencing dyslexia: linkage and association analyses. Hum Genet. Jul. 2004;115(2):128-38. Epub May 11, 2004.

Dennis et al., A common variant associated with dyslexia reduces expression of the KIAA0319 gene. PLoS Genet. Mar. 2009;5(3):e1000436. doi: 10.1371/journal.pgen.1000436. Epub Mar. 27, 2009.

Eicher et al., Imaging-genetics in dyslexia: connecting risk genetic variants to brain neuroimaging and ultimately to reading impairments. Mol Genet Metab. Nov. 2013;110(3):201-12. doi: 10.1016/j.ymgme.2013.07.001. Epub Jul. 17, 2013. Review.

Eicher et al., Associations of prenatal nicotine exposure and the dopamine related genes ANKK1 and DRD2 to verbal language. PLoS One. May 15, 2013;8(5):e63762. doi:10.1371/journal.pone.0063762. Print 2013.

Eicher et al., Pediatric Imaging, Neurocognition, and Genetics Study. Genome-wide association study of shared components of reading disability and language impairment. Genes Brain Behav. Nov. 2013;12(8):792-801. doi: 10.1111/gbb.12085. Epub Oct. 9, 2013.

Elbert et al., Genetic variation in the KIAA0319 5' region as a possible contributor to dyslexia. Behav Genet. Jan. 2011;41(1):77-89. doi: 10.1007/s10519-010-9434-1. Epub Jan. 5, 2011.

Francks et al., A 77-kilobase region of chromosome 6p22.2 is associated with dyslexia in families from the United Kingdom and from the United States. Am J Hum Genet. Dec. 2004;75(6):1046-58. Epub Oct. 22, 2004.

Gayán et al., Quantitative-trait locus for specific language and reading deficits on chromosome 6p. Am J Hum Genet. Jan. 1999;64(1):157-64.

Genbank Submission; NIH/NCBI, Accession No. AB175156. Fuji et al., Mar. 26, 2004. 2 pages.

Genbank Submission; NIH/NCBI, Accession No. 1RY1_P. Halic et al., Dec. 27, 2012. 2 pages.

Genbank Submission; NIH/NCBI, Accession No. V00837. Deugau et al., Jul. 13, 1983. 2 pages.

Gibson et al., The Human Lexinome: genes of language and reading. J Comm. Disorders, 2009;41: 409-420.

Golding et al., ALSPAC Study Team. ALSPAC—the Avon Longitudinal Study of Parents and Children. I. Study methodology. Paediatr Perinat Epidemiol. Jan. 2001;15(1):74-87.

Graham et al., Decoding the genetics of speech and language. Curr Opin Neurobiol. Feb. 2013;23(1):43-51. doi: 10.1016/j.conb.2012.11.006. Epub Dec. 7, 2012. Review.

Han et al., Efficient association study design via power-optimized tag SNP selection. Ann Hum Genet. Nov. 2008;72(Pt 6):834-47. doi: 10.1111/j.1469-1809.2008.00469.x. Epub Aug. 13, 2008.

Harold et al., Further evidence that the KIAA0319 gene confers susceptibility to developmental dyslexia. Mol Psychiatry. Dec. 2006;11(12):1085-91, 1061. Epub Oct. 10, 2006.

Kaminen et al., A genome scan for developmental dyslexia confirms linkage to chromosome 2p11 and suggests a new locus on 7q32.J Med Genet. May 2003;40(5):340-5.

Kaplan et al., Evidence for linkage and association with reading disability on 6p21.3-22. Am J Hum Genet. May 2002;70(5):1287-98. Epub Apr. 10, 2002.

Kwok, High-throughput genotyping assay approaches. Pharmacogenomics. Feb. 2000;1(1):95-100. Review.

Landi et al., The COMT Val/Met polymorphism is associated with reading-related skills and consistent patterns of functional neural activation. Dev Sci. Jan. 2013;16(1):13-23. doi: 10.1111/j.1467-7687.2012.01180.x. Epub Oct. 3, 2012.

Lind et al., Dyslexia and DCDC2: normal variation in reading and spelling is associated with DCDC2 polymorphisms in an Australian population sample. Eur J Hum Genet. Jun. 2010;18(6):668-73. doi: 10.1038/ejhg.2009.237. Epub Jan. 13, 2010.

Livak et al., Oligonucleotides with fluorescent dyes at opposite ends provide a quenched probe system useful for detecting PCR product and nucleic acid hybridization. PCR Methods Appl. Jun. 1995;4(6):357-62.

Londin et al., A transcription map of the 6p22.3 reading disability locus identifying candidate genes. BMC Genomics. 4(25):1-8 (2003).

Luciano et al., A haplotype spanning KIAA0319 and TTRAP is associated with normal variation in reading and spelling ability. Biol Psychiatry. Oct. 1, 2007;62(7):811-7. Epub Jun. 27, 2007.

Ludwig et al., Investigation of the DCDC2 intron 2 deletion/compound short tandem repeat polymorphism in a large German dyslexia sample. Psychiatr Genet. Dec. 2008;18(6):310-2. doi: 10.1097/YPG.0b013e3283063a78.

Ludwig et al., Investigation of interaction between DCDC2 and KIAA0319 in a large German dyslexia sample. J Neural Transm (Vienna). Nov. 2008;115(11):1587-9. doi: 10.1007/s00702-008-0124-6. Epub Sep. 23, 2008.

Marino et al., DCDC2 genetic variants and susceptibility to developmental dyslexia. Psychiatr Genet. Feb. 2012;22(1):25-30. doi: 10.1097/YPG.0b013e32834acdb2.

Meng et al., Candidates for the 6p21.3-22 Reading Disability (DYX2) Gene. Abstract. Apr. 2004, pp. 580A.

Meng et al., DCDC2 is associated with reading disability and modulates neuronal development in the brain. Proc Natl Acad Sci U S A. Nov. 22, 2005;102(47):17053-8. Epub Nov. 8, 2005.

Meng et al., A dyslexia-associated variant in DCDC2 changes gene expression. Behav Genet. Jan. 2011;41(1):58-66. doi: 10.1007/s10519-010-9408-3. Epub Nov. 2, 2010.

Newbury et al., CMIP and ATP2C2 modulate phonological short-term memory in language impairment. Am J Hum Genet. Aug. 2009;85(2):264-72. doi: 10.1016/j.ajhg.2009.07.004. Epub Jul. 30, 2009.

Newbury et al., Investigation of dyslexia and SLI risk variants in reading- and language-impaired subjects. Behav Genet. Jan. 2011;41(1):90-104. doi: 10.1007/s10519-010-9424-3. Epub Dec. 17, 2010.

Nordfors et al., Large-scale genotyping of single nucleotide polymorphisms by Pyrosequencingtrade mark and validation against the 5'nuclease (Taqman((R))) assay. Hum Mutat. Apr. 2002;19(4):395-401.

Nunes et al., Learning morphological and phonological spelling rules: an intervention study. Scientific Studies of Reading. 2003;7(3):289-307. doi: 10.1207/s1532799xssr0703_6.

Paracchini et al., The chromosome 6p22 haplotype associated with dyslexia reduces the expression of KIAA0319, a novel gene involved in neuronal migration. Hum Mol Genet. May 15, 2006;15(10):1659-66. Epub Apr. 6, 2006.

Paracchini et al., Association of the KIAA0319 dyslexia susceptibility gene with reading skills in the general population. Am J Psychiatry. Dec. 2008;165(12):1576-84. doi: 10.1176/appi.ajp.2008.07121872. Epub Oct. 1, 2008.

Peter et al., Replication of CNTNAP2 association with nonword repetition and support for FOXP2 association with timed reading and motor activities in a dyslexia family sample. J Neurodev Disord. Mar. 2011;3(1):39-49. doi: 10.1007/s11689-010-9065-0. Epub Nov. 9, 2010.

Pixel et al., Genetic variants of FOXP2 and KIAA0319/TTRAP/THEM2 locus are associated with altered brain activation in distinct language-related regions. J Neurosci. Jan. 18, 2012;32(3):817-25. doi:10.1523/JNEUROSCI.5996-10.2012.

Plomin et al., A functional polymorphism in the succinate-semialdehyde dehydrogenase (aldehyde dehydrogenase 5 family, member A1) gene is associated with cognitive ability. Mol Psychiatry. Jun. 2004;9(6):582-6.

Powers et al., Alleles of a polymorphic ETV6 binding site in DCDC2 confer risk of reading and language impairment. Am J Hum Genet. Jul. 11, 2013;93(1):19-28. doi: 10.1016/j.ajhg.2013.05.008. Epub Jun. 6, 2013.

Scerri et al., DCDC2, KIAA0319 and CMIP are associated with reading-related traits. Biol Psychiatry. Aug. 1, 2011;70(3):237-45. doi: 10.1016/j.biopsych.2011.02.005. Epub Mar. 31, 2011.

(56) References Cited

OTHER PUBLICATIONS

Schumacher et al., Independent Evidence for the VMP/DCDC2/KAAG1 Gene Locus on Chromosomal Region 6P22 as Susceptibility Factor for Dyslexia. Abstract. Sep. 2005, pp. 114.

Schumacher et al., Strong genetic evidence of DCDC2 as a susceptibility gene for dyslexia. Am J Hum Genet. Jan. 2006;78(1):52-62. Epub Nov. 17, 2005.

Shaywitz, S.E., "Dyslexia," in Brain, Behavior, and Learning in Language and Reading Disorders. Challenges in Language and Literacy, M. Mody, E.R. Silliman, eds. Guilford Press, NY, 2008, 209-239.

Shaywitz, S.E., "Dyslexia," in Handbook of Child Language Disorders. Schwartz, R.G., ed. Psychology Press, London, 2008.

Shaywitz, S.E., et al., Management of dyslexia, its rationale, and underlying neurobiology. Pediatric Clinics of North America. 2007;54(3):609-23, viii.

Takagi et al., DNA measurements by using fluorescence correlation spectroscopy and two-color fluorescence cross correlation spectroscopy. Curr Pharm Biotechnol. Apr. 2004;5(2):199-204.

Trzaskowski et al., DNA evidence for strong genome-wide pleiotropy of cognitive and learning abilities. Behav Genet. Jul. 2013;43(4):267-73. doi: 10.1007/s10519-013-9594-x. Epub Apr. 23, 2013.

Turic et al., Linkage disequilibrium mapping provides further evidence of a gene for reading disability on chromosome 6p21.3-22. Mol Psychiatry. Feb. 2003;8(2):176-85.

Van Den Eynde et al., "A New Antigen Recognized by Cytolytic T Lymphocytes on a Human Kidney Tumor Results from Reverse Strand Transcription," J. Exp. Med 190(12):1793-1799 (1999).

Wilcke et al., The role of gene DCDC2 in German dyslexics. Ann Dyslexia. Jun. 2009;59(1):1-11. doi:10.1007/s11881-008-0020-7. Epub Feb. 24, 2009.

Wilcke et al., Imaging genetics of FOXP2 in dyslexia. Eur J Hum Genet. Feb. 2012;20(2):224-9. doi:10.1038/ejhg.2011.160. Epub Sep. 7, 2011.

Zhong et al., Meta-analysis of the association between DCDC2 polymorphisms and risk of dyslexia. Mol Neurobiol. Feb. 2013; 47(1):435-42. doi: 10.1007/s12035-012-8381-7. Epub Dec. 11, 2012.

Zou et al., Genetic variant in KIAA0319, but not in DYX1C1, is associated with risk of dyslexia: an integrated meta-analysis. Am J Med Genet B Neurophyschiatr Genet. Dec. 2012;159B(8):970-6. doi: 10.1002/ajmg.b.32102. Epub Oct. 12, 2012.

* cited by examiner

A.

| Unit # | Repeat unit 1 | Repeat unit 2 | Repeat unit 3 | Repeat unit 4 | Constant Region | Repeat unit 5 | Constant Region |
|---|---|---|---|---|---|---|---|
| Sequence | GAGAGGAAGGAAA | GGAA | GAAA | GGAA | GGAAAGAATGAA | GGAA | GGGA |
| Number Present | 1-2 | 4-10 | 0-2 | 0-2 | Constant | 3-4 | Constant |

B.

A.

B.

A.

B.

A.

B.

SEQUENCE LISTING

<160> NUMBER OF SEQ ID NOS: 68

<210> SEQ ID NO 1
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 1
tgtaaaacga cggccagttg ttgaatccca gaccacaa         38

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
atcccgatga aatgaaaagg         20

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 3
tgtaaaacga cggccagt         18

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
agcctgccta ccacagagaa         20

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
ggaacaacct cacagaaatg g         21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
tgaaaccccg tctctactga a         21

<210> SEQ ID NO 7
<211> LENGTH: 47
<212> TYPE: DNA
<213> ORGANISM: Artificial Sequence

```
<220> FEATURE:
<223> OTHER INFORMATION: Synthetic oligonucleotide

<400> SEQUENCE: 7
ttgagaggaa ggaaaggaag gatccctgag aggaaggaaa ggaagga          47

<210> SEQ ID NO 8
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 8
aatccttcct ttccttcctc tcagggatcc ttcctttcct tcctctc          47

<210> SEQ ID NO 9
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 9
ttgagagaga gagagagaga gatccctgag agagagagag agagaga          47

<210> SEQ ID NO 10
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 10
aatctctctc tctctctctc tcagggatct ctctctctct ctctctc          47

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
tcatgcaaag ttccaaaacc                                         20

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12
gatttcctcc ctcccttcc                                          19

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 13
gccctaggca ccagggtgtg a                                       21
```

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
acagggtgct cctcaggggc                                         20

<210> SEQ ID NO 15
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 15
gagaggaagg aaagagagga aggaaa                                  26

<210> SEQ ID NO 16
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 16
gagaggaagg aaa                                                13

<210> SEQ ID NO 17
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 17
gagaggaagg aaagagagga agaaaa                                  26

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 18
gagaggaagg aaagagagga aggaa                                   25

<210> SEQ ID NO 19
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 19
ggaaggaagg aaggaaggaa ggaaggaa                                28

<210> SEQ ID NO 20
<211> LENGTH: 36
<212> TYPE: DNA
<213> ORGANISM: Artificial Sequence
<220> FEATURE:
<223> OTHER INFORMATION: Synthetic oligonucleotide

```
<400> SEQUENCE: 20
ggaaggaagg aaggaaggaa ggaaggaagg aaggaa                    36

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21
ggaaggaagg aaggaaggaa ggaa                                 24

<210> SEQ ID NO 22
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 22
ggaaggaagg aaggaaggaa ggaaggaagg aa                        32

<210> SEQ ID NO 23
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 23
ggaaggaagg aaggaa                                          16

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
ggaaggaagg aaggaaggaa                                      20

<210> SEQ ID NO 25
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 25
ggaaggaagg aaggaaggaa ggaaggaagg aaggaaggaa                40

<210> SEQ ID NO 26
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 26
ggaaggaagg aaggaaggaa ggaaggaagg aaggaaggaa ggaa           44

<210> SEQ ID NO 27
```

-continued

<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 27
ggaaggaagg aaggaaggaa gggaggaa                                        28

<210> SEQ ID NO 28
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 28
ggaaagaatg aa                                                        12

<210> SEQ ID NO 29
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 29
ggaaggaagg aa                                                        12

<210> SEQ ID NO 30
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 30
ggaagaaagg aaggaa                                                    16

<210> SEQ ID NO 31
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 31
gagaggaagg aaagagagga aggaaaggaa ggaaggaagg aaggaaggaa ggaagaaagg     60
aaggaaggaa agaatgaagg aaggaaggaa ggaagggagg ga                       102

<210> SEQ ID NO 32
<211> LENGTH: 85
<212> TYPE: DNA
<213> ORGANISM: Artificial Sequence
<220> FEATURE:
<223> OTHER INFORMATION: Synthetic oligonucleotide

<400> SEQUENCE: 32
gagaggaagg aaaggaagga aggaaggaag gaaggaagga aggaaggaag gaaagaatga     60
aggaaggaag gaaggaaggg aggga                                          85

<210> SEQ ID NO 33
<211> LENGTH: 85
<212> TYPE: DNA
<213> ORGANISM: Artificial Sequence

```
<220> FEATURE:
<223> OTHER INFORMATION: Synthetic oligonucleotide

<400> SEQUENCE: 33
gagaggaagg aaaggaagga aggaaggaag gaaggaagaa aggaaggaag gaaagaatga      60
aggaaggaag gaaggaaggg aggga                                            85

<210> SEQ ID NO 34
<211> LENGTH: 98
<212> TYPE: DNA
<213> ORGANISM: Artificial Sequence
<220> FEATURE:
<223> OTHER INFORMATION: Synthetic oligonucleotide

<400> SEQUENCE: 34
gagaggaagg aaagagagga aggaaaggaa ggaaggaagg aaggaaggaa gaaaggaagg      60
aaggaaagaa tgaaggaagg aaggaaggaa gggaggga                              98

<210> SEQ ID NO 35
<211> LENGTH: 106
<212> TYPE: DNA
<213> ORGANISM: Artificial Sequence
<220> FEATURE:
<223> OTHER INFORMATION: Synthetic oligonucleotide

<400> SEQUENCE: 35
gagaggaagg aaagagagga aggaaaggaa ggaaggaagg aaggaaggaa ggaaggaaga      60
aaggaaggaa ggaaagaatg aaggaaggaa ggaaggaagg gaggga                    106

<210> SEQ ID NO 36
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 36
gagaggaagg aaagagagga aggaaaggaa ggaaggaagg aaggaaggaa ggaaggaaga      60
aaggaaggaa ggaaagaatg aaggaaggaa ggaagggagg ga                        102

<210> SEQ ID NO 37
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 37
gagaggaagg aaagagagga aggaaaggaa ggaaggaagg aaggaaggaa ggaaggaaga      60
aaggaaggaa agaatgaagg aaggaaggaa ggaagggagg ga                        102

<210> SEQ ID NO 38
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 38
gagaggaagg aaagagagga aggaaaggaa ggaaggaagg aaggaaggaa ggaaggaaag      60
aatgaaggaa ggaaggaagg aagggaggga                                       90
```

<210> SEQ ID NO 39
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 39
gagaggaagg aaaggaagga aggaaggaag gaaggaagga agaaaggaag gaaggaaaga    60
atgaaggaag gaaggaagga agggaggga                                     89

<210> SEQ ID NO 40
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 40
gagaggaagg aaagagagga aggaaaggaa ggaaggaagg aagaaaggaa ggaaggaaag    60
aatgaaggaa ggaaggaagg aagggaggga                                    90

<210> SEQ ID NO 41
<211> LENGTH: 98
<212> TYPE: DNA
<213> ORGANISM: Artificial Sequence
<220> FEATURE:
<223> OTHER INFORMATION: Synthetic oligonucleotide

<400> SEQUENCE: 41
gagaggaagg aaagagagga aggaaaggaa ggaaggaagg aaggaaggaa ggaagaaagg    60
aaggaaggaa agaatgaagg aaggaaggaa gggaggga                           98

<210> SEQ ID NO 42
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 42
gagaggaagg aaaggaagga aggaaggaag gaaggaagga aggaagaaag gaaggaagga    60
aagaatgaag gaaggaagga agggaggga                                     89

<210> SEQ ID NO 43
<211> LENGTH: 106
<212> TYPE: DNA
<213> ORGANISM: Artificial Sequence
<220> FEATURE:
<223> OTHER INFORMATION: Synthetic oligonucleotide

<400> SEQUENCE: 43
gagaggaagg aaagagagga aggaaaggaa ggaaggaagg aaggaaggaa ggaaggaagg    60
aagaaaggaa ggaaggaaag aatgaaggaa ggaaggaagg gaggga                  106

<210> SEQ ID NO 44
<211> LENGTH: 110
<212> TYPE: DNA
<213> ORGANISM: Artificial Sequence
<220> FEATURE:
<223> OTHER INFORMATION: Synthetic oligonucleotide

<400> SEQUENCE: 44

```
gagaggaagg aaagagagga aggaaaggaa ggaaggaagg aaggaaggaa ggaaggaagg      60
aagaaaggaa ggaaggaaag aatgaaggaa ggaaggaagg aagggaggga                110
```

<210> SEQ ID NO 45
<211> LENGTH: 98
<212> TYPE: DNA
<213> ORGANISM: Artificial Sequence
<220> FEATURE:
<223> OTHER INFORMATION: Synthetic oligonucleotide

<400> SEQUENCE: 45

```
gagaggaagg aaagagagga aggaaaggaa ggaaggaagg aaggaagaaa gaaaggaagg      60
aaggaaagaa tgaaggaagg aaggaaggaa gggaggga                             98
```

<210> SEQ ID NO 46
<211> LENGTH: 94
<212> TYPE: DNA
<213> ORGANISM: Artificial Sequence
<220> FEATURE:
<223> OTHER INFORMATION: Synthetic oligonucleotide

<400> SEQUENCE: 46

```
gagaggaagg aaagagagga aggaaaggaa ggaaggaagg aaggaagaaa ggaaggaagg      60
aaagaatgaa ggaaggaagg aaggaaggga ggga                                 94
```

<210> SEQ ID NO 47
<211> LENGTH: 94
<212> TYPE: DNA
<213> ORGANISM: Artificial Sequence
<220> FEATURE:
<223> OTHER INFORMATION: Synthetic oligonucleotide

<400> SEQUENCE: 47

```
gagaggaagg aaagagagga aggaaaggaa ggaaggaagg aagaaagaaa ggaaggaagg      60
aaagaatgaa ggaaggaagg aaggaaggga ggga                                 94
```

<210> SEQ ID NO 48
<211> LENGTH: 106
<212> TYPE: DNA
<213> ORGANISM: Artificial Sequence
<220> FEATURE:
<223> OTHER INFORMATION: Synthetic oligonucleotide

<400> SEQUENCE: 48

```
gagaggaagg aaagagagga aggaaaggaa ggaaggaagg aaggaaggaa ggaagaaaga      60
aaggaaggaa ggaaagaatg aaggaaggaa ggaaggaagg gaggga                    106
```

<210> SEQ ID NO 49
<211> LENGTH: 98
<212> TYPE: DNA
<213> ORGANISM: Artificial Sequence
<220> FEATURE:
<223> OTHER INFORMATION: Synthetic oligonucleotide

<400> SEQUENCE: 49

```
gagaggaagg aaagagagga aggaaaggaa ggaaggaagg aaggaaggaa ggaaggaagg      60
aaggaaagaa tgaaggaagg aaggaaggaa gggaggga                             98
```

<210> SEQ ID NO 50
<211> LENGTH: 114
<212> TYPE: DNA

```
<213> ORGANISM: Artificial Sequence
<220> FEATURE:
<223> OTHER INFORMATION: Synthetic oligonucleotide

<400> SEQUENCE: 50
gagaggaagg aaagagagga aggaaaggaa ggaaggaagg aaggaaggaa ggaaggaagg      60
aaggaagaaa ggaaggaagg aaagaatgaa ggaaggaagg aaggaaggga ggga           114

<210> SEQ ID NO 51
<211> LENGTH: 94
<212> TYPE: DNA
<213> ORGANISM: Artificial Sequence
<220> FEATURE:
<223> OTHER INFORMATION: Synthetic oligonucleotide

<400> SEQUENCE: 51
gagaggaagg aaagagagga aggaaaggaa ggaaggaagg aaggaaggaa gaaaggaagg      60
aaggaaagaa tgaaggaagg aaggaaggga ggga                                 94

<210> SEQ ID NO 52
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 52
gagaggaagg aaagagagga aggaaaggaa ggaaggaagg aaggaaggaa ggaaggaagg      60
aaggaaggaa agaatgaagg aaggaaggaa ggaagggagg ga                        102

<210> SEQ ID NO 53
<211> LENGTH: 106
<212> TYPE: DNA
<213> ORGANISM: Artificial Sequence
<220> FEATURE:
<223> OTHER INFORMATION: Synthetic oligonucleotide

<400> SEQUENCE: 53
gagaggaagg aaagagagga aggaaaggaa ggaaggaagg aaggaaggaa ggaaggaagg      60
aaggaaggaa ggaaagaatg aaggaaggaa ggaaggaagg gaggga                    106

<210> SEQ ID NO 54
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 54
gagaggaagg aaagagagga aggaaaggaa ggaaggaagg aaggaaggaa gaaagaaagg      60
aaggaaggaa agaatgaagg aaggaaggaa ggaagggagg ga                        102

<210> SEQ ID NO 55
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 55
gagaggaagg aaaggaagga aggaaggaag gaaggaagga aggaagaaag gaaggaagga      60
aagaatgaag gaaggaagga aggaagggag gga                                  93
```

```
<210> SEQ ID NO 56
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 56
gagaggaagg aaagagagga aggaaaggaa ggaaggaagg aaggaagaaa ggaaggaagg      60
aaagaatgaa ggaaggaagg aagggaggga                                       90

<210> SEQ ID NO 57
<211> LENGTH: 81
<212> TYPE: DNA
<213> ORGANISM: Artificial Sequence
<220> FEATURE:
<223> OTHER INFORMATION: Synthetic oligonucleotide

<400> SEQUENCE: 57
gagaggaagg aaaggaagga aggaaggaag gaagaaagga aggaaggaaa gaatgaagga      60
aggaaggaag gaagggaggg a                                                81

<210> SEQ ID NO 58
<211> LENGTH: 106
<212> TYPE: DNA
<213> ORGANISM: Artificial Sequence
<220> FEATURE:
<223> OTHER INFORMATION: Synthetic oligonucleotide

<400> SEQUENCE: 58
gagaggaagg aaagagagga aggaaaggaa ggaaggaagg aaggaaggaa ggaagaaagg      60
aaggaaggaa agaatgaagg aaggaaggaa ggaaggaagg gaggga                    106

<210> SEQ ID NO 59
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 59
gagaggaagg aaagagagga aggaaaggaa ggaaggaagg aaggaaggga ggaagaaagg      60
aaggaaggaa agaatgaagg aaggaaggaa ggaagggagg ga                        102

<210> SEQ ID NO 60
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 60
gagaggaagg aaagagagga aggaaaggaa ggaaggaagg aaggaagaaa ggaaggaagg      60
aaggaaggaa agaatgaagg aaggaaggaa ggaagggagg ga                        102

<210> SEQ ID NO 61
<211> LENGTH: 102
<212> TYPE: DNA
<213> ORGANISM: Artificial Sequence
<220> FEATURE:
<223> OTHER INFORMATION: Synthetic oligonucleotide
```

```
<400> SEQUENCE: 61
gagaggaagg aaagagagga aggaaaggaa ggaaggaagg aaggaaggaa ggaagaaagg      60
aagggaggaa agaatgaagg aaggaaggaa ggaagggagg ga                       102

<210> SEQ ID NO 62
<211> LENGTH: 94
<212> TYPE: DNA
<213> ORGANISM: Artificial Sequence
<220> FEATURE:
<223> OTHER INFORMATION: Synthetic oligonucleotide

<400> SEQUENCE: 62
gagaggaagg aaagagagga aggaaaggaa ggaaggaagg aaggaaggaa ggaaggaagg      60
aaagaatgaa ggaaggaagg aaggaaggga ggga                                 94

<210> SEQ ID NO 63
<211> LENGTH: 82
<212> TYPE: DNA
<213> ORGANISM: Artificial Sequence
<220> FEATURE:
<223> OTHER INFORMATION: Synthetic oligonucleotide

<400> SEQUENCE: 63
gagaggaagg aaagagagga aggaaaggaa ggaaggaagg aaggaaggaa ggaaagaatg      60
aaggaaggaa ggaagggagg ga                                              82

<210> SEQ ID NO 64
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 64
gagaggaagg aaagagagga aggaaaggaa ggaaggaagg aaggaaggaa ggaagaaaga      60
aaggaaggaa ggaaagaatg aaggaaggaa ggaagggagg ga                       102

<210> SEQ ID NO 65
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 65
gagaggaagg aaagagagga agaaaaggaa ggaaggaagg aaggaaggaa ggaagaaagg      60
aaggaaggaa agaatgaagg aaggaaggaa ggaagggagg ga                       102

<210> SEQ ID NO 66
<211> LENGTH: 109
<212> TYPE: DNA
<213> ORGANISM: Artificial Sequence
<220> FEATURE:
<223> OTHER INFORMATION: Synthetic oligonucleotide

<400> SEQUENCE: 66
gagaggaagg aaagagagga aggaaggaag gaaggaagga aggaaggaag gaaggaagga      60
agaaaggaag gaaggaaaga atgaaggaag gaaggaagga agggaggga              109

<210> SEQ ID NO 67
<211> LENGTH: 98
```

-continued

```
<212> TYPE: DNA
<213> ORGANISM: Artificial Sequence
<220> FEATURE:
<223> OTHER INFORMATION: Synthetic oligonucleotide

<400> SEQUENCE: 67
gagaggaagg aaagagagga aggaaaggaa ggaaggaagg aaggaaggaa gaaaggaagg      60
aaggaaagaa tgaaggaaga aaggaaggaa gggaggga                              98

<210> SEQ ID NO 68
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 68
gagaggaagg aaaggaagga aggaaggaag gaaggaagga aggaaggaag gaaggaaaga      60
atgaaggaag gaaggaagga agggaggga                                        89
```

ASSESSING RISK OF READING AND LANGUAGE IMPAIRMENT

RELATED APPLICATIONS

This application is a national stage filing under 35 U.S.C. § 371 of international application PCT/US2013/069015, filed Nov. 7, 2013, which claims the benefit of U.S. Provisional Application No. 61/723,774, filed Nov. 7, 2012. The teachings of the referenced application are incorporated by reference herein in their entirety.

FEDERAL FUNDING

This invention was made with government support under R01NS043530 awarded by the National Institutes of Health. The government has certain rights in the invention.

BACKGROUND

Specific learning disabilities (LDs) are disorders characterized by unexpected difficulty with a specific mode of learning, despite adequate IQ and educational opportunity. LDs can involve reading, math, writing, and speech skills, among others, but the most common involve language. The National Institute of Child Health and Development (NICHD) estimates 15-20% of Americans have a language-based LD, of which reading disability (RD) afflicts the majority (1). RD, also known as dyslexia, is a specific impairment in processing written language (2). Another LD, language impairment (LI), is characterized by difficulty processing and expressing spoken language (3). These LDs are frequently comorbid; children with LI have increased risk of developing RD (3). Because reading and language skills are fundamental to academic success, affected individuals are at risk for adverse psychological outcomes, as well as limited educational and occupational prospects (2). Additionally, the prevalence of these LDs makes the cost of remediation burdensome to the educational system (4). Intervention is more effective the earlier it is administered (2), making early detection of high-risk individuals an attractive prospect.

SUMMARY

As described herein, two haplotypes, both in the same six-marker haplotype block in the reading disability (RD) risk gene DCDC2, are associated, respectively, with reading disability and language impairment (LI). Each of the haplotypes is in very strong linkage disequilibrium with an allele of BV677278 (also known as READ1), which is a polymorphic compound STR associated with reading disability and capable of modulating expression from the DCDC2 promoter. BV677278 (READ1) has been shown to specifically bind ETV6, a potent transcriptional regulator and proto-oncogene, in vivo. BV677278 binds the brain-expressed nuclear protein with very high specificity and is capable of modulating reporter gene expression from the DCDC2 promoter in an allele-specific manner. Activation patterns in reading-related areas of the brain, as measured by functional magnetic resonance imaging, are influenced by BV677278 alleles. Work described herein shows that BV677278 is associated with both reading and language, and that at least two BV677278 alleles have a deleterious effect on reading and language. Allele 5 is important for dyslexia (RD) and allele 6 is important for language impairment. BV677278 has been renamed and is also referred to herein as READ1, which stands for "regulatory element associated with dyslexia 1." The two terms are used interchangeably.

As also described herein, the DCDC2 risk haplotypes or alleles interact with a KIAA0319 risk haplotype in a synergistic manner. The synergy between the BV677278 (READ1) alleles or the DCDC2 risk haplotypes and the KIAA0319 haplotypes in decreasing performance in phoneme deletion (very important to reading), spelling, and total IQ and performance IQ, has not previously been described. Together, the effect is 3-fold to 8-fold greater than if the deleterious version of either risk allele or haplotype is present.

In particular, described herein is a six-marker haplotype block within DCDC2, of which two haplotypes (CGCGAG and GACGAG) associated with very poor performance on a phoneme deletion task and composite language measure, respectively. The two haplotypes show strong association with their respective phenotypes: CGCGAG with RD and GACGAG with LI. Carriers of the CGCGAG haplotype, on average, showed significantly poorer performance on eight reading-related measures, compared to non-carriers, and carriers of the GACGAG haplotype showed significantly lower average performance on the WOLD/WR composite language measure.

Further described herein are methods of identifying or aiding in identifying an individual who is at risk of developing at least one (a, one or more) learning disability (LD), in which a sample obtained from the individual is assayed for the presence of at least one (a, one or more) haplotype in the DYX2 locus (chromosome 6p; 6p22) that is associated with susceptibility for developing at least one (a, one or more) LD in humans. The presence of at least one haplotype that is associated with susceptibility for developing at least one (a, one or more) LD in humans in the DYX2 locus indicates that the individual is at risk for developing at least one (a, one or more) LD. In some embodiments, the at least one LD is reading disability (RD) or language impairment (LI). The at least one haplotype can be located in the DCDC2 gene within the DYX2 locus or in the KIAA0319 gene within the DYX2 locus. Alternatively, a sample is assayed (analyzed) for the presence of a haplotype located in the DCDC2 gene within the DYX2 locus and the presence of a haplotype located in the KIAA0319 gene within the DYX2 locus. The at least one haplotype can comprise (a) CGCGAG, GACGAG or both in a DCDC2 gene within the DYX2 locus; (b) one or more single nucleotide polymorphisms (SNPs) associated with a variant KIAA0319, such as rs4504469, rs2038137, or rs2143340 or any combination of two or three of rs4504469, rs2038137 and rs2143340; or (c) any combination of the haplotypes in (a) and (b). Also described herein are methods of treating an individual suspected or identified as having a LD. Treatment can include, for example, inhibiting ETV6 in the individual, and/or providing services designed to address or remedy certain aspects associated with a LD, such as RD or LI, such as providing intervention, including services and materials, including but not limited to using special teaching techniques; making classroom modifications, such as providing extra time to complete tasks and taped tests to permit the individual to hear, rather than read the tests; using books on tape; using word-processing programs with spell-check features; helping the individual learn through multisensory experiences; teaching coping tools; and providing services to strengthen the individual's ability to recognize and pronounce words.

Described herein is a method of determining if a sample obtained from an individual comprises nucleic acid which comprises a haplotype associated with susceptibility for developing a learning disability (LD) in humans, comprising assaying a sample that comprises nucleic acid from the individual for the presence in the DYX2 locus of at least one of the following markers: (a) CGCGAG in a DCDC2 gene; (b) CACGAG in a DCDC2 gene; (c) both CGCGAG and CACGAG in a DCDC2 gene; (d) rs4504469 in a KIAA0319 gene; (e) rs2038137 in a KIAA0319 gene; (f) rs2143340 in a KIAA0319 gene; (g) any combination of two or three of rs4504469, rs2038137 and rs2143340 in a KIAA0319 gene; and (h) any combination of CGCGAG in a DCDC2 gene; CACGAG in a DCDC2 gene; both CGCGAG and CACGAG in a DCDC2 gene; rs4504469 in a KIAA0319 gene; rs2038137 in a KIAA03109 gene; rs2143340 in a KIAA0319 gene; and any combination of two or three of rs4504469, rs2038137 and rs2143340 in a KIAA0319 gene, wherein if the sample comprises at least one of (a)-(h), the sample comprises a haplotype associated with susceptibility for developing a learning disability in humans. In one embodiment, the sample is assayed for at least one marker of (a), (b) and (c) and at least one marker of (d), (e), (f) and (g). In various embodiments, the sample is assayed (analyzed) for two or more markers of (a), (b) and (c) and two or more markers of (d), (e), (f) and (g); only markers of (a), (b) and (c); only markers of (d), (e), (f) and (g); or any combination of the markers of (a)-(h). The LD can be RD or LI or both RD and LI. Any sample that contains nucleic acid (e.g., genomic DNA; RNA) that can be analyzed for a haplotype of interest can be assayed; methods for analyzing nucleic acids are well known in the art and also described herein. They include, but are not limited to, hybridization-mediated methods, and sequencing. The sample can be, for example, blood, cells, or tissue. Alternatively, genomic DNA can be sequenced and the presence or absence of a haplotype associated with susceptibility for developing a learning disability (LD) in humans determined. In one embodiment, the method further comprises assaying the sample for allele 5 of DCDC2 gene, as presented herein (e.g., SEQ ID NO:35); allele 6 of DCDC2 gene, as presented herein (e.g., SEQ ID NO:36) or both.

Another embodiment is a method of assaying a sample for a marker of a haplotype associated with susceptibility for developing a learning disability (LD) in humans, comprising: (a) obtaining a sample comprising nucleic acid from an individual; and (b) determining if the sample comprises at least one of the following: (i) CGCGAG in a DCDC2 gene in the DYX2 locus; (ii) CACGAG in a DCDC2 gene in the DYX2 locus; (iii) both CGCGAG and CACGAG in a DCDC2 gene in the DYX2 locus; (iv) rs4504469 in a KIAA0319 gene in the DYX2 locus; (v) rs2038137 in a KIAA0319 gene in the DYX2 locus; (vi) rs2143340 in a KIAA0319 gene in the DYX2 locus; (vii) any combination of two or three of rs4504469, rs2038137 and rs2143340 in a KIAA0319 gene in the DYX2 locus; and (viii) any combination of CGCGAG in a DCDC2 gene; CACGAG in a DCDC2 gene in the DYX2 locus; both CGCGAG and CACGAG in a DCDC2 gene in the DYX2 locus; rs4504469 in a KIAA0319 gene in the DYX2 locus; rs2038137 in a KIAA03109 gene in the DYX2 locus; rs2143340 in a KIAA0319 gene in the DYX2 locus; and any combination of two or three of rs4504469, rs2038137 and rs2143340 in a KIAA0319 gene in the DYX2 locus, wherein if the sample comprises at least one marker of (i)-(vii), the sample comprises a haplotype associated with susceptibility for developing a learning disability in humans. In one embodiment, the sample is assayed for at least one marker of (i), (ii) and (iii) and at least one marker of (iv), (v), (vi) and (vii). The LD is reading disability (RD) or language impairment (LI) or both RD and LI. Any sample that contains nucleic acid (e.g., genomic DNA; RNA) that can be analyzed for a haplotype of interest can be assayed; methods for analyzing nucleic acids are well known in the art and also described herein. They include, but are not limited to, hybridization-mediated methods and sequencing. The sample can be, for example, blood, cells, or tissue. Alternatively, genomic DNA can be sequenced and the presence or absence of a haplotype associated with susceptibility for developing a learning disability (LD) in humans determined.

A further embodiment is a method of determining if a sample obtained from an individual comprises nucleic acid which comprises an allele associated with susceptibility for developing a learning disability (LD) in humans, comprising: assaying a sample that comprises nucleic acid from the individual for the presence of allele 5 of DCDC2 gene in the DYX2 locus (e.g., SEQ ID NO:35), allele 6 of DCDC2 gene in the DYX2 locus (e.g., SEQ ID NO:36), or both allele 5 of DCDC2 gene and allele 6 of DCDC2 gene, wherein if the sample comprises at least one of allele 5 and allele 6, the sample comprises an allele associated with susceptibility for developing a learning disability. The LD is reading disability (RD) or language impairment (LI) or both RD and LI. Any sample that contains nucleic acid (e.g., genomic DNA; RNA) that can be analyzed for a haplotype of interest can be assayed; methods for analyzing nucleic acids are well known in the art and also described herein. They include, but are not limited to, hybridization-mediated methods and sequencing. The sample can be, for example, blood, cells, or tissue. Alternatively, genomic DNA can be sequenced and the presence or absence of a haplotype associated with susceptibility for developing a learning disability (LD) in humans determined.

A further embodiment is a method of determining if a sample obtained from an individual comprises at least one marker associated with comorbid reading disability (RD) and language impairment (LI) in humans, comprising: (a) obtaining a sample that contains nucleic acid from the individual and (b) assaying the sample for (i) at least one marker in DCDC2 gene in the DYX2 locus for a haplotype associated with susceptibility for developing RD in humans and (ii) at least one marker in KIAA0319 gene in the DXY2 locus for a haplotype associated with susceptibility for developing LI in humans, wherein if the sample comprises a marker of (i) and a marker of (ii), the sample comprises at least one marker associated with comorbid RD and LI. The marker of (b)(i) and the marker of (b)(ii) can be the same marker or two different markers. In one embodiment, the at least one marker of (b)(i) is CGCGAG or GACGAG and the at least one marker of (b)(ii) is rs4504469; rs2038137; or rs2143340. In any of these embodiments, the method can further comprise assaying the sample for allele 5 of DCDC2 gene in the DYX2 locus, allele 6 of DCDC2 gene of DYX2 locus, or both allele 5 of DCDC2 gene in the DYX2 locus and allele 6 of DCDC2 gene in the DYX2 locus. In yet further embodiments, the at least one marker of (b)(i) and the at least one marker of (b)(ii) are selected from: rs12636438; rs1679255; rs9521789; rs1983931; rs9814232; rs7995158; rs6573225; rs4082518; rs442555; rs259521; rs16889556; rs1047782; rs1530680; rs12667130; rs6965855; rs985080; rs4726782; rs1718101; rs10487689; rs1918296; rs737533; rs4504469; rs2038137; rs2143340; rs9295626; rs7763790 rs6935076; rs2817201; rs10456309; rs4576240; rs17307478; rs9356939; rs7763790; rs6456621;

rs6456624; rs6935076; rs2038137; rs3756821; rs1883593; rs3212236; rs6456621; rs12193738; rs2817198; rs793845; rs2799373; rs793862; rs793834; rs2792682; rs807704; rs707864; and rs807694. Any sample that contains nucleic acid (e.g., genomic DNA; RNA) that can be analyzed for a haplotype of interest can be assayed; methods for analyzing nucleic acids are well known in the art and also described herein. They include, but are not limited to, hybridization-mediated methods, and sequencing. The sample can be, for example, blood, cells, or tissue. Alternatively, genomic DNA can be sequenced and the presence or absence of a marker associated with susceptibility for developing a learning disability (LD) in humans determined.

Another embodiment is a method of determining if a sample obtained from an individual comprises a marker associated with language impairment (LI) in humans, comprising assaying a sample obtained from the individual for at least one of the following markers: CACGAG in a DCDC2 gene in the DYX2 locus; rs793845; rs2799373; rs793862; rs793834; rs2792682; rs807704; rs707864; rs12193738; rs2817198; rs10456309; rs985080; rs1554690; rs2533096; rs6951437; rs344470; rs344468; rs807694; rs482700; rs7695228; rs1940309; rs505277; rs476739; rs867036; rs867035; rs2071674; rs7694946; rs4823324; and a marker for at least one of the following genes: NEK2; DLEC1; NARS; IL4I1; PKD2; ATF5; NUP62; SIGLEC11; ACAN; and PGD. Any sample that contains nucleic acid (e.g., genomic DNA; RNA) that can be analyzed for a haplotype of interest can be assayed; methods for analyzing nucleic acids are well known in the art and also described herein. They include, but are not limited to, hybridization-mediated methods and sequencing. The sample can be, for example, blood, cells, or tissue. Alternatively, genomic DNA can be sequenced and the presence or absence of a marker associated with susceptibility for developing LI in humans determined.

A further embodiment is a method of determining if a sample obtained from an individual comprises a marker associated with reading disability (RD) in humans, comprising assaying a sample obtained from the individual for at least one of the following markers: CGCGAG in a DCDC2 gene in the DYX2 locus; rs180950; rs2590673; rs892100; rs1792745; rs12546767; rs12634033; rs892270; rs10887149; rs10041417; rs6792971; rs4725745; rs12444778; rs1444186; rs2294691; rs10456309; rs1562422; and a marker for at least one of the following genes: MAP4; OR2L8; CRYBA4; OR2T8; KIAA1622; OR2AK2; DHX30; GEMIN6; C20orf10; and PPIF. Any sample that contains nucleic acid (e.g., genomic DNA; RNA) that can be analyzed for a haplotype of interest can be assayed; methods for analyzing nucleic acids are well known in the art and also described herein. They include, but are not limited to, hybridization-mediated methods and sequencing. The sample can be, for example, blood, cells, or tissue. Alternatively, genomic DNA can be sequenced and the presence or absence of a marker associated with susceptibility for developing RD in humans determined.

Another embodiment is a method of determining if nucleic acids (DNA, RNA) in an individual comprise markers of haplotypes that interact in a synergistic manner in resulting in a learning disorder (LD) in humans comprising: (a) obtaining a sample that comprises nucleic acids from an individual and (b) assaying the sample for at least one DCDC2 risk haplotype or DCDC2 risk allele and at least one KIAA0319 risk haplotype, wherein the at least one DCDC2 risk haplotype is CGCGAG or GACGAG, the at least one DCDC2 risk allele is allele 5 of DCDC2 gene in the DYX2 locus (SEQ ID NO:35) or allele 6 of DCDC2 gene in the DYX2 locus (SEQ ID NO:36) and the at least one KIAA0319 risk haplotype is a variant KIAA0319 haplotype comprising a snp which is rs4504469; rs2038137; or rs2143340 and wherein if the sample comprises at least one DCDC2 risk haplotype or at least one DCDC2 risk allele and at least one KIAA0319 risk haplotype, the nucleic acids comprise markers of haplotypes that interact in a synergistic manner in resulting in a LD in humans. Any sample that contains nucleic acid (e.g., genomic DNA; RNA) that can be analyzed for a haplotype of interest can be assayed; methods for analyzing nucleic acids are well known in the art and also described herein. They include, but are not limited to, hybridization-mediated methods and sequencing. The sample can be, for example, blood, cells, or tissue. Alternatively, genomic DNA can be sequenced and the presence or absence of markers that interact in a synergistic manner in resulting in LD in humans determined.

A further embodiment is a method of identifying or aiding in identifying an individual at risk for developing at least one learning disability (LD), comprising assaying a sample obtained from the individual for the presence in the DYX2 locus of at least one haplotype that is associated with susceptibility for developing a LD in humans, wherein the presence in the DYX2 locus of at least one haplotype that is associated with susceptibility for developing a LD in humans indicates that the individual is at risk for developing a LD. At least one LD is a reading disability or language impairment. The at least one haplotype is located in the DCDC2 gene within the DYX2 locus or in the KIAA0319 gene within the DYX2 locus. The at least one haplotype can comprise (a) CGCGAG or CACGAG in a DCDC2 gene within the DYX2 locus; or (b) rs4504469, rs2038137, rs2143340, or any combination thereof in a KIAA0319 gene within the DYX2 locus; or (c) any combination of the haplotypes in (a) and (b). Any sample that contains nucleic acid (e.g., genomic DNA; RNA) that can be analyzed for a haplotype of interest can be assayed; methods for analyzing nucleic acids are well known in the art and also described herein. They include, but are not limited to, hybridization-mediated methods and sequencing. The sample can be, for example, blood, cells, or tissue. Alternatively, genomic DNA can be sequenced and the presence or absence in the DYX2 locus of at least one haplotype that is associated with susceptibility for developing a LD in humans determined. The presence in the DYX2 locus of at least one haplotype that is associated with susceptibility for developing a LD in humans indicates that the individual is at risk for developing a LD.

Also the subject herein is a method of determining if a sample obtained from an individual comprises a marker for susceptibility for developing a learning disability (LD) that is reading disability (RD) or language impairment (LI), comprising: obtaining a sample that comprises nucleic acid from the individual and determining if the sample comprises at least one marker selected from the group consisting of: rs12636438; rs1679255; rs9521789; rs1983931; rs9814232; rs7995158; rs6573225; rs4082518; rs442555; rs259521; rs482700; rs7695228; rs1940309; rs505277; rs476739; rs867036; rs867035; rs2071674; rs7694946; rs4823324; rs180950; rs2590673; rs892100; rs1792745; rs12546767; rs12634033; rs892270; rs10887149; rs10041417; rs6792971; rs12636438; rs1679255; rs9521789; rs476739; rs505277; rs482700; rs7695228; rs867036; rs867035; rs1940309; rs16889556; rs1047782; rs1530680; rs12667130; rs6965855; rs985080; rs4726782; rs1718101; rs10487689; rs1918296; rs737533; rs793845; rs2799373;

rs793862; rs793834; rs2792682; rs807704; rs707864; rs12193738; rs2817198; rs10456309; rs985080; rs1554690; rs2533096; rs6951437; rs344470; rs344468; rs4725745; rs12444778; rs1444186; rs2294691; rs10456309; rs1562422; rs807694; rs3756814; rs3777663; rs9295626; rs7763790; rs6935076; rs9348646; rs2328791; rs2328791; rs2817201, rs9295626; rs4576240; rs17307478, rs9356939, rs7763790, rs6456621; rs6456624, rs6935076, rs2038137, rs3756821, rs1883593, rs3212236; rs3777663, rs3756814, rs6931809, rs6916186, rs6933328, rs17491647; rs2328791; rs33914824a; rs807694a; rs707864a; rs10456301a; rs16889066a; rs9379651a; rs2817201; rs9295626; rs10456309; rs4576240; rs17307478; rs9356939; rs7763790; rs6456621; rs3756821; rs1883593; rs3212236; rs2294691; rs3777663; rs3756814; rs6931809; rs6916186; rs6933328; rs17491647; rs9348646; rs1562422 and a marker for each of the following genes: R5H2; OR5H6; RRAGA; OR6B3; UMOD; A26C1A; FAM29A; CHRNA1; IFIT5; LOC643905; K2; DLEC1; NARS; IL4I1; PKD2; ATF5; NUP62; SIGLEC11; ACAN; PGD; MAP4; OR2L8; CRYBA4; OR2T8; KIAA1622; OR2AK2; DHX30; GEMIN6; C20orf10; and PPIF. The LD is reading disability (RD) or language impairment (LI) or both RD and LI. Any sample that contains nucleic acid (e.g., genomic DNA; RNA) that can be analyzed for a marker for susceptibility for developing a learning disability (LD) that is reading disability (RD) or language impairment (LI)can be assayed; methods for analyzing nucleic acids are well known in the art and also described herein. They include, but are not limited to, hybridization-mediated methods and sequencing. The sample can be, for example, blood, cells, or tissue. Alternatively, genomic DNA can be sequenced and the presence or absence of such a marker or markers.

Further described herein is a method of identifying or aiding in identifying an individual at risk for developing at least one learning disability (LD), comprising assaying a sample obtained from the individual for the presence in the DYX2 locus of at least one haplotype that is associated with susceptibility for developing a LD in humans, wherein the presence in the DYX2 locus of at least one haplotype that is associated with susceptibility for developing a LD in humans indicates that the individual is at risk for developing a LD. At least one LD is a reading disability (RD) or language impairment (LI). The at least one haplotype is located in the DCDC2 gene within the DYX2 locus or in the KIAA0319 gene within the DYX2 locus and can comprise (a) CGCGAG, CACGAG, or both CGCGAG and CACGAG in a DCDC2 gene within the DYX2 locus; or (b) rs4504469, rs2038137, rs2143340, or any combination thereof in a KIAA0319 gene within the DYX2 locus; or (c) any combination of the haplotypes in (a) and (b). In the method, the assay comprises a hybridization-mediated method, nucleic acid sequencing, or both a hybridization-mediated method and nucleic acid sequencing. The sample is blood, cells, or tissue.

Another embodiment is a method of identifying an individual as having, or being susceptible to developing, a learning disability (LD), comprising obtaining a sample comprising nucleic acid from an individual; determining whether nucleic acid in the sample comprises a DCDC2 gene haplotype in the DYX2 locus associated with susceptibility for developing reading disability (RD) and a KIAA0319 gene haplotype associated with susceptibility for developing language impairment (LI), wherein the DCDC2 gene haplotype and the KIAA0319 gene haplotype interact synergistically in decreasing performance in phoneme deletion and in resulting in a learning disorder (LD) in humans, wherein if the sample comprises both haplotypes, the individual is identified as having or being susceptible to developing a LD. In this method, the determining comprises a hybridization-mediated method, nucleic acid sequencing, or both a hybridization-mediated method and nucleic acid sequencing. The sample is blood, cells, or tissue.

In some embodiments, a method by which an individual is identified as having or being susceptible for developing a learning disability (LD) comprises treating the individual so identified. Treatment comprises providing interventions, including services and materials, including but not limited to: using special teaching techniques; making classroom modifications, such as providing extra time to complete tasks and taped tests to permit the individual to hear, rather than read the tests; using books on tape; using word-processing programs with spell-check features; helping the individual learn through multisensory experiences; teaching coping tools; and providing services to strengthen the individual's ability to recognize and pronounce words. See, for example, nichd.nih.gov/health/topics/learning/condition-info. What are the treatments for learning disabilities?

Another embodiment is a method of treating an individual for a learning disability (LD) comprising inhibiting ETV6 in the individual. The individual has RD, LI, or both.

In some embodiments, a method by which an individual is identified as at risk for developing a learning disorder further comprises monitoring the individual identified as at risk for developing a learning disability to assess whether development of a learning disability occurs and, if development occurs, treating the individual, wherein treating comprises providing interventions, including services and materials, including but not limited to: using special teaching techniques; making classroom modifications, such as providing extra time to complete tasks and taped tests to permit the individual to hear, rather than read the tests; using books on tape; using word-processing programs with spell-check features; helping the individual learn through multi-sensory experiences; teaching coping tools; and providing services to strengthen the individual's ability to recognize and pronounce words.

See, for example,nichd.nih.gov/health/topics/learning/conditioninfo. What are the treatments for learning disabilities?

Also described herein are arrays, such as microarrays (DNA arrays or microarrays). According to one embodiment, an array (e.g., microarray) for identifying or aiding in identifying an individual at risk for developing at least one learning disability (LD) is provided. The array comprises a support having a plurality of discrete regions (e.g., spots), each discrete region having (having affixed thereto) one or more nucleic acid fragment (e.g., probes) spotted or otherwise attached or deposited thereon. Typically, each discrete region bears a reagent, such as nucleic acid (DNA, RNA) that detects a marker (e.g., SNP, haplotype marker, allele, etc) associated with susceptibility for developing a LD (e.g., RD, LI) in humans. The nucleic acid fragments are complementary to nucleic acids (e.g., DNA, such as genomic DNA, or RNA, such as mRNA) that are markers for a variant gene, such as variant DCDC2, KIAA0319 and others named herein, associated with susceptibility for developing at least one LD (e.g., as provided herein). The nucleic acid fragments on a particular discrete region can be of any length and sequence (e.g., that complements the nucleic acid comprising a marker) suitable for the detection of any marker described herein. For example, in some embodiments, a nucleic acid fragment (e.g., probe, SNP probe) is between 10 and 100 nucleotides in length. In some embodiments, a nucleic acid fragment is between about 20 and 80, about 30 and 60, or about 40 and 50 nucleotides (nt) in length. In specific embodiments, the probes are 25 nt, 30 nt, 35 nt. or 40 nt in length. See, for example, LaFramboise, T., Nucl. Acids Res. (2009) 37 (13): 4181-4193. In some embodiments, a particular discrete region comprises a plurality of nucleic acid fragments (e.g., probes, SNP probes), each of which is capable of hybridizing to a particular marker. In some embodiments, the plurality of nucleic acid fragments are of varying lengths (e.g., as described herein) and sequences. In some embodiments, the array detects two or more markers associated with susceptibility for developing a learning disability (LD) in humans, wherein the two or more markers comprise one or more markers in a DCDC2 gene and one or more markers in a KIAA0319 gene. In some embodiments, the one or more markers in a DCDC2 gene are selected from CGCGAG, CACGAG, READ1 allele 5 (SEQ ID NO:35), READ1 allele 6 (SEQ ID NO:36), or any combination of two, three or four of CGCGAG, CACGAG, READ1 allele 5 (SEQ ID NO:35), and READ1 allele 6 (SEQ ID NO:36). In some embodiments, the one or more markers in a KIAA0319 gene are selected from rs4504469, rs2038137, rs2143340, or any combination of two or three of rs4504469, rs2038137 and rs2143340.

In some embodiments, the array (e.g., microarray) detects markers associated with susceptibility for developing language impairment (LI) in humans. In some embodiments, the array comprises discrete regions (e.g., discrete regions comprising one or more nucleic acid fragments) capable of detecting markers in a DCDC2 gene, such as CACGAG, READ1 allele 6 (SEQ ID NO:36), rs793845, rs2799373, rs793862, rs793834, rs2792682, rs807704, rs707864, rs807694, or any combination thereof. In some embodiments, the array (further) detects one or more markers in a KIAA0319 gene, such as rs12193738, rs2817198, rs10456309, or any combination thereof. In some embodiments, the array further comprises one or more discrete regions comprising nucleic acid fragments spotted on the support that detect one or more markers selected from rs985080, rs1554690, rs2533096, rs6951437, rs344470, rs344468, rs482700, rs7695228, rs1940309, rs505277, rs476739, rs867036, rs867035, rs2071674, rs7694946, rs4823324, and markers for the following genes: NEK2; DLEC1; NARS; IL4I1; PKD2; ATF5; NUP62; SIGLEC11; ACAN; and PGD.

In some embodiments, the array (e.g., microarray) detects markers associated with susceptibility for developing a reading disability (RD) in humans. In some embodiments, the array comprises discrete regions (e.g., discrete regions comprising one or more nucleic acid fragments) capable of detecting markers in a DCDC2 gene, CGCGAG and READ1 allele 5 (SEQ ID NO:35), or both. In some embodiments, the array (further) detects one or more markers in a KIAA0319 gene, such as rs10456309. In some embodiments, the array further comprises one or more discrete regions comprising nucleic acid fragments spotted on the support that detect one or more markers selected from rs180950, rs2590673, rs892100, rs1792745, rs12546767, rs12634033, rs892270, rs10887149, rs10041417, rs6792971, rs4725745, rs12444778, rs1444186, rs2294691, rs10456309, rs1562422, and a markers for the following genes: MAP4; OR2L8; CRYBA4; OR2T8; KIAA1622; OR2AK2; DHX30; GEMIN6; C20orf10; and PPIF.

In some embodiments, an array (e.g., microarray) is provided that detects one or more markers associated with susceptibility for developing a LD in humans, wherein the one or more markers are selected from rs12636438; rs1679255; rs9521789; rs1983931; rs9814232; rs7995158; rs6573225; rs4082518; rs442555; rs259521; rs482700; rs7695228; rs1940309; rs505277; rs476739; rs867036; rs867035; rs2071674; rs7694946; rs4823324; rs180950; rs2590673; rs892100; rs1792745; rs12546767; rs12634033; rs892270; rs10887149; rs10041417; rs6792971; rs12636438; rs1679255; rs9521789; rs476739; rs505277; rs482700; rs7695228; rs867036; rs867035; rs1940309; rs16889556; rs1047782; rs1530680; rs12667130; rs6965855; rs985080; rs4726782; rs1718101; rs10487689; rs1918296; rs737533; rs793845; rs2799373; rs793862; rs793834; rs2792682; rs807704; rs707864; rs12193738; rs2817198; rs10456309; rs985080; rs1554690; rs2533096; rs6951437; rs344470; rs344468; rs4725745; rs12444778; rs1444186; rs2294691; rs10456309; rs1562422; rs807694; rs3756814; rs3777663; rs9295626; rs7763790; rs6935076; rs9348646; rs2328791; rs2328791; rs2817201; rs9295626; rs4576240; rs17307478, rs9356939, rs7763790; rs6456621; rs6456624, rs6935076, rs2038137, rs3756821, rs1883593, rs3212236; rs3777663, rs3756814, rs6931809, rs6916186, rs6933328, rs17491647; rs2328791; rs33914824a; rs807694a; rs707864a; rs10456301a; rs16889066a; rs9379651a; rs2817201; rs9295626; rs10456309; rs4576240; rs17307478; rs9356939; rs7763790; rs6456621; rs3756821; rs1883593; rs3212236; rs2294691; rs3777663; rs3756814; rs6931809; rs6916186; rs6933328; rs17491647; rs9348646; rs1562422 and markers of the following genes: R5H2; OR5H6; RRAGA; OR6B3; UMOD; A26C1A; FAM29A; CHRNA1; IFIT5; LOC643905; K2; DLEC1; NARS; IL4I1; PKD2; ATF5; NUP62; SIGLEC11; ACAN; PGD; MAP4; OR2L8; CRYBA4; OR2T8; KIAA1622; OR2AK2; DHX30; GEMIN6; C20orf10; and PPIF.

DETAILED DESCRIPTION

Figure 1:
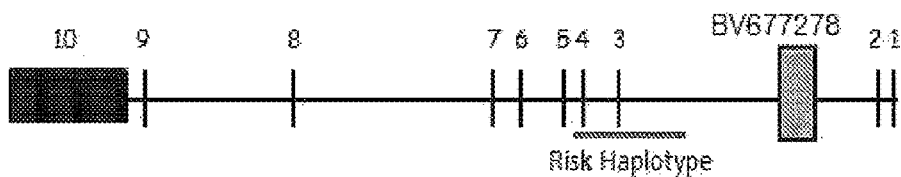
FIG. 1: (A) Structure of the BV677278 STR. (B) Location of the risk haplotype block within the DCDC2 gene, relative to BV677278. Exons are numbered.

Variant DCDC2 and Variant KIAA0319 Polynucleotide Probes and Primers

Provided here are isolated, synthetic and recombinant polynucleotides that detect an alteration in a DCDC2 gene (referred to as a variant DCDC2 gene) that is associated with susceptibility to developing a learning disability (LD), such as isolated and recombinant polynucleotides that detect an alteration of DCDC2 in the DYX2 locus. The variant is, for example, a DCDC2 risk haplotype (e.g., CGCGAG, CACGAG), allele 5 of BV677278 (READ1); allele 6 of BV677278 (READ1); or one, two or three or more of the variants associated with susceptibility to developing a learning disability (LD). Also provided are isolated, synthetic and recombinant polynucleotides that detect an alteration in a KIAA0319 gene (referred to as a variant KIAA0319 gene) that is associated with susceptibility to developing a learning disability (LD), such as isolated and recombinant polynucleotides that detect an alteration of KIAA0319 in the DYX2 locus. The variant is, for example, a KIAA0319 risk haplotype (e.g., rs4504469, rs2038137, rs2143340); or one, two or three or more of the variants associated with susceptibility to developing a learning disability (LD). The LD is a reading disability (RD) or a language impairment (LI). Polynucleotide probes typically have a sequence which is fully or partially complementary to the sequence of the alteration and the flanking region and hybridize to the alteration of interest, and the flanking sequence in a specific manner. A variety of alterations in a DCDC2 gene or in a KIAA0319 gene associated with susceptibility for developing LD, such as RD and LI, may be detected by the polynucleotides described herein. For example, a single nucleotide polymorphism (SNP) of a coding region, exon, exon-intron boundary, signal peptide, 5-prime untranslated region, promoter region, enhancer sequence, 3-prime untranslated region or intron that is associated with LD such as RD and LI can be detected. These polymorphisms include, but are not limited to, those that result in changes in the amino acid sequence of the proteins encoded by the DCDC2 gene and changes in the amino acid sequence of the proteins encoded by the KIAA0319 gene, produce alternative splice products, create truncated products, introduce a premature stop codon, introduce a cryptic exon, alter the degree or expression to a greater or lesser extent, alter tissue specificity of DCDC2 and/or KIAA0319 expression (e.g., at either the mRNA or protein level), introduce changes in the tertiary structure of the proteins encoded by DCDC2 and/or KIAA0319, introduce changes in the binding affinity or specificity of the proteins expressed by DCDC2 and/or KIAA0319 or alter the function of the proteins encoded by DCDC2 and/or KIAA0319. The subject polynucleotides include polynucleotides that are variants of the polynucleotides described herein, as long as the variant polynucleotides maintain their ability to specifically detect a variation in the DCDC2 gene that is associated with susceptibility for developing LD, such as RD and/or LI or in the KIAA0319 gene that is associated with susceptibility for developing LD, such as RD and/or LI. Variant polynucleotides may include, for example, sequences that differ by one or more nucleotide substitutions, additions or deletions.

In certain embodiments, the isolated or recombinant polynucleotide is a probe that hybridizes, under stringent conditions, such as highly stringent conditions, to an alteration in the DCDC2 gene that is associated with susceptibility for developing a LD, or to an alteration in the KIAA0319 gene that is associated with susceptibility for developing a LD. A LD can be, for example, a reading disability (RD) or language impairment (LI). As used herein, the term "hybridization" is used in reference to the pairing of complementary nucleic acids. The term "probe" refers to a polynucleotide that is capable of hybridizing to another nucleic acid of interest. The polynucleotide may be naturally occurring, as in a purified restriction digest, or it may be produced synthetically, recombinantly or by nucleic acid amplification (e.g., PCR amplification).

It is well known in the art how to perform hybridization experiments with nucleic acid molecules. The skilled artisan is familiar with hybridization conditions and that appropriate stringency conditions which promote DNA hybridization can be varied. Such hybridization conditions are referred to in standard text books such as Molecular Cloning: A Laboratory Manual, Cold Spring Harbor Laboratory (1989); and Current Protocols in Molecular Biology, eds. Ausubel et al., John Wiley & Sons: 1992. In one embodiment, the polynucleotides hybridize to a variation in the DCDC2 gene, to a variation in a KIAA0319 gene, or to both a variation in the DCDC2 gene and the KIAA0319 gene (e.g., use of distinct probes that hybridize to each gene, respectivelt). Under highly stringent conditions, essentially no hybridization to unrelated polynucleotides occurs.

Nucleic acid hybridization is affected by such conditions as salt concentration, temperature, organic solvents, base composition, length of the complementary strands, and the number of nucleotide base mismatches between the hybridizing nucleic acids, as will readily be appreciated by those skilled in the art. Stringent temperature conditions will generally include temperatures in excess of 30° C., or may be in excess of 37° C. or 45° C. Stringent salt conditions will ordinarily be less than 1000 mM, or may be less than 500 mM or 200 mM. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, nucleic acids hybridize under low stringency conditions of 6.0× SSC at room temperature followed by a wash at 2.0×SSC at room temperature. The combination of parameters, however, is much more important than the measure of any single parameter. See, e.g., Wetmur and Davidson, *J Mol Biol*. 1968; 31(3):349-70. Probe sequences may also hybridize specifically to duplex DNA under certain conditions to form triplex or higher order DNA complexes. The preparation of such probes and suitable hybridization conditions are well known in the art. One method for obtaining DNA encoding the biosynthetic constructs disclosed herein is by assembly of synthetic oligonucleotides produced in a conventional, automated, oligonucleotide synthesizer.

A polynucleotide probe or primer used in a method described herein may be labeled with a reporter molecule, so that it is detectable in a detection system, including, but not limited to, enzyme (e.g., ELISA, as well as enzyme-based histochemical assays), fluorescent, radioactive, chemical, and luminescent systems. A polynucleotide probe or primer used in a method described herein may further include a quencher moiety that, when placed very close to a label (e.g., a fluorescent label), causes there to be little or no signal from the label. It is not intended that the present invention be limited to any particular detection system or label.

In another embodiment, the isolated polynucleotide is a primer that hybridizes adjacent, upstream, or downstream to an alteration in the DCDC2 gene or the KIAA0319 gene that is associated with susceptibility for developing a LD in humans. For example, a polynucleotide primer can hybridize adjacent, upstream, or downstream to an alteration in the DCDC2 gene or adjacent, upstream, or downstream to an alteration in the KIAA0319 gene that is associated with susceptibility for developing a LD (e.g., RD, LI). As used herein, the term "primer" refers to a polynucleotide that acts as a point of initiation of nucleic acid synthesis when placed under conditions in which synthesis of a primer extension product that is complementary to a nucleic acid strand is induced (e.g., in the presence of nucleotides, an inducing agent such as DNA polymerase, and suitable temperature, pH, and electrolyte concentration). Alternatively, the primer ligates to a proximal nucleic acid when placed under conditions in which ligation of two unlinked nucleic acids is induced (e.g., in the presence of a proximal nucleic acid, an inducing agent such as DNA ligase, and suitable temperature, pH, and electrolyte concentration). A polynucleotide primer may be naturally occurring, as in a purified restriction digest, or may be produced synthetically. The primer is single stranded or double stranded. If double stranded, the primer is treated to separate its strands before being used. The primer can be an oligodeoxyribonucleotide. The exact lengths of the primers will depend on many factors, including temperature, source of primer and the method used.

One embodiment is a pair of primers that specifically detect an alteration in a DCDC2 gene or an alteration in a KIAA0319 gene that is associated with susceptibility for developing a LD. In such a case, the first primer hybridizes upstream from the alteration and a second primer hybridizes downstream from the alteration. One of the primers hybridizes to one strand of a region of DNA that comprises an alteration in the DCDC2 gene or in the KIAA0319 gene that is associated with susceptibility for developing LD and the second primer hybridizes to the complementary strand of a region of DNA that comprises an alteration in the DCDC2 gene or in the KIAA0319 gene that is associated with susceptibility for developing a LD. As used herein, the term "region of DNA" refers to a sub-chromosomal length of DNA. Other embodiments are pairs of primers that specifically detect alterations in other genes, described herein, that are associated with a susceptibility for developing a learning disability. A further embodiment is a set of three primers useful for distinguishing between two alleles of DCDC2, wherein the first allele is a non-deleted DCDC2 gene (e.g., an allele that does not comprise a deletion of READ1) and the second allele comprises a deletion in the DCDC2 gene (e.g., comprises allele 39/indicated Del. in Table S4, Example 1) that is associated with susceptibility for LD. The first primer hybridizes to a nucleotide sequence that is common to both alleles, such as a non-allelic nucleotide sequence that is upstream or downstream of the polymorphic sequence in the DCDC2 gene. The second primer specifically hybridizes to a nucleotide sequence that is unique to a first allele (e.g., a non-deleted DCDC2 gene). The third primer specifically hybridizes to a nucleotide sequence that is unique to the second allele (e.g., a deletion in the DCDC2 gene that is associated with susceptibility for RD). Use of the set of three primers results in amplification of a region of DNA that is dependent on which DCDC2 allele is present in the sample. Alternatively, two primers of the set hybridize to a nucleotide sequence that is common to two alleles of the DCDC2 gene, such as non-allelic nucleotide sequences that are upstream and downstream of a polymorphic sequence in the DCDC2 gene, and the third primer specifically hybridizes to one of the two alleles of the DCDC2 gene.

Variant DCDC2 Polynucleotide Probes and Primers

The polynucleotides may be used in any assay that permits detection of a variation in the DCDC2 gene that is associated with susceptibility for developing a LD (e.g., RD, LI). Such methods may encompass, for example, hybridization-mediated, ligation-mediated, or primer extension-mediated methods of detection. Furthermore, any combination of these methods may be utilized in the invention.

In one embodiment, the polynucleotides detect an alteration in the DCDC2 gene that is associated with susceptibility for developing a LD by amplifying a region of DNA that comprises the alteration in the gene. Any method of amplification may be used. In a second embodiment, the polynucleotides detect an alteration in the KIAA0319 gene that is associated with susceptibility for developing a LD by amplifying a region of DNA that comprises the alteration in the gene. In one specific embodiment, a region of DNA comprising an alteration is amplified by using polymerase chain reaction (PCR). (Ann. Rev. Biochem., 61:131-156 (1992)); Gilliland et al, Proc. Natl. Acad. Sci., 87: 2725-2729 (1990); Bevan et al, PCR Methods and Applications, 1: 222-228 (1992); Green et al, PCR Methods and Applications, 1: 77-90 (1991); Blackwell et al, Science, 250: 1104-1110 (1990). PCR refers, for example, to the method of Mullis (See e.g., U.S. Pat. Nos. 4,683,195 4,683,202, and 4,965,188, herein incorporated by reference), which describes a method for increasing the concentration of a region of DNA, in a mixture of genomic DNA, without cloning or purification. For example, the polynucleotide primers described herein of the invention are combined with a DNA mixture (or any polynucleotide sequence that can be amplified with the polynucleotide primers), wherein the DNA comprises the DCDC2 gene and/or the KIAA0319 gene. The mixture also includes the amplification reagents (e.g., deoxyribonucleotide triphosphates, buffer, etc.) necessary for the thermal cycling reaction. According to standard PCR methods, the mixture undergoes a series of denaturation, primer annealing, and polymerase extension steps to amplify the region of DNA that comprises a variation in the DCDC2 gene and/or a variation in the KIAA0319 gene. The length of the amplified region of DNA is determined by the relative positions of the primers with respect to each other and, therefore, this length is a controllable parameter. For example, hybridization of the primers may occur such that the ends of the primers proximal to the mutation are separated by 1 to 10,000 base pairs (e.g., 10 base pairs (bp) 50 bp, 200 bp, 500 bp, 1,000 bp, 2,500 bp, 5,000 bp, or 10,000 bp).

Standard instrumentation is used for amplification of DNA and detection of amplified DNA. For example, a wide variety of instrumentation has been developed for carrying out nucleic acid amplifications, particularly PCR, e.g. Johnson et al, U.S. Pat. No. 5,038,852 (computer-controlled thermal cycler); Wittwer et al, Nucleic Acids Research, 17: 4353-4357 (1989) (capillary tube PCR); Hallsby, U.S. Pat. No. 5,187,084 (air-based temperature control); Garner et al, Biotechniques, 14: 112-115 (1993) (high-throughput PCR in 864-well plates); Wilding et al, International application No. PCT/US93/04039 (PCR in micro-machined structures); Schnipelsky et al, European patent application No. 90301061.9 (publ. No. 0381501 A2) (disposable, single use PCR device). In certain embodiments, real-time PCR or other methods known in the art, such as the Taqman assay, is used.

Amplified DNA may be analyzed by several different methods. Such methods for analyzing the amplified DNA include, but are not limited to, (Sanger) sequencing of the DNA, determining the size of the fragment by electrophoresis or chromatography, hybridization with a labeled probe, hybridization to a DNA array or microarray, incorporation of biotinylated primers followed by avidin-enzyme conjugate detection, or incorporation of $^{32}$P-labeled deoxynucleotide triphosphates, such as dCTP or dATP, into the amplified segment. In one embodiment, the amplified DNA is analyzed by gel electrophoresis. Methods of gel electrophoresis are well known in the art. See for example, Current Protocols in Molecular Biology, eds. Ausubel et al., John Wiley & Sons: 1992. Amplified DNA can be visualized, for example, by fluorescent or radioactive means. The DNA may also be transferred to a solid support such as a nitrocellulose membrane and subjected to Southern Blotting following gel electrophoresis. In one aspect, the DNA is analyzed by electrophoresis and exposed to ethidium bromide and visualized under ultra-violet light.

In one aspect, the alteration in the DCDC2 gene that is associated with susceptibility for developing RD is a deletion. The deletion may be detected using polynucleotide primers described herein. For example, a set of three primers may be used to distinguish between an allele of the DCDC2 gene that comprises a deletion and a wildtype DCDC2 gene. Use of the set of three primers results in amplification of a region of DNA that is dependent on which DCDC2 allele is present in the sample. In some instances, a deletion is protective, such as allele 39/Del in Table S4 of Example 1. In some embodiments, alterations or variants are protective.

In another embodiment, amplified DNA is analyzed by DNA sequencing. DNA sequence determination may be performed by standard methods such as dideoxy chain termination technology (Sanger sequencing) and gel-electrophoresis, or by other methods such as by pyrosequencing (Biotage AB, Uppsala, Sweden). The nucleic acid sequence of the amplified DNA can be compared to the nucleic acid sequence of wild type DNA to identify whether a variation in the DCDC2 and/or KIAA0319 gene that is associated with susceptibility for developing LD is present.

In another embodiment, the polynucleotides of the disclosure detect an alteration in the DCDC2 gene that is associated with susceptibility for developing a LD by hybridization-mediated methods. In a further embodiment, the polynucleotides detect an alteration in the KIAA0319 gene that is associated with susceptibility for developing a LD by hybridization-mediated methods. In one embodiment, a polynucleotide probe hybridizes to an alteration in the DCDC2 gene that is associated with susceptibility for developing a LD (and to flanking nucleotides), but not to a wild type DCDC2 gene. In another embodiment, a polynucleotide probe hybridizes to an alteration in the KIAA0319 gene that is associated with susceptibility for developing a LD (and flanking nucleotides), but not to a wild type KIAA0319 gene. The polynucleotide probe may comprise nucleotides that are fluorescently, radioactively, or chemically labeled to facilitate detection of hybridization. Hybridization may be performed and detected by standard methods known in the art, such as by Northern blotting, Southern blotting, fluorescent in situ hybridization (FISH), or hybridization to polynucleotides on a solid support (e.g., DNA arrays, microarrays, cDNA arrays, or Affymetrix chips). In one embodiment, the polynucleotide probe is used to hybridize genomic DNA by FISH. FISH can be used, for example, in metaphase cells, to detect a deletion in genomic DNA. Using FISH, genomic DNA is denatured to separate the complementary strands within the DNA double helix structure. The polynucleotide probe is combined with the denatured genomic DNA. If an alteration in the DCDC2 gene that is associated with susceptibility for developing a LD or an alteration in the KIAA0319 gene that is associated with susceptibility for developing a LD is present, the probe will hybridize to the genomic DNA. The probe signal (e.g., fluorescence) can be detected through a fluorescent microscope for the presence or absence of signal. The absence of signal indicates the absence of an alteration in the DCDC2 gene that is associated with susceptibility for developing a LD (e.g., RD, LI) or the absence of an alteration in the KIAA0319 gene that is associated with susceptibility for developing a LD (e.g., RD, LI). Alternatively, presence of signal can be used to determine the absence of an alteration in the DCDC2 or KIAA0319 gene.

In another embodiment, the polynucleotides detect an alteration in the DCDC2 gene that is associated with susceptibility for developing a LD (e.g., RD, LI) or an alteration in the KIAA0319 gene that is associated with susceptibility for developing a LD (e.g., RD, LI) by primer extension with DNA polymerase. In one embodiment, a polynucleotide primer hybridizes immediately adjacent to the alteration. A single base sequencing reaction using labeled dideoxynucleotide terminators may be used to detect the alteration. If an alteration is present, the labeled terminator will be incorporated into extension product; if an alteration is not present, the labeled terminator will not be incorporated. In another aspect, a polynucleotide primer hybridizes to an alteration in the DCDC2 gene that is associated with susceptibility for developing a LD or an alteration in the KIAA0319 gene that is associated with susceptibility for developing a LD. The primer, or a portion thereof, will not hybridize to a wild type DCDC2 or wild type KIAA0319 gene. If an alteration is present, primer extension occurs; if an alteration is not present, primer extension does not occur. The primers and/or nucleotides may further include fluorescent, radioactive, or chemical probes. A primer labeled by primer extension may be detected by measuring the intensity of the extension product, such as by gel electrophoresis, mass spectrometry, or any other method for detecting fluorescent, radioactive, or chemical labels.

In another embodiment, the polynucleotides detect an alteration in the DCDC2 gene that is associated with susceptibility for developing a LD or an alteration in the KIAA0319 gene that is associated with susceptibility for developing a LD by ligation. In one aspect, a polynucleotide primer hybridizes to a variation in the DCDC2 gene that is associated with susceptibility for developing a LD or to a variation in the KIAA0319 gene that is associated with susceptibility for developing a LD. The primer will not hybridize to the wild type gene (e.g., wild type DCDC2 gene). A second polynucleotide that hybridizes to a region of the DCDC2 gene immediately adjacent to the first primer or to a region of the KIAA0319 gene immediately adjacent to the first primer is also provided. One, or both, of the polynucleotide primers may be fluorescently, radioactively, or chemically labeled. Ligation of the two polynucleotide primers occurs in the presence of DNA ligase if an alteration in the gene (e.g., an alteration DCDC2 or KIAA0319 gene) that is associated with susceptibility for developing a LD is present. Ligation may be detected by gel electrophoresis, mass spectrometry, or by measuring the intensity of fluorescent, radioactive, or chemical labels.

EXAMPLES

The following examples are for illustrative purposes and are not intended to be limiting in any way.

Example 1

Materials and Methods

Subject Recruitment, Data and DNA Collection, and Data Management.

Subject recruitment and collection of phenotype data and DNA for the ALSPAC cohort was done by the ALSPAC team, under the supervision of S. M. Ring and these data were managed for this study by L. L. Miller.

The Avon Longitudinal Study of Parents and Children (ALSPAC)

The ALSPAC is a prospective birth cohort based in the Avon region of the United Kingdom. It consists of children mostly of northern European descent, born in 1991 and 1992. Children were recruited before birth; recruitment of their pregnant mothers resulted in a total of 15,458 fetuses, of whom 14,701 were alive at 1 year of age. Details regarding the participants, recruitment, and study methodologies are described in detail elsewhere (bristol.ac.uk/alspac) The children of the ALSPAC have been extensively phenotyped from before birth to early adulthood. An update on the status of the cohort was published in 2012. (S11). The reading, language, and cognitive measures used for this study were collected at ages 7, 8, and 9 years. DNA samples from 10,676 of these children were available for genotyping. Of this subset, the number of children who completed the language and cognitive measures varies by measure, but is generally 5200-5600 subjects.

ALSPAC Reading Measures

Reading measures in the ALSPAC include a phoneme deletion task at age 7, single-word reading at ages 7 and 9, spelling at ages 7 and 9, single non-word reading at age 9, and passage comprehension, speed and accuracy at age 9. The phoneme deletion task measures phoneme awareness (S12), which is widely considered to be a core deficit in RD (S13). The child listens to a word spoken aloud, and is then asked to remove a specific phoneme from that word to make a new word (e.g. what word is created when the /b/ sound is removed from the word 'block'? 'Lock.'). This task is also known as the Auditory Analysis Test, and was developed by Rosner and Simon (S14). Single-word reading was assessed at age 7 using the reading subtest of the Wechsler Objective Reading Dimensions (WORD) (S15). At age 7 and 9, spelling was assessed; the child was asked to spell a set of 15 age-adjusted words (S15). At age 9, single-word reading was again assessed by asking the child to read ten real words and ten non-words aloud. The words and non-words used are a subset of a larger list of words and non-words taken from research conducted by Terezinha Nunes and others at Oxford (S16). Reading speed, accuracy, and comprehension scores were ascertained at age 9, using the Neale Analysis of Reading Ability (NARA-II) (S17). All three measures are standardized. The child read passages from a booklet aloud and immediately afterward was asked questions about what he/she read to assess reading comprehension. Accuracy was measured by counting the number of mistakes (mispronunciations, substitutions, etc.) the child made and converting to a standardized score. Reading speed was number of words per minute.

ALSPAC Language Measures

The language measures focused on for this study were ascertained at 8 years of age. The first of these is a non-word repetition (NWR) task, wherein the child is asked to repeat recorded non-words. This task measures short-term phonological memory and processing (S18). The second is a subtest of the Wechsler Objective Language Dimensions that measures language comprehension (WOLD Comp) (S19). For this task, the child is asked a series of questions about a paragraph describing a picture, which was read aloud by an examiner. Children with LI consistently perform poorly on these measures (S20, S21).

ALSPAC IQ Assessment

Verbal, performance, and total IQ were assessed at age 8, using the Wechsler Intelligence Scale for Children (WISC-III).

Ethical Approval

Ethical approval for the study was obtained from the ALSPAC Ethics and Law Committee, the Local UK Research Ethics Committee, and the Yale Human Investigation Committee.

DYX2 TagSNP Panel Design and Genotyping.

TagSNPs designed to capture the common variation in the DYX2 locus were selected using the association study design server of Han et. al. (design.cs.ucla.edu) (33). SNPs were genotyped on the Sequenom platform, in collaboration with the Yale Center for Genome Analysis (West Haven, Conn.), as per standard protocols. Call rate and descriptive statistics for the SNPs described herein are listed in Table S4. rs4504469, rs2038137, and rs2143340 were genotyped by Scerri et. al., as described (24).). Minor allele frequency for all tagSNPs was greater than or equal to 0.05. Average power to capture known common variants (MAF>0.05) within DYX2 using this panel was estimated at 83.44% a priori. A number of other SNPs were included in addition to the tagSNP panel, including several that had been previously associated with RD and coding SNPs in DCDC2.

Haplotype-Based Association Analysis.

Linkage disequilibrium was assessed and haplotypes defined using the Haploview software package, version 4.2 (34). Markers that deviated substantially from Hardy-Weinberg equilibrium, or that had a call rate <85%, were not used for haplotype analysis. The four-gamete rule option was used to demarcate haplotype blocks, which resulted in 44 haplotype blocks covering the DYX2 locus. Association analysis was performed with individual haplotypes that had frequencies of 0.01 or greater (208 total), using the Plink software package, version 1.07 (S4). The association analyses were performed using chi squared and logistic regression test statistics (-hap-assoc and -hap-logistic options). Individuals who were not identified as non-Hispanic white, who had a total IQ below 75, or whose DNA sample returned an average call rate below 85% for SNPs that passed quality control, were excluded from association analysis. To correct for multiple testing, a Bonferroni correction with the alpha level set at 0.05 was applied, treating each of the 208 haplotypes as an individual test; the threshold level is therefore 0.05/208=2.4038×10-4. As each phenotype constituted an independent hypothesis (phonological awareness and language), this threshold was not doubled to account for there being two phenotypes.

BV677278 Genotyping.

Carriers of the DCDC2 haplotypes of interest that could be phased unequivocally (using Plink's -hap-phase function) were genotyped for the BV677278 STR. BV677278 is genotyped by PCR amplification and subsequent Sanger sequencing. Alleles are called by an in-house Perl script developed by Y. Kong. The Perl script is available upon request.

```
Amplification Primers
STR_F:
                                            (SEQ ID NO: 1)
5'-TGTAAAACGACGGCCAGTTGTTGAATCCCAGACCACAA-3'

STR_R:
                                            (SEQ ID NO: 2)
5'-ATCCCGATGAAATGAAAAGG-3'

M13F Sequencing Primer
                                            (SEQ ID NO: 3)
5'-TGTAAAACGACGGCCAGT
```

Amplification Reaction Mixture (per 10 µl reaction)
10× PCR Buffer (Qiagen): 1 µl
MgCl$_2$ (25 mM) (Qiagen): 0.4 µl
dNTPs (10 mM): 0.25 µl
Primer STR_F (10 µM): 0.25 µl
Primer STR_R (10 µM): 0.25 µl
HotStarTaq™ (Qiagen, diluted to 0.5 units/µl in Taq dilution buffer): 0.20 µl
Template DNA: 1 µl (~10 ng/µl )
Nuclease-free H$_2$O: 6.65 µl
Amplification Reaction
1. 15 minutes, 95° C.
2. 30 seconds, 95° C.
3. 30 seconds, 65° C.
Decrease 1° C./cycle
4. 60 seconds, 72° C.
5. GoTo step 2, 9 times
6. 30 seconds, 95° C.
7. 30 seconds, 56° C.
8. 60 seconds, 72° C.
9. GoTo step 6, 34 times
10. 5 minutes, 72° C.
11. ∞, 4° C.

PCR Purification and Sequencing

PCR products were purified using ExoSAP-IT® enzyme mix, according to the manufacturer's protocol. Purified amplicons were then mixed with M13F sequencing primer, and sequenced. Sanger sequencing was performed at the Yale W. M. Keck DNA Sequencing Facility, as per their standard sequencing protocol.

Genotype Calling

Alleles were called from the electropherograms, using an in-house Perl script developed by Y. Kong for the purpose.

Microdeletion Genotyping.

Carriers of the DCDC2 haplotypes of interest were also genotyped for the 2,445bp DCDC2 microdeletion. This deletion encompasses the entire BV677278 STR within its breakpoints, so it must be genotyped in addition to BV677278 to get an accurate genotype for apparent BV677278 homozygotes. The microdeletion is genotyped by allele-specific PCR and agarose electrophoresis. The three-primer reaction generates a ~600 bp amplicon from intact chromosomes (no deletion), and a ~200 bp amplicon from chromosomes with the deletion, allowing heterozygotes and both homozygotes to be readily distinguishable from one another.

Amplification Primers

```
                                            (SEQ ID NO: 4)
Primer Del_F:     5'-AGCCTGCCTACCACAGAGAA-3'

(SEQ ID NO: 5)
Primer Del_RC:    5'-GGAACAACCTCACAGAAATGG-3'

(SEQ ID NO: 6)
Primer Del_RD:    5'-TGAAACCCCGTCTCTACTGAA-3'
```

Amplification Reaction Mixture (per 10 µl reaction)
10× PCR Buffer (Qiagen): 1 µl
MgCl$_2$ (25 mM) (Qiagen): 0.4 µl
dNTPs (10 mM): 0.25 µl
Primer Del_F (10 µM): 0.30 µl
Primer Del_RC (10 µM): 0.20 µl
Primer Del_RD: 0.20 µl
HotStarTaq™ (Qiagen, diluted to 0.5 units/µl in Taq dilution buffer): 0.20 µl
Template DNA: 1 µl (~10 ng/µl)
Nuclease-free H$_2$O: 6.45 µl
Amplification Reaction
The amplification reaction for the microdeletion is the same as for the BV677278 STR (see above).

Agarose Electrophoresis

PCR products were electrophoresed on 1% agarose gels, using standard 1× TBE buffer with ethidium bromide (0.2 µg/mL), via standard methods, at 100-150V depending on gel size. Gels were imaged on a UV transilluminator, and documented with a Bio-Rad Gel Doc™ XR imaging system. Genotypes were called from the gels manually.

Protein Identification by SILAC-Based Mass Spectrometry.

Raji and HeLa cells were SILAC-labeled with with Lys-8 and Arg-10 (Eurisotop) or their naturally-occurring counterparts Lys-0, Arg-10 (Sigma), as described (20). Heavy nuclear lysate prepared from these cells was incubated with a biotinylated oligonucleotide probe identical to a segment of BV677278 that had been previously shown to bind a nuclear protein with high specificity (15). Light nuclear lysate was incubated with a biotinylated scrambled probe previously shown not to bind the nuclear protein of interest (15). The resulting oligonucleotide-protein complexes were pulled down with streptavidin-conjugated beads and subjected to quantitative mass spectrometry, as described previously (36). The reverse experiment was also done (binding probe with light lysate, scrambled probe with heavy lysate), resulting in the two-dimensional interaction plots in FIG. 3A-B. The above experiment is described in more detail as follows:

SILAC Labeling of HeLa and Raji Cells

Raji cells were labeled for at least 8 generations in DMEM (-Arg, -Lys) medium containing 10% dialyzed fetal bovine serum (Gibco) supplemented with 58 mg/L 13C615N4 L-arginine and 34 mg/L 13C615N2 L-lysine (Eurisotop) or the corresponding non-labeled amino acids. For Raji, cell extracts were prepared as described in Wu et. al.(S5). HeLa S3 cells were SILAC-labeled in RPMI 1640 (-Arg, -Lys) medium containing 10% dialyzed fetal bovine serum (Gibco) supplemented with 84 mg/L 13C615N4 L-arginine and 40 mg/L 13C615N2 L-lysine (Eurisotop) or the corresponding non-labeled amino acids, respectively. For HeLa S3, three consecutive batches of cells were independently harvested and cell extracts prepared as described by Dignam et. al.(S6).

SILAC, DNA pulldown of proteins, and quantitative mass spectrometry were performed as previously described (S7), using the cell lines Raji and HeLa. The binding pulldown probe is a concatamer of two copies of the EMSA3 probe used in the EMSA experiments we reported in 2011, while the scrambled probe is a concatamer of two copies of the EMSA3-Scram1 probe from the same experiments (S8).

Oligonucleotides:

```
EMSA3_for:
                                           (SEQ ID NO: 7)
5'-TTGAGAGGAAGGAAAGGAAGGATCCCTGAGAGGAAGGAAAGGAAGG
A-3'

EMSA3_rev:
                                           (SEQ ID NO: 8)
5'-AATCCTTCCTTTCCTTCCTCTCAGGGATCCTTCCTTTCCTTCCTCT
C-3'

EMSA3/Scram1_for:
                                           (SEQ ID NO: 9)
5'-TTGAGAGAGAGAGAGAGAGAGATCCCTGAGAGAGAGAGAGAGAGAG
A-3'

EMSA3/Scram1_rev:
                                           (SEQ ID NO: 10)
5'-AATCTCTCTCTCTCTCTCTCAGGGATCTCTCTCTCTCTCTCT
C-3'
```

DNA-Pulldown

25 μg of annealed, concatenated and desthiobiotinylated DNA probes was bound to 75 μl of Dynabeads MyOne C1 (Life Technologies). Excess oligonucleotides were removed and beads were incubated with 400 μg of SILAC-labelled nuclear extracts in protein binding buffer (150 mM NaCl, 50 mM Tris-HCl (pH 8), 0.5% NP-40, 10 mM $MgCl_2$, protease inhibitor cocktail; Roche). After 1 h of on a rotation wheel at 4° C., the beads were washed three times, combined and DNA-protein complexes eluted in protein binding buffer containing 16 mM biotin. The supernatant was precipitated with 4 volumes (v/v) of ethanol overnight and the proteins pellets by maximum centrifugation on a table top microcentrifuge. The pellet was resolubilized in 8M urea/50 mM Tris pH8.0, reduced with 1 mM DTT, alkylated with 3 mM iodoacetamide and subsequently digested with trypsin (Promega) in 50 mM ammonium bicarbonate pH8 buffer at room temperature overnight. Samples were stored on stage tips and eluted prior to use.

Mass spectrometry

Peptides were separated with a 140 min gradient from 5 to 60 percent acetonitril (EasyHPLC, Thermo Fisher) using a 75 um 15 cm capillary packed with 3.0 um C18 beads (Dr. Maisch) directly mounted to a LTQ-Orbitrap mass spectrometer (Thermo Fisher). The instrument was operated in a data-dependent top 10 acquisition modus. The raw data was searched using the MaxQuant software (version 1.2.0.18) suite against the complete IPI human database (v3.68, 87061 entries). Enzyme search specificity was trypsin/p with 2 allowed miscleavages. Carbamidomethylation was set as fixed modification while methionine oxidation and protein N-acetylation was considered as variable modifications. The search was performed with an initial mass tolerance of 7 ppm mass accuracy for the precursor ion and 0.5 Da for the MS/MS spectra.

ChIP-QPCR.

The AbCam ChIP kit (cat. # ab500) was used to perform the ChIP assays described, according to the manufacturer's instructions, but with several modifications described below. For qPCR, the Qiagen QuantiTect® SYBR® Green qPCR kit for ChIP-qPCR was used. Manufacturer's instructions were followed 25 pg of template per reaction. All reactions in triplicate. Antibodies, primer sequences, and detailed methods for this experiment are available in the Supporting Information. Quality control data for qPCR is shown in FIG. S3.

Step 1: Cell Fixation and Collection

For each set of 3 ChIP reactions, 9 million freshly harvested cells (Raji) were used instead of 3 million, with volumes appropriate for 9 million cells, as given in the protocol.

Step 2: Cell Lysis

After the final PBS wash in the cell fixation step, each aliquot of 9 million cells was carried through the cell lysis step with volumes appropriate for 3 million cells (9 million treated as if it were 3 million—resulting in 3 million cells per ChIP reaction instead of 1 million).

100 μl Buffer D with protease inhibitors was replaced with ~150 μl of the following:

Buffer D2/PI (S9)

10 mM Tris 1 mM EDTA 0.5 mM EGTA pH=7

1× Protease Inhibitor Cocktail

A Branson 450 probe sonicator was used for sonication. DNA was fragmented with 18 20-second pulses, with the amplitude set to 6 and the DC set to continuous. The samples were kept in ice water during sonication and were allowed to rest 2 minutes on ice between each pulse.

Step 3: Immunoprecipitation

Followed manufacturer's protocol.

α-ETV6 antibody: sc-166835X (Santa Cruz Biotech), 5 μg/ChIP

Control antibody: ab1791 (AbCam) (α-variant histone H3, enriched in actively transcribing genes, an aliquot of this comes with the kit), 2 μg/ChIP Instead of the beads provided in the kit, Magna-Bind™ Protein A/G magnetic beads were used and a magnet stand, according to manufacturer's protocol was used, instead of the centrifuge, for immunoprecipitation.

Step 4: DNA Purification

After reversing the crosslinks and proteinase K treatment, DNA was purified using a Qiagen QIAquick® PCR Purification kit instead of the DNA-purifying slurry provided in the ChIP kit.

After purification with a QIAquick® column, each final product was eluted with a total of 60 μl Buffer EB, in two 30 μl elution steps.

The end product was quantified by fluorescence (Quant-IT™ PicoGreen® dsDNA assay kit, as per manufacturer's protocol).

qPCR

The Qiagen QuantiTect® SYBR® Green qPCR kit for ChIP-qPCR was used, following manufacturer's instructions.

25 pg template per reaction was used.

1.25 μl of each primer (5 μM) was used per reaction.

A log-5 standard curve was done using input Raji DNA (sonicated, but not subjected to ChIP). See FIG. S3A-B.

To avoid pipetting error, all samples were diluted to the same concentration as the least-concentrated sample, so the same amount could be added to every reaction. Dilutions were done serially.

All reactions in triplicate were performed.

qPCR Primers

```
ChIP-STR (BV677278 amplicon)
                                        (SEQ ID NO: 11)
Primer ChIPSTR_F:   5'-TCATGCAAAGTTCCAAAACC-3'

(SEQ ID NO: 12)
Primer ChIPSTR_R:   5'-GATTTCCTCCCTCCCTTCC-3'
```

These primers capture the entire BV677278 repeat, and generate a ~200 bp amplicon.

```
β-actin (+ control)
                                        (SEQ ID NO: 13)
Primer βAct_F:      5'-GCCCTAGGCACCAGGGTGTGA-3'

(SEQ ID NO: 14)
Primer βAct_R:      5'-ACAGGGTGCTCCTCAGGGGC-3'
```

These primers amplify a ~150 bp sequence from the actively transcribing β-actin gene.

qPCR Reaction 1. 15 minutes, 95° C.
2. 30 seconds, 95° C.
3. 30 seconds, 65° C.
Decrease 1° C. per cycle
4. 60 seconds, 72° C.
5. Plate read
6. GoTo step 2, 9 times
7. 30 seconds, 95° C.
8. 30 seconds, 56° C.
9. 60 seconds, 72° C.
10. Plate read
11. GoTo step 6, 39 times
12. 5 minutes, 72° C.
13. Melting Curve
14. ∞, 4° C.

*Quality control data for the ChIP experiment reported here are shown in FIG. S3.

Enrichment Calculations

Fold enrichment was calculated with respect to the no antibody control (a complete ChIP reaction, but with no antibody—only beads). Briefly, this was done by raising 2 to the negative power of the difference between the C(t) of an experimental condition and its respective no-antibody control: Fold Enrichment=$2^{-[C(t)Exp-C(t)NoAntibody]}$ Results Two Six-Marker Haplotypes in DCDC2 are Associated with Reduced Performance on Reading and Language Measures To determine whether DCDC2, KIAA0319, both, or neither gene is responsible for the DYX2 signal, a tagSNP panel was designed to densely cover the DYX2 locus. Haplotype-based association analysis of reading and language in a large, extensively phenotyped birth cohort: the Avon Longitudinal Study of Parents and Children (ALSPAC), was then performed (17). Analysis showed a six-marker haplotype block within DCDC2, of which two haplotypes—CGCGAG and GACGAG—associated with very poor performance on a phoneme deletion task and a composite language measure, respectively (Table 1). For this analysis, RD cases were defined as individuals scoring two or more standard deviations below the mean on the phoneme deletion task, and LI cases as individuals scoring two or more standard deviations below the mean on either of two language measures (WOLD/NWR). The phoneme deletion task measures phonological awareness, which is widely considered to be the core deficit in RD (2). The Wechsler Objective Learning Dimensions (WOLD) verbal comprehension and nonword repetition (NWR) tasks that comprise the WOLD/NWR composite language measure are used to assess deficient language skills; children with LI show consistently poor performance on these measures (18, 19) (see Table S1 and the Materials and Methods for more information on these phenotypic measures). Cases were defined this way to examine association of DYX2 variants with severe RD and LI. The two haplotypes show strong association with their respective phenotypes; the CGCGAG-RD association survived Bonferroni correction for multiple testing and the GACGAG-LI p-value was just below the threshold. However, the associations by themselves are not strong enough to rule out type I error, partly due to the low frequencies of the haplotypes and the small number of cases. Interestingly, however, the effect of these haplotypes is strong enough to reduce mean performance on relevant phenotypic measures in carriers versus non-carriers. Carriers of the CGCGAG haplotype, on average, showed significantly poorer performance on eight reading-related measures compared to non-carriers. Likewise, carriers of the GACGAG haplotype showed significantly lower average performance on the WOLD/NWR composite language measure (Table 2). This quantitative effect indicated that this finding is not a false positive and prompted further analysis. Additionally, this haplotype block resides in close proximity to BV677278, a putatively functional compound short tandem repeat (STR) Applicants reported previously (11) (FIG. 1C). The polymorphism of BV677278 derives from five discrete repeat units that vary in number (FIG. 1A, Table S4). This STR evolves rapidly, as indicated by its high degree of polymorphism among primate species and within *Homo sapiens* (FIG. 1B, FIG. S2, Table S4).

The DCDC2 Risk Haplotypes are in Strong Linkage Disequilibrium with Two Alleles of BV677278

The associated haplotype block is adjacent to BV677278 (FIG. 1C) and whether the two risk haplotypes could be capturing association arising from functional alleles of BV677278 via linkage disequilibrium was assessed. To address this question, all carriers of these haplotypes were subjected to BV677278 genotyping by Sanger sequencing. Of the carriers of the CGCGAG haplotype, 92% also carry BV677278 allele 5. Likewise, 78% of the carriers of GACGAG also carry BV677278 allele 6 (Table 1). Alleles 5 and 6 are similar in structure to each other, and cluster phylogenetically to the same clade (Table S4, FIG. S1). Indeed, nearly all carriers of these two haplotypes also carry an allele from this clade (Table 1). These results further implicate BV677278 as a RD risk variant and expand it as a possible LI risk variant (11), and together with its apparent regulatory capacity, suggest that these BV677278 alleles are responsible for the risk haplotypes' effects.

BV677278 Specifically Binds the Transcription Factor ETV6

Figure 2:
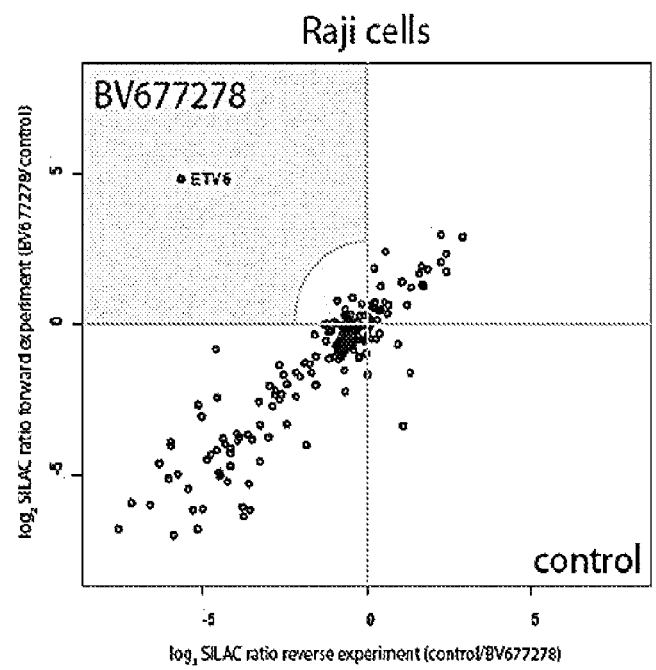
FIG. 2: (A-B) SILAC results for Raji and HeLa cells; two-dimensional interaction plot. (C) ChIP results. α-H3: antibody to a histone H3 variant enriched in actively transcribing genes. β-actin: control amplicon from the β-actin gene. Error bars represent standard deviation among 3 replicates. Double asterisk (**) represents a p-value below 0.01 (one-tailed T-test; see Table S6).
Figure 2:
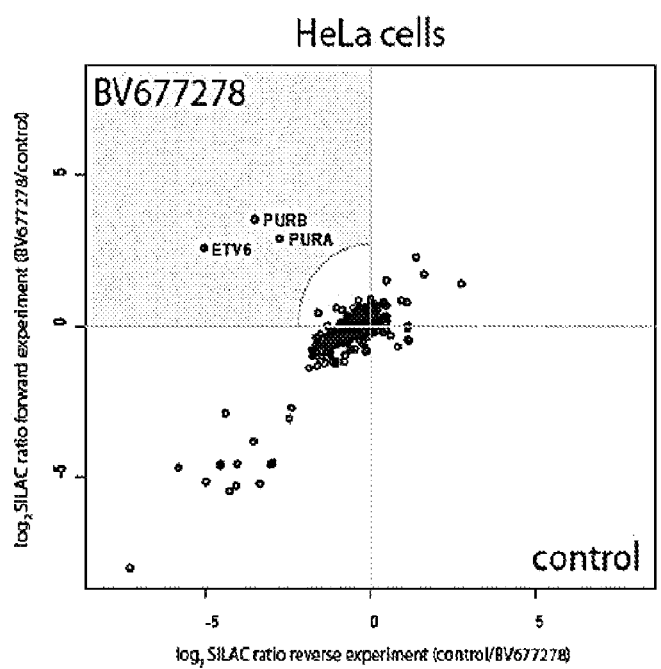
Figure 2:
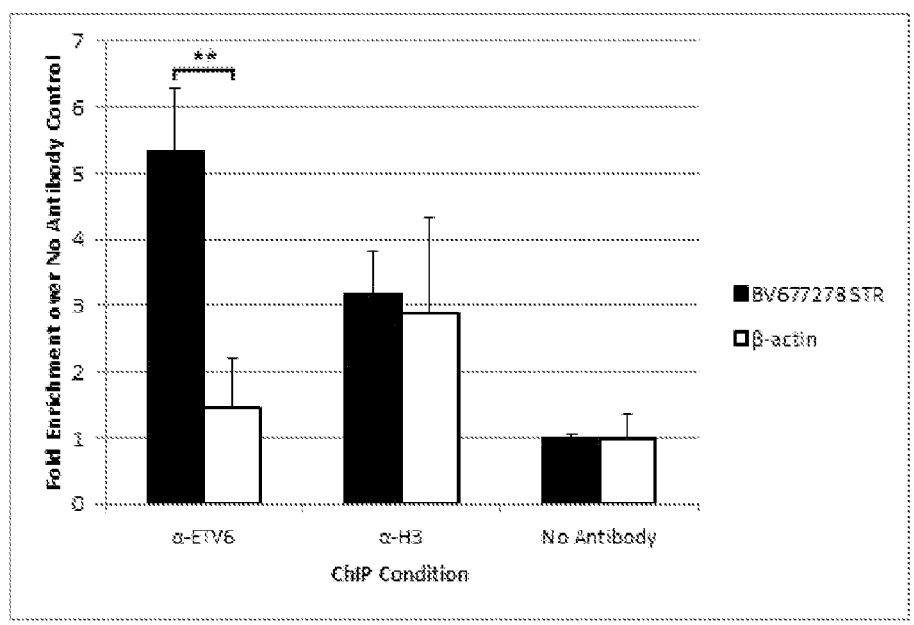

To gain mechanistic insight into the function of BV677278, quantitative mass spectrometry was used to identify the protein(s) that bind to this locus (20). To this end, a biotinylated oligonucleotide probe carrying segments of the BV677278 repeat previously shown to bind a nuclear protein, and a scrambled non-binding control, were incubated with nuclear extracts that had been SILAC-labeled (15). SILAC-labeling involves culturing two parallel populations of cells—one with media containing amino acids labeled with heavy isotopes of carbon and nitrogen, the other with naturally-occurring isotopes. After the label is incorporated, proteins from the two populations ('heavy' and 'light') can be differentiated from each other by quantitative mass spectrometry. The heavy nuclear extract was incubated with the BV677278 probe, and the light nuclear extract with the control probe. The probes were then pulled down with streptavidin-conjugated beads, and the resulting protein mixture was subjected to quantitative mass spectrometry, and proteins were looked for that were significantly enriched by pulldown with the BV677278 probe compared to the control probe (high heavy:light ratio). The experiment was conducted with nuclear extracts derived from either HeLa or Raji cells, and repeated with a label-switch resulting in a two-dimensional interaction plot. These experiments yielded a single candidate, shared by both HeLa and Raji: the transcription factor ETV6 (FIG. 2A-B). To confirm the BV677278-ETV6 interaction, chromatin immunoprecipitation with quantitative PCR was performed (ChIP-qPCR) using α-ETV6 antibody, in Raji cells. Immunoprecipitation with the α-ETV6 antibody showed marked enrichment for the BV677278 amplicon, but not for the control amplicon derived from the gene encoding β-Actin (ACTB) (FIG. 2C). These results demonstrated that ETV6 binds the BV677278 region.

The DCDC2 Risk Haplotypes Show a Synergistic Genetic Interaction with a Known RD Risk Haplotype in the gene KIAA0319

Figure 3:
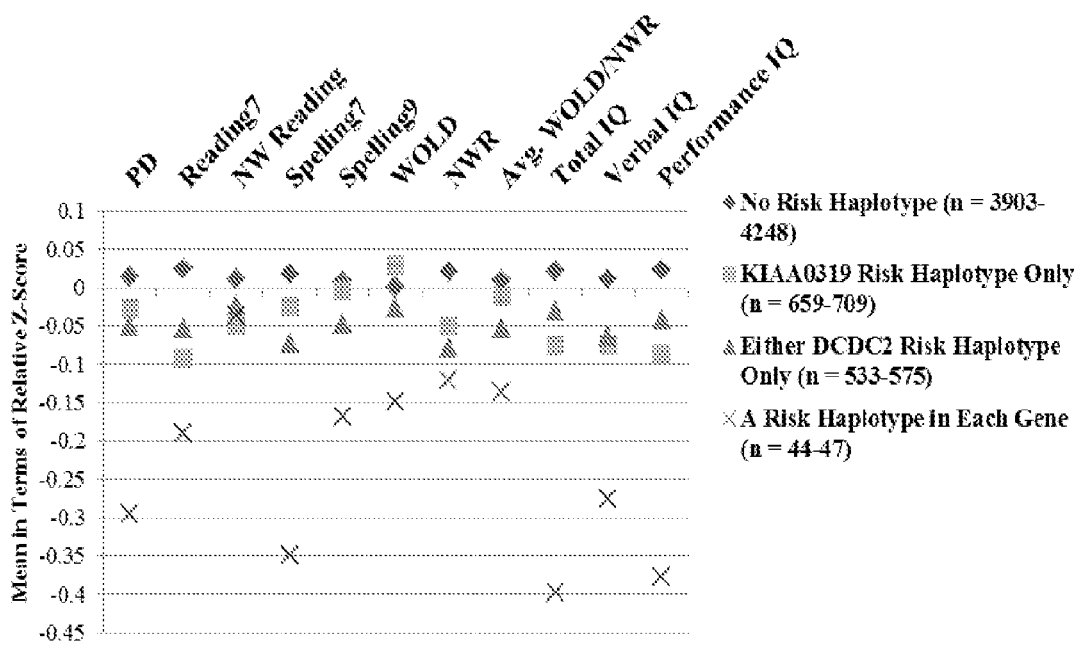
FIG. 3: (A) Effect of risk haplotype carrier status on various reading, language, and cognitive phenotypes (described in Table S1 and Materials and Methods of Examples Section). Data points represent the mean of each group, converted to a z-score relative to the mean of the ALSPAC sample population. Units of the y-axis are fractions of a standard deviation. PD: phoneme deletion task; Reading7: single-word reading at age 7; NW Reading: non-word reading at age 9; Spelling7 and 9: spelling at ages 7 and 9; WOLD: Wechsler Objective Learning Dimensions verbal comprehension task; NWR: non-word repetition task. (B) Model of differential effects of BV677278 alleles. ETV6 monomers must at least homodimerize through their pointed (PNT) domains to bind DNA through their ETS domains, and they may homopolymerize in vivo. Indels of BV677278 repeat units could change the size of the ETV6 polymer, and thus affect target gene expression.
Figure 3:
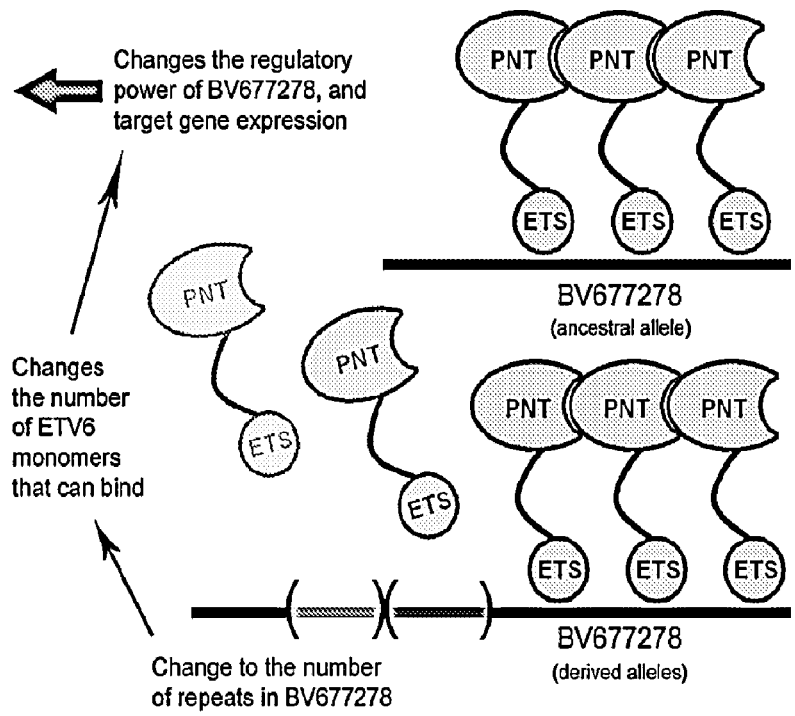

Together with Applicant's previous findings, these data implicated BV677278 as a regulatory element. Luciferase assays suggest that BV677278 is capable of modulating expression from the DCDC2 promoter, but it may regulate other genes (15). A three-marker risk haplotype encompassing the 5' half and upstream sequence of KIAA0319 has been consistently associated with lowered reading performance (21-24). Additionally, expression of KIAA0319 in human neural cell lines is reduced with this haplotype, relative to non-risk haplotypes (25). Applicants therefore questioned whether BV677278 might interact genetically with the KIAA0319 risk haplotype, and examined the effect of carrying both a DCDC2 (CGCGAG or GACGAG) and the KIAA0319 risk haplotype on several reading, language, and cognitive measures. Strikingly, subjects carrying risk haplotypes in both genes showed markedly worse mean performance (up to 0.40 standard deviations) on nearly all measures examined (FIG. 3A). This reduction in performance in carriers of both risk haplotypes is, for most of the phenotypes examined, greater than the sum of those of single carriers, indicating a synergistic interaction between these two genes. This result corroborates a previous report, which provided statistical evidence that DCDC2 and KIAA0319 interact to influence RD risk (26).

Discussion

Given the remarkable similarity of the human exome to those of other higher primates, it has been hypothesized that rapidly evolving regulatory elements are responsible for the large phenotypic differences we observe. The recently published results of the ENCODE Consortium, which showed most of the non-coding genome to be active and much of the active proportion to be regulatory, lend circumstantial support to this hypothesis (27). Here, Applicants provide evidence of just such a regulatory element affecting reading and language, two exclusively human phenotypes. BV677278 expanded rapidly from gorilla to human, though the sequence flanking it is quite conserved (FIG. 1B), and its presence, length, and sequence vary widely among primate species (FIG. S2).

This element specifically binds ETV6, a transcription factor and proto-oncogene also known as TEL (translocation ETS leukemia). The ETV6 gene forms oncogenic fusions, often with the AML1 proto-oncogene, that are frequently seen in leukemia (28). ETV6's effect on transcription is generally repressive via recruitment of a co-repressor complex (29). Monomeric ETV6 has essentially no affinity for its binding sequence; it must at least dimerize to bind DNA (30). There is evidence that ETV6 polymerizes in vivo, with the length of the polymer dependent on the number and spacing of binding sites (31). This property suggests that different alleles of BV677278 bind ETV6 polymers of different lengths, depending on the number of suitably spaced ETV6 binding sites, and that these differences change the regulatory power of the complex (FIG. 3B). Supporting this idea is the structural similarity of alleles 5 and 6: both have the same GGAA insertion in repeat unit 2, relative to the most common allele (Table S4). GGAA is the core binding sequence of ETV6 (30), and this insertion could recruit an additional ETV6 monomer to the complex.

However, whether ETV6 represses transcription in this context, and what genes it targets, are uncertain. Applicants previously reported luciferase assays appear to indicate that some BV677278 alleles activate transcription from the DCDC2 promoter, and that alleles with very different structures (e.g. 3 and 5, Table S4) activate transcription to a similar extent (15). BV677278's genetic interaction with the KIAA0319 risk haplotype, and its dramatic effect on phenotype, suggest KIAA0319 as a target gene in vivo. The KIAA0319 risk haplotype is known to be associated with reduced KIAA0319 expression, at least in human neural cell lines, suggesting the possibility that it carries a promoter or promoter-proximal variant that increases repression (or decreases activation) by BV677278, resulting in reduced gene expression and possible phenotypic consequences. That reduced IQ was also observed with the DCDC2-KIAA0319 interaction (FIG. 3A) may reflect pathology at the cellular level (e.g. disrupted neuronal migration), or it may simply reflect the importance of language in measuring IQ. BV677278 genotyping in all members of the ALSPAC and subsequent combinatorial analysis, together with chromatin conformation experiments, will further illuminate BV677278's target genes and mechanism of action.

The DCDC2 and KIAA0319 risk haplotypes have a synergistic effect on reading, language, and cognitive phenotypes. This lends credence to the 'phantom heritability' hypothesis, which explains the so-called missing heritability of continuous traits as resulting from non-additive interactions between risk variants (32). Also supporting this idea is that although carriers of the DCDC2 risk haplotypes show reduced average performance on phenotypic measures, the standard deviations for these measures were generally similar to those of non-carriers (Table 2). This implies that the magnitude of effect of the risk haplotypes on phenotype lies on a continuum, and is dependent on other, interacting risk variants, as well as environmental and stochastic factors. Additionally, these results may partially explain the missing efficacy of GWAS studies. If rapidly evolving regulatory elements are indeed substantially responsible for continuous phenotypic variation, they would be expected, like BV677278, to show a higher degree of polymorphism than the average SNP. This would make them difficult to identify by standard single-marker analyses in GWAS, reinforcing the importance of multi-marker, pathway, and gene-gene interaction analyses in the study of complex traits.

REFERENCES

1. Development NIoCHa (2010) Learning Disabilities (nichd.nih.gov/health/topics/learning_disabilities.cfm).
2. Peterson R L & Pennington B F (2012) Lancet 379 (9830):1997-2007.
3. Pennington B F & Bishop D V (2009) Annual review of psychology 60:283-306.
4. Anonymous (2007) National Assessment of Educational Progress (NAEP): The Nation's Report Card, Reading 2007 (National Center for Education Statistics, (nces.ed.gov/nationsreportcard/pubs/main2007/2007496.asp), (Institute of Education Sciences UDoE).
5. Scerri T S & Schulte-Korne G (2010) European child & adolescent psychiatry 19(3):179-197.
6. Meng H, et al. (2005) Human genetics 118(1):87-90.
7. Peschansky V J, et al. (2010) Cereb Cortex 20(4):884-897.
8. Poelmans G, et al. (2011) Molecular psychiatry 16(4): 365-382.
9. Liu J S (2011) Current neurology and neuroscience reports 11(2):171-178.
10. Velayos-Baeza A, et al. (2010) The Journal of biological chemistry 285(51):40148-40162.
11. Meng H, et al. (2005) Proceedings of the National Academy of Sciences of the United States of America 102 (47):17053-17058.
12. Ludwig K U, et al. (2008) Psychiatric genetics 18(6):310-312.
13. Marino C, et al. (2012) Psychiatric genetics 22(1): 25-30.
14. Wilcke A, et al. (2009) Annals of dyslexia 59(1):1-11.
15. Meng H, et al. (2011) Behavior genetics 41(1):58-66.
16. Cope N, et al. (2012) NeuroImage 63(1):148-156.
17. Boyd A, et al. (2012) International journal of epidemiology.
18. Bishop D V, et al. (1996) Journal of child psychology and psychiatry, and allied disciplines 37(4):391-403.
19. Newbury D F, et al. (2009) American journal of human genetics 85(2):264-272.
20. Mittler G, et al. (2009) Genome research 19(2):284-293.
21. Francks C, et al. (2004) American journal of human genetics 75(6):1046-1058.
22. Luciano M, et al. (2007) Biological psychiatry 62(7): 811-817.
23. Paracchini S, et al. (2008) The American journal of psychiatry 165(12):1576-1584.
24. Scerri T S, et al. (2011) Biological psychiatry 70(3): 237-245.
25. Paracchini S, et al. (2006) Human molecular genetics 15(10):1659-1666.
26. Harold D, et al. (2006) Molecular psychiatry 11(12): 1085-1091, 1061.
27. Djebali S, et al. (2012) Nature 489(7414):101-108.
28. Fuka G, et al. (2011) PloS one 6(10):e26348.
29. Wang L & Hiebert S W (2001) Oncogene 20(28): 3716-3725.
30. Green S M, et al. (2010) The Journal of biological chemistry 285(24):18496-18504.
31. Kim C A, et al. (2001) The EMBO journal 20(15): 4173-4182.
32. Zuk O, et al. (2012) Proceedings of the National Academy of Sciences of the United States of America 109 (4):1193-1198.
33. Han B, et al. (2008) Annals of human genetics 72(Pt 6):834-847.
34. Barrett J C, et al. (2005) Bioinformatics 21(2):263-265.
35. Purcell S, et al. (2007) American journal of human genetics 81(3):559-575.
36. Butter F, et al. (2010) EMBO reports 11(4):305-311.

SUPPLEMENTAL REFERENCES

S1. Han B, et al. (2008) Annals of human genetics 72(Pt 6):834-847.
S2. Scerri T S, et al. (2011) Biological psychiatry 70(3): 237-245.
S3. Barrett J C, et al. (2005) Bioinformatics 21(2):263-265.
S4. Purcell S, et al. (2007) American journal of human genetics 81(3):559-575.
S5. Wu K K (2006) Methods Mol Biol 338:281-290.
S6. Dignam J D, et al. (1983) Nucleic acids research 11(5):1475-1489.
S7. Mittler G, et al. (2009) Genome research 19(2):284-293.
S8. Meng H, et al. (2011) Behavior genetics 41(1):58-66.
S9. Kolodziej K E, et al. (2009) BMC molecular biology 10:6.
S10. Meng H, et al. (2005) Proceedings of the National Academy of Sciences of the United States of America 102 (47):17053-17058.
S11. Boyd A, et al. (2012) International journal of epidemiology.
S12. Hulme C, et al. (2007) Paired-associate learning, phoneme awareness, and learning to read. Journal of experimental child psychology 96(2):150-166.
S13. Peterson R L & Pennington B F (2012) Lancet 379(9830):1997-2007.
S14. Rosner J & Simon D P (1971) Journal of Learning Disabilities 4(384):40-48.
S15. Rust J, et al. (1993) WORD: Wechsler Objective Reading Dimensions Manual (Psychological Corporation, Sidcup, UK).
S16. Nunes T, et al. (2003) Scientific Studies of Reading 7(3):289-307.

S17. Neale M D (1997) *Neale Analysis of Reading Ability—Revised: Manual for Schools* (NFER-Nelson).

S18. Gathercole S E & Baddeley A D (1996) *The Children's Test of Nonword Repetition* (Psychological Corporation, London, UK).

S19. Wechsler D (1996) *Wechsler Objective Language Dimensions (WOLD)* (Psychological Corporation, London, UK).

S20. Bishop D V, et al. (1996) *Journal of child psychology and psychiatry, and allied disciplines* 37(4):391-403.

S21. Newbury D F, et al. (2009) *American journal of human genetics* 85(2):264-272.

Tables of Example 1

TABLE 1

Association and linkage disequilibrium data for DCDC2 risk haplotypes. Phenotypes are described in Table S1 and in the Materials and Methods. Cases are defined by a score of less than or equal to 2SD below the mean. P-values that survived Bonferroni correction for multiple testing ($\alpha = 0.05$) are bolded. '% Allele 5,' etc. means 'percentage of haplotype carriers with at least one copy of that allele or group of alleles.' Clade 1, the phylogenetic branch of alleles that includes 5 and 6, is described in FIG. S1.

| | | Association Data | | | | |
|---|---|---|---|---|---|---|
| Haplotype | Phenotype-2SD | n Cases | n Controls | Haplotype Freq. | Odds Ratio | P-value |
| CGCGAG | Phoneme Del. (RD) | 89 | 5225 | 0.0236 | 3.20 | 6.068 × 10⁻⁵ |
| GACGAG | WOLD/NWR (LI) | 270 | 5240 | 0.0364 | 1.91 | 2.84 × 10⁻⁴ |

| | LD Data | | | |
|---|---|---|---|---|
| Haplotype | n Carriers | % Allele 5 | % Allele 6 | % Clade 1 |
| CGCGAG | 226 | 92.0 | 7.5 | 94.3 |
| GACGAG | 392 | 12.0 | 77.6 | 91.3 |

TABLE 2

Mean performance on reading and cognitive measures in DCDC2 risk haplotype carriers vs. non-carriers. The standard deviation is shown in parentheses next to each mean. The number of subjects in each category is shown below that category. P-values are from Student's T-tests comparing the means of carriers and non-carriers of each haplotype; p-values less than 0.05 are marked with an asterisk. NWR/WOLD refers to the average z-score of performance on NWR and WOLD Verbal Comprehension tasks. Phenotypes are described in Table S1 and in the Materials and Methods.

| | CGCGAG (RD) Haplotype | | | GACGAG (LI) Haplotype | | |
|---|---|---|---|---|---|---|
| | Carriers | Non-carriers | P-value | Carriers | Non-carriers | P-value |
| Reading 7 | 27.34 (9.04) | 29.01 (8.77) | 0.005* | 29.09 (8.62) | 28.92 (8.80) | 0.728 |
| N | 232 | 4929 | | 358 | 4803 | |
| Spelling 7 | 24.38 (13.46) | 26.29 (12.33) | 0.023* | 25.56 (12.77) | 26.26 (12.36) | 0.305 |
| N | 229 | 4896 | | 355 | 4770 | |
| Phoneme | 19.30 (10.00) | 20.80 (9.17) | 0.016* | 20.61 (9.20) | 20.74 (9.21) | 0.796 |
| N | 230 | 4909 | | 357 | 4782 | |
| Reading 9 | 7.37 (2.71) | 7.73 (2.27) | 0.020* | 7.75 (2.33) | 7.72 (2.29) | 0.754 |
| N | 228 | 4914 | | 359 | 4783 | |
| NW Read 9 | 5.05 (2.58) | 5.38 (2.36) | 0.043* | 5.47 (2.36) | 5.36 (2.44) | 0.391 |
| N | 228 | 4911 | | 359 | 4780 | |
| Spelling 9 | 10.03 (2.58) | 10.50 (3.23) | 0.031* | 10.48 (3.25) | 10.48 (3.26) | 0.987 |
| N | 228 | 4904 | | 357 | 4775 | |
| Speed | 105.44 (11.76) | 106.34 (12.10) | 0.299 | 106.71 (11.77) | 106.27 (12.11) | 0.524 |
| N | 207 | 4430 | | 326 | 4311 | |
| Accuracy | 102.77 (14.00) | 105.22 (13.10) | 0.009* | 105.18 (13.24) | 105.11 (13.15) | 0.919 |
| N | 208 | 4438 | | 329 | 4317 | |
| Read Comp | 99.74 (11.67) | 101.54 (11.37) | 0.026* | 101.73 (11.82) | 101.44 (11.35) | 0.663 |
| N | 208 | 4438 | | 329 | 4317 | |
| Verbal IQ | 107.35 (15.70) | 108.97 (15.67) | 0.113 | 108.38 (15.90) | 108.94 (15.65) | 0.497 |
| N | 245 | 5334 | | 388 | 5191 | |

TABLE 2-continued

Mean performance on reading and cognitive measures in DCDC2 risk haplotype carriers vs. non-carriers. The standard deviation is shown in parentheses next to each mean. The number of subjects in each category is shown below that category. P-values are from Student's T-tests comparing the means of carriers and non-carriers of each haplotype; p-values less than 0.05 are marked with an asterisk. NWR/WOLD refers to the average z-score of performance on NWR and WOLD Verbal Comprehension tasks. Phenotypes are described in Table S1 and in the Materials and Methods.

|  | CGCGAG (RD) Haplotype | | | GACGAG (LI) Haplotype | | |
|---|---|---|---|---|---|---|
|  | Carriers | Non-carriers | P-value | Carriers | Non-carriers | P-value |
| Perf. IQ | 101.23 (14.96) | 100.28 (16.16) | 0.366 | 101.10 (15.72) | 101.19 (16.14) | 0.913 |
| N | 245 | 5334 |  | 388 | 5191 |  |
| Total IQ | 104.58 (14.22) | 106.05 (15.26) | 0.138 | 105.62 (14.95) | 106.01 (15.23) | 0.623 |
| N | 245 | 5334 |  | 388 | 5191 |  |
| NWR | 7.54 (1.94) | 7.58 (1.91) | 0.724 | 7.40 (1.91) | 7.55 (1.91) | 0.136 |
| N | 245 | 5276 |  | 384 | 5137 |  |
| WOLD | 7.11 (2.56) | 7.33 (2.44) | 0.178 | 7.12 (2.60) | 7.33 (2.43) | 0.104 |
| N | 245 | 5270 |  | 383 | 5132 |  |
| NWR/WOLD | −0.031 (0.82) | 0.00 (0.78) | 0.532 | −0.08 (0.77) | 0.01 (0.78) | 0.041* |
| N | 245 | 5281 |  | 384 | 5142 |  |

TABLE S1

(A) List of phenotypes used. A detailed description of each phenotype is given in the Materials and Methods. (B) Case/control definitions used in association analysis.

| Phenotype | Description |
|---|---|
| A. | |
| Reading at 7 | Wechsler Objective Reading Dimensions (WORD), single-word reading task, age 7 |
| Reading at 9 | Single-word reading task, age 9 |
| Phoneme Del | Auditory Analysis task, age 7 |
| Total IQ | Wechsler Intelligence Scale for Children (WISC), Total IQ, age 8 |
| Verbal IQ | WISC Verbal IQ component, age 8 |
| Performance IQ | WISC Performance IQ component, age 8 |
| WOLD | Wechsler Objective Language Dimensions (WOLD), verbal comprehension task, age 8 |
| NWR | Non-word repetition task, age 8 |
| NW Read at 9 | Non-word reading task, age 9 |
| Spelling at 7 | Single-word spelling task, age 7 |
| Spelling at 9 | Single-word spelling task, age 9 |
| Speed | Passage reading, speed, age 9 |
| Accuracy | Passage reading, accuracy of words read, age 9 |
| Reading Comp. | Passage reading, comprehension, age 9 |
| B. | |
| Phoneme Del | Cases defined as having a score less than or equal to 2 standard deviations below the mean on the phoneme deletion task |
| WOLD/NWR | Cases defined as having a score less than or equal to 2 standard deviations below the mean on either the WOLD verbal comprehension task or the non-word repetition task |

TABLE S2

Bivariate Pearson correlations among reading and language measures in ALSPAC. Phoneme = Phoneme deletion task at age 7 years; NWR = Nonword Repetition at age 8 years; WOLD = Wechsler Objective Learning Dimensions Verbal Comprehension task at age 8 years; Avg NWR WOLD = average of z-score performance on NWR and WOLD tasks; Reading 7 = Single word reading at age 7 years; Reading 9 = Single word reading at age 9; All IQ measures were collected at age 8 years with the Wechsler Intelligence Scale for Children version III.

|  | Phoneme | NWR | WOLD Comp. | Avg NWR WOLD | Reading 7 | Reading 9 | Total IQ | Verbal IQ | Perf. IQ |
|---|---|---|---|---|---|---|---|---|---|
| Phoneme | 1 | | | | | | | | |
| NWR | 0.362 | 1 | | | | | | | |
| WOLD | 0.165 | 0.214 | 1 | | | | | | |
| Avg NWR WOLD | 0.338 | 0.779 | 0.780 | 1 | | | | | |
| Reading 7 | 0.688 | 0.403 | 0.259 | 0.425 | 1 | | | | |
| Reading 9 | 0.550 | 0.351 | 0.202 | 0.355 | 0.722 | 1 | | | |
| Total IQ | 0.406 | 0.324 | 0.386 | 0.455 | 0.500 | 0.387 | 1 | | |
| Verbal IQ | 0.426 | 0.346 | 0.424 | 0.494 | 0.536 | 0.421 | 0.871 | 1 | |
| Perf. IQ | 0.246 | 0.192 | 0.216 | 0.262 | 0.292 | 0.218 | 0.819 | 0.435 | 1 |

TABLE S3

Statistics for the SNPs reported here. Statistics were calculated after exclusion of low-call-rate samples (<85% average call rate) and individuals not of European descent. SNPs in normal (not bold) font (SNPs 1-6 in table) comprise the DCDC2 risk haplotype block; SNPs in bold font (SNPs 7-9 in table) comprise the KIAA0319 risk haplotype block. SNPs are listed in the order of their respective haplotype (e.g. CGCGAG).

| SNP | Call Rate | Major Allele | Major Allele Freq. | Minor Allele | Minor Allele Freq. | HWE p-value |
|---|---|---|---|---|---|---|
| rs33914824 | 92.6% | C | 0.961 | G | 0.039 | 0.541 |
| rs807694 | 94.0% | G | 0.952 | A | 0.047 | 0.974 |
| rs707864 | 93.0% | T | 0.874 | C | 0.126 | 0.012 |
| rs10456301 | 93.5% | G | 0.929 | A | 0.071 | 0.814 |
| rs16889066 | 91.2% | A | 0.945 | G | 0.055 | 0.134 |
| rs9379651 | 86.7% | G | 0.877 | A | 0.123 | 0.720 |
| rs4504469 | 89.1% | C | 0.592 | T | 0.408 | 0.054 |
| rs2038137 | 90.0% | G | 0.630 | T | 0.370 | 0.611 |
| rs2143340 | 89.6% | A | 0.849 | G | 0.151 | 0.583 |

TABLE S4

Structures and population frequencies for all BV677278 alleles described to date. Allele frequencies for available alleles were calculated from a previous study (10). Population allele frequencies for alleles 11-22-only frequencies in DCDC2 risk haplotype carriers are available (see Table S5). 'Del' signifies the 2,445 bp microdeletion encompassing BV677278.

| Allele | Repeat unit 1 SEQ ID NOs: 15 and 16 | Repeat unit 2 | Repeat unit 3 | Repeat unit 4 | Const. Region |
|---|---|---|---|---|---|
| 1 | (GAGAGGAAGGAAA)2 (SEQ ID NO: 15) | (GGAA)7 (SEQ ID NO: 19) | (GAAA)1 | (GGAA)2 | GGAAAGAATGAA (SEQ ID NO: 28) |
| 2 | (GAGAGGAAGGAAA)1 (SEQ ID NO: 16) | (GGAA)9 (SEQ ID NO: 20) | (GAAA)0 | (GGAA)0 | GGAAAGAATGAA (SEQ ID NO: 28) |
| 3 | (GAGAGGAAGGAAA)1 (SEQ ID NO: 16) | (GGAA)6 (SEQ ID NO: 21) | (GAAA)1 | (GGAA)2 | GGAAAGAATGAA (SEQ ID NO: 28) |
| 4 | (GAGAGGAAGGAAA)2 (SEQ ID NO: 15) | (GGAA)6 (SEQ ID NO: 21) | (GAAA)1 | (GGAA)2 | GGAAAGAATGAA (SEQ ID NO: 28) |
| 5 | (GAGAGGAAGGAAA)2 (SEQ ID NO: 15) | (GGAA)8 (SEQ ID NO: 22) | (GAAA)1 | (GGAA)2 | GGAAAGAATGAA (SEQ ID NO: 28) |
| 6 | (GAGAGGAAGGAAA)2 (SEQ ID NO: 15) | (GGAA)8 (SEQ ID NO: 22) | (GAAA)1 | (GGAA)2 | GGAAAGAATGAA (SEQ ID NO: 28) |
| 7 | (GAGAGGAAGGAAA)2 (SEQ ID NO: 15) | (GGAA)8 (SEQ ID NO: 22) | (GAAA)1 | (GGAA)1 | GGAAAGAATGAA (SEQ ID NO: 28) |
| 8 | (GAGAGGAAGGAAA)2 (SEQ ID NO: 15) | (GGAA)7 (SEQ ID NO: 19) | (GAAA)0 | (GGAA)0 | GGAAAGAATGAA (SEQ ID NO: 28) |
| 9 | (GAGAGGAAGGAAA)1 (SEQ ID NO: 16) | (GGAA)7 (SEQ ID NO: 19) | (GAAA)1 | (GGAA)2 | GGAAAGAATGAA (SEQ ID NO: 28) |
| 10 | (GAGAGGAAGGAAA)2 (SEQ ID NO: 15) | (GGAA)4 (SEQ ID NO: 23) | (GAAA)1 | (GGAA)2 | GGAAAGAATGAA (SEQ ID NO: 28) |
| 11 | (GAGAGGAAGGAAA)2 (SEQ ID NO: 15) | (GGAA)7 (SEQ ID NO: 19) | (GAAA)1 | (GGAA)2 | GGAAAGAATGAA (SEQ ID NO: 28) |
| 12 | (GAGAGGAAGGAAA)1 (SEQ ID NO: 16) | (GGAA)8 (SEQ ID NO: 22) | (GAAA)1 | (GGAA)2 | GGAAAGAATGAA (SEQ ID NO: 28) |
| 13 | (GAGAGGAAGGAAA)2 (SEQ ID NO: 15) | (GGAA)9 (SEQ ID NO: 20) | (GAAA)1 | (GGAA)2 | GGAAAGAATGAA (SEQ ID NO: 28) |
| 14 | (GAGAGGAAGGAAA)2 (SEQ ID NO: 15) | (GGAA)9 (SEQ ID NO: 20) | (GAAA)1 | (GGAA)2 | GGAAAGAATGAA (SEQ ID NO: 28) |
| 15 | (GAGAGGAAGGAAA)2 (SEQ ID NO: 15) | (GGAA)5 (SEQ ID NO: 24) | (GAAA)2 | (GGAA)2 | GGAAAGAATGAA (SEQ ID NO: 28) |
| 16 | (GAGAGGAAGGAAA)2 (SEQ ID NO: 15) | (GGAA)5 (SEQ ID NO: 24) | (GAAA)1 | (GGAA)2 | GGAAAGAATGAA (SEQ ID NO: 28) |

TABLE S4-continued

Structures and population frequencies for all BV677278 alleles described to date. Allele frequencies for available alleles were calculated from a previous study (10). Population allele frequencies for alleles 11-22-only frequencies in DCDC2 risk haplotype carriers are available (see Table S5). 'Del' signifies the 2,445 bp microdeletion encompassing BV677278.

| | | | | | |
|---|---|---|---|---|---|
| 17 | (GAGAGGAAGGAAA)2 (SEQ ID NO: 15) | (GGAA)4 (SEQ ID NO: 23) | (GAAA)2 | (GGAA)2 | GGAAAGAATGAA (SEQ ID NO: 28) |
| 18 | (GAGAGGAAGGAAA)2 (SEQ ID NO: 15) | (GGAA)7 (SEQ ID NO: 19) | (GAAA)2 | (GGAA)2 | GGAAAGAATGAA (SEQ ID NO: 28) |
| 19 | (GAGAGGAAGGAAA)2 (SEQ ID NO: 15) | (GGAA)9 (SEQ ID NO: 20) | (GAAA)0 | (GGAA)0 | GGAAAGAATGAA (SEQ ID NO: 28) |
| 20 | (GAGAGGAAGGAAA)2 (SEQ ID NO: 15) | (GGAA)10 (SEQ ID NO: 25) | (GAAA)1 | (GGAA)2 | GGAAAGAATGAA (SEQ ID NO: 28) |
| 21 | (GAGAGGAAGGAAA)2 (SEQ ID NO: 15) | (GGAA)6 (SEQ ID NO: 21) | (GAAA)1 | (GGAA)2 | GGAAAGAATGAA (SEQ ID NO: 28) |
| 22 | (GAGAGGAAGGAAA)2 (SEQ ID NO: 15) | (GGAA)10 (SEQ ID NO: 25) | (GAAA)0 | (GGAA)0 | GGAAAGAATGAA (SEQ ID NO: 28) |
| 23 | (GAGAGGAAGGAAA)2 (SEQ ID NO: 15) | (GGAA)11 (SEQ ID NO: 26) | (GAAA)0 | (GGAA)0 | GGAAAGAATGAA (SEQ ID NO: 28) |
| 24 | (GAGAGGAAGGAAA)2 (SEQ ID NO: 15) | (GGAA)6 (SEQ ID NO: 21) | (GAAA)2 | (GGAA)2 | GGAAAGAATGAA (SEQ ID NO: 28) |
| 25 | (GAGAGGAAGGAAA)1 (SEQ ID NO: 16) | (GGAA)8 (SEQ ID NO: 22) | (GAAA)1 | (GGAA)2 | GGAAAGAATGAA (SEQ ID NO: 28) |
| 26 | (GAGAGGAAGGAAA)2 (SEQ ID NO: 15) | (GGAA)5 (SEQ ID NO: 24) | (GAAA)1 | (GGAA)2 | GGAAAGAATGAA (SEQ ID NO: 28) |
| 27 | (GAGAGGAAGGAAA)1 (SEQ ID NO: 16) | (GGAA)5 (SEQ ID NO: 24) | (GAAA)1 | (GGAA)2 | GGAAAGAATGAA (SEQ ID NO: 28) |
| 28 | (GAGAGGAAGGAAA)2 (SEQ ID NO: 15) | (GGAA)7 (SEQ ID NO: 19) | (GAAA)1 | (GGAA)2 | GGAAAGAATGAA (SEQ ID NO: 28) |
| 29 | (GAGAGGAAGGAAA)2 (SEQ ID NO: 15) | (GGAA)5 +(GGGA)1 +(GGAA)1 (SEQ ID NO: 27) | (GAAA)1 | (GGAA)2 | GGAAAGAATGAA (SEQ ID NO: 28) |
| 30 | (GAGAGGAAGGAAA)2 (SEQ ID NO: 15) | (GGAA)5 (SEQ ID NO: 24) | (GAAA)1 | (GGAA)4 (SEQ ID NO: 23) | GGAAAGAATGAA (SEQ ID NO: 28) |
| 31 | (GAGAGGAAGGAAA)2 (SEQ ID NO: 15) | (GGAA)7 (SEQ ID NO: 19) | (GAAA)1 | (GGAA)1 +(GGGA)1 | GGAAAGAATGAA (SEQ ID NO: 28) |
| 32 | (GAGAGGAAGGAAA)2 (SEQ ID NO: 15) | (GGAA)8 (SEQ ID NO: 22) | (GAAA)0 | (GGAA)0 | GGAAAGAATGAA (SEQ ID NO: 28) |
| 33 | (GAGAGGAAGGAAA)2 (SEQ ID NO: 15) | (GGAA)6 (SEQ ID NO: 21) | (GAAA)0 | (GGAA)0 | GGAAAGAATGAA (SEQ ID NO: 28) |
| 34 | (GAGAGGAAGGAAA)2 (SEQ ID NO: 15) | (GGAA)7 (SEQ ID NO: 19) | (GAAA)2 | (GGAA)2 | GGAAAGAATGAA (SEQ ID NO: 28) |
| 35 | (GAGAGGAAGGAAA)1 +(GAGAGGAAGAAAA)1 (SEQ ID NO: 17) | (GGAA)7 (SEQ ID NO: 19) | (GAAA)1 | (GGAA)2 | GGAAAGAATGAA (SEQ ID NO: 28) |
| 36 | (GAGAGGAAGGAAA)1 +(GAGAGGAAGGAAA)1 (SEQ ID NO: 18) | (GGAA)9 (SEQ ID NO: 20) | (GAAA)1 | (GGAA)2 | GGAAAGAATGAA (SEQ ID NO: 28) |

TABLE S4-continued

Structures and population frequencies for all BV677278 alleles described to date. Allele frequencies for available alleles were calculated from a previous study (10). Population allele frequencies for alleles 11-22-only frequencies in DCDC2 risk haplotype carriers are available (see Table S5). 'Del' signifies the 2,445 bp microdeletion encompassing BV677278.

| | | | | | |
|---|---|---|---|---|---|
| 37 | (GAGAGGAAGGAAA)2 (SEQ ID NO: 15) | (GGAA)6 (SEQ ID NO: 21) | (GAAA)1 | (GGAA)2 | GGAAAGAATGAA (SEQ ID NO: 28) |
| 38 | (GAGAGGAAGGAAA)1 (SEQ ID NO: 16) | (GGAA)10 | (GAAA)0 | (GGAA)0 | GGAAAGAATGAA (SEQ ID NO: 28) |
| 39/Delx | x | x | x | x | x |

| Allele | Repeat unit 5 | Const. Region | Allele Freq* | Allele Freq** | Length |
|---|---|---|---|---|---|
| 1 | (GGAA)4 (SEQ ID NO: 23) | (GGGA)2 | 0.624 | 0.5536 | 102 |
| 2 | (GGAA)4 (SEQ ID NO: 23) | (GGGA)2 | 0.003 | 0.0143 | 85 |
| 3 | (GGAA)4 (SEQ ID NO: 23) | (GGGA)2 | 0.060 | 0.0464 | 85 |
| 4 | (GGAA)4 (SEQ ID NO: 23) | (GGGA)2 | 0.106 | 0.1429 | 98 |
| 5 | (GGAA)4 (SEQ ID NO: 23) | (GGGA)2 | 0.028 | 0.0143 | 106 |
| 6 | (GGAA)3 (SEQ ID NO: 29) | (GGGA)2 | 0.039 | 0.0571 | 102 |
| 7 | (GGAA)4 (SEQ ID NO: 23) | (GGGA)2 | 0.003 | 0 | 102 |
| 8 | (GGAA)4 (SEQ ID NO: 23) | (GGGA)2 | 0.003 | 0 | 90 |
| 9 | (GGAA)4 (SEQ ID NO: 23) | (GGGA)2 | 0.005 | 0.0179 | 89 |
| 10 | (GGAA)4 (SEQ ID NO: 23) | (GGGA)2 | 0.044 | 0.0286 | 90 |
| 11 | (GGAA)3 (SEQ ID NO: 29) | (GGGA)2 | N/A | 0 | 98 |
| 12 | (GGAA)3 (SEQ ID NO: 29) | (GGGA)2 | N/A | 0.0036 | 89 |
| 13 | (GGAA)3 (SEQ ID NO: 29) | (GGGA)2 | N/A | 0.0071 | 106 |
| 14 | (GGAA)4 (SEQ ID NO: 23) | (GGGA)2 | N/A | N/A | 110 |
| 15 | (GGAA)4 (SEQ ID NO: 23) | (GGGA)2 | N/A | N/A | 98 |
| 16 | (GGAA)4 (SEQ ID NO: 23) | (GGGA)2 | N/A | N/A | 94*Coriell AfA Plate Only |
| 17 | (GGAA)4 (SEQ ID NO: 23) | (GGGA)2 | N/A | N/A | 94*Coriell AfA Plate Only |
| 18 | (GGAA)4 (SEQ ID NO: 23) | (GGGA)2 | N/A | N/A | 106*Coriell AfA Plate Only |
| 19 | (GGAA)4 (SEQ ID NO: 23) | (GGGA)2 | N/A | N/A | 98 |
| 20 | (GGAA)4 (SEQ ID NO: 23) | (GGGA)2 | N/A | N/A | 114 |
| 21 | (GGAA)3 (SEQ ID NO: 29) | (GGGA)2 | N/A | N/A | 94 |
| 22 | (GGAA)4 (SEQ ID NO: 23) | (GGGA)2 | N/A | N/A | 102 |
| 23 | (GGAA)4 (SEQ ID NO: 23) | (GGGA)2 | N/A | N/A | 106 |
| 24 | (GGAA)4 (SEQ ID NO: 23) | (GGGA)2 | N/A | N/A | 102 |
| 25 | (GGAA)4 (SEQ ID NO: 23) | (GGGA)2 | N/A | N/A | 93 |
| 26 | (GGAA)3 (SEQ ID NO: 29) | (GGGA)2 | N/A | N/A | 90 |
| 27 | (GGAA)4 (SEQ ID NO: 23) | (GGGA)2 | N/A | N/A | 81 |
| 28 | (GGAA)5 (SEQ ID NO: 24) | (GGGA)2 | N/A | N/A | 106 |
| 29 | (GGAA)4 (SEQ ID NO: 23) | (GGGA)2 | N/A | N/A | 102 |
| 30 | (GGAA)4 (SEQ ID NO: 23) | (GGGA)2 | N/A | N/A | 102 |
| 31 | (GGAA)4 (SEQ ID NO: 23) | (GGGA)2 | N/A | N/A | 102 |

TABLE S4-continued

Structures and population frequencies for all BV677278 alleles described to date. Allele frequencies for available alleles were calculated from a previous study (10). Population allele frequencies for alleles 11-22-only frequencies in DCDC2 risk haplotype carriers are available (see Table S5). 'Del' signifies the 2,445 bp microdeletion encompassing BV677278.

| 32 | (GGAA)4<br>(SEQ ID NO: 23) | (GGGA)2 | N/A | N/A | 94 |
|---|---|---|---|---|---|
| 33 | (GGAA)3<br>(SEQ ID NO: 29) | (GGGA)2 | N/A | N/A | 82 |
| 34 | (GGAA)3<br>(SEQ ID NO: 29) | (GGGA)2 | N/A | N/A | 102 |
| 35 | (GGAA)4<br>(SEQ ID NO: 23) | (GGGA)2 | N/A | N/A | 102 |
| 36 | (GGAA)4<br>(SEQ ID NO: 23) | (GGGA)2 | N/A | N/A | 109 |
| 37 | (GGAA)1<br>+(GAAA)1<br>+(GGAA)2<br>(SEQ ID NO: 30) | (GGGA)2 | N/A | N/A | 98 |
| 38 | (GGAA)4<br>(SEQ ID NO: 23) | (GGGA)2 | N/A | N/A | 89 |
| 39/Delx | x | x | 0.085 | 0.1143 | |

*Frequency among parents of the Colorado Learning Disability Research Center families.

---

Sequences of alleles 1-39 from Table S4 of Example 1

Allele 1 (SEQ ID NO: 31)
GAGAGGAAGGAAAGAGAGGAAGGAAAGGAAGGAAGGAAGGAAGGAAGGAAGGAAGAAAGGAAGG
AAGGAAAGAATGAAGGAAGGAAGGAAGGAAGGGAGGGA Allele 2 (SEQ ID NO: 32)
GAGAGGAAGGAAAGGAAGGAAGGAAGGAAGGAAGGAAGGAAGGAAGGAAGGAAAGAATGAAGGA
AGGAAGGAAGGAAGGGAGGGA Allele 3 (SEQ ID NO: 33)
GAGAGGAAGGAAAGGAAGGAAGGAAGGAAGGAAGAAAGGAAGGAAGGAAAGAATGAAGGA
AGGAAGGAAGGAAGGGAGGGA Allele 4 (SEQ ID NO: 34)
GAGAGGAAGGAAAGAGAGGAAGGAAAGGAAGGAAGGAAGGAAGGAAGGAAGAAAGGAAGGAAGG
AAAGAATGAAGGAAGGAAGGAAGGAAGGGAGGGA Allele 5 (SEQ ID NO: 35)
GAGAGGAAGGAAAGAGAGGAAGGAAAGGAAGGAAGGAAGGAAGGAAGGAAGGAAGGAAGAAAGG
AAGGAAGGAAAGAATGAAGGAAGGAAGGAAGGAAGGGAGGGA Allele 6 (SEQ ID NO: 36)
GAGAGGAAGGAAAGAGAGGAAGGAAAGGAAGGAAGGAAGGAAGGAAGGAAGGAAGAAAGG
AAGGAAGGAAAGAATGAAGGAAGGAAGGAAGGGAGGGA Allele 7 (SEQ ID NO: 37)
GAGAGGAAGGAAAGAGAGGAAGGAAAGGAAGGAAGGAAGGAAGGAAGGAAGGAAGAAAGG
AAGGAAAGAATGAAGGAAGGAAGGAAGGAAGGGAGGGA Allele 8 (SEQ ID NO: 38)
GAGAGGAAGGAAAGAGAGGAAGGAAAGGAAGGAAGGAAGGAAGGAAGGAAGGAAGGAAAGAATG
AAGGAAGGAAGGAAGGAAGGGAGGGA Allele 9 (SEQ ID NO: 39)
GAGAGGAAGGAAAGGAAGGAAGGAAGGAAGGAAGGAAGAAAGGAAGGAAGGAAAGAATGA
AGGAAGGAAGGAAGGAAGGGAGGGA Allele 10 (SEQ ID NO: 40)
GAGAGGAAGGAAAGAGAGGAAGGAAAGGAAGGAAGGAAGGAAGAAAGGAAGGAAGGAAAGAATG
AAGGAAGGAAGGAAGGAAGGGAGGGA Allele 11 (SEQ ID NO: 41)
GAGAGGAAGGAAAGAGAGGAAGGAAAGGAAGGAAGGAAGGAAGGAAGGAAGGAAGAAAGGAAGG
AAGGAAAGAATGAAGGAAGGAAGGAAGGGAGGGA Allele 12 (SEQ ID NO: 42)
GAGAGGAAGGAAAGGAAGGAAGGAAGGAAGGAAGGAAGGAAGGAAGAAAGGAAGGAAGGAAAGA
ATGAAGGAAGGAAGGAAGGGAGGGA -continued Sequences of alleles 1-39 from Table S4 of Example 1

Allele 13 (SEQ ID NO: 43)
GAGAGGAAGGAAAGAGAGGAAGGAAAGGAAGGAAGGAAGGAAGGAAGGAAGGAAGGAAGA
AAGGAAGGAAGGAAAGAATGAAGGAAGGAAGGAAGGGAGGGA Allele 14 (SEQ ID NO: 44)
GAGAGGAAGGAAAGAGAGGAAGGAAAGGAAGGAAGGAAGGAAGGAAGGAAGGAAGGAAGA
AAGGAAGGAAGGAAAGAATGAAGGAAGGAAGGAAGGAAGGGAGGGA Allele 15 (SEQ ID NO: 45)
GAGAGGAAGGAAAGAGAGGAAGGAAAGGAAGGAAGGAAGGAAGGAAGGAAGAAAGAAAGGAAGGAAGG
AAAGAATGAAGGAAGGAAGGAAGGAAGGGAGGGA Allele 16 (SEQ ID NO: 46)
GAGAGGAAGGAAAGAGAGGAAGGAAAGGAAGGAAGGAAGGAAGGAAGAAAGGAAGGAAGGAAAG
AATGAAGGAAGGAAGGAAGGAAGGGAGGGA Allele 17 (SEQ ID NO: 47)
GAGAGGAAGGAAAGAGAGGAAGGAAAGGAAGGAAGGAAGGAAGAAAGAAAGGAAGGAAGGAAAG
AATGAAGGAAGGAAGGAAGGAAGGGAGGGA Allele 18 (SEQ ID NO: 48)
GAGAGGAAGGAAAGAGAGGAAGGAAAGGAAGGAAGGAAGGAAGGAAGGAAGGAAGAAAGAAAGG
AAGGAAGGAAAGAATGAAGGAAGGAAGGAAGGAAGGGAGGGA Allele 19 (SEQ ID NO: 49)
GAGAGGAAGGAAAGAGAGGAAGGAAAGGAAGGAAGGAAGGAAGGAAGGAAGGAAGGAAGG
AAAGAATGAAGGAAGGAAGGAAGGAAGGGAGGGA Allele 20 (SEQ ID NO: 50)
GAGAGGAAGGAAAGAGAGGAAGGAAAGGAAGGAAGGAAGGAAGGAAGGAAGGAAGGAAGG
AAGAAAGGAAGGAAGGAAAGAATGAAGGAAGGAAGGAAGGAAGGGAGGGA Allele 21 (SEQ ID NO: 51)
GAGAGGAAGGAAAGAGAGGAAGGAAAGGAAGGAAGGAAGGAAGGAAGGAAGAAAGGAAGGAAGG
AAAGAATGAAGGAAGGAAGGAAGGGAGGGA Allele 22 (SEQ ID NO: 52)
GAGAGGAAGGAAAGAGAGGAAGGAAAGGAAGGAAGGAAGGAAGGAAGGAAGGAAGGAAGG
AAGGAAAGAATGAAGGAAGGAAGGAAGGAAGGGAGGGA Allele 23 (SEQ ID NO: 53)
GAGAGGAAGGAAAGAGAGGAAGGAAAGGAAGGAAGGAAGGAAGGAAGGAAGGAAGGAAGG
AAGGAAGGAAAGAATGAAGGAAGGAAGGAAGGAAGGGAGGGA Allele 24 (SEQ ID NO: 54)
GAGAGGAAGGAAAGAGAGGAAGGAAAGGAAGGAAGGAAGGAAGGAAGGAAGAAAGAAAGGAAGG
AAGGAAAGAATGAAGGAAGGAAGGAAGGAAGGGAGGGA Allele 25 (SEQ ID NO: 55)
GAGAGGAAGGAAAGGAAGGAAGGAAGGAAGGAAGGAAGGAAGGAAGAAAGGAAGGAAGGAAAGA
ATGAAGGAAGGAAGGAAGGAAGGGAGGGA Allele 26 (SEQ ID NO: 56)
GAGAGGAAGGAAAGAGAGGAAGGAAAGGAAGGAAGGAAGGAAGAAAGGAAGGAAGGAAAG
AATGAAGGAAGGAAGGAAGGGAGGGA Allele 27 (SEQ ID NO: 57)
GAGAGGAAGGAAAGGAAGGAAGGAAGGAAGGAAGAAAGGAAGGAAGGAAAGAATGAAGGAAGGA
AGGAAGGAAGGGAGGGA Allele 28 (SEQ ID NO: 58)
GAGAGGAAGGAAAGAGAGGAAGGAAAGGAAGGAAGGAAGGAAGGAAGGAAGGAAGAAAGGAAGG
AAGGAAAGAATGAAGGAAGGAAGGAAGGAAGGAAGGGAGGGA Allele 29 (SEQ ID NO: 59)
GAGAGGAAGGAAAGAGAGGAAGGAAAGGAAGGAAGGAAGGAAGGAAGGGAGGAAGAAAGGAAGG
AAGGAAAGAATGAAGGAAGGAAGGAAGGAAGGGAGGGA Allele 30 (SEQ ID NO: 60)
GAGAGGAAGGAAAGAGAGGAAGGAAAGGAAGGAAGGAAGGAAGGAAGAAAGGAAGGAAGGAAGG
AAGGAAAGAATGAAGGAAGGAAGGAAGGAAGGGAGGGA Allele 31 (SEQ ID NO: 61)
GAGAGGAAGGAAAGAGAGGAAGGAAAGGAAGGAAGGAAGGAAGGAAGGAAGGAAGAAAGGAAGG
GAGGAAAGAATGAAGGAAGGAAGGAAGGAAGGGAGGGA Sequences of alleles 1-39 from Table S4 of Example 1

Allele 32 (SEQ ID NO: 62)
GAGAGGAAGGAAAGAGAGGAAGGAAAGGAAGGAAGGAAGGAAGGAAGGAAGGAAGGAAGGAAAG
AATGAAGGAAGGAAGGAAGGAAGGGAGGGA Allele 33 (SEQ ID NO: 63)
GAGAGGAAGGAAAGAGAGGAAGGAAAGGAAGGAAGGAAGGAAGGAAGGAAGGAAAGAATGAAGG
AAGGAAGGAAGGGAGGGA Allele 34 (SEQ ID NO: 64)
GAGAGGAAGGAAAGAGAGGAAGGAAAGGAAGGAAGGAAGGAAGGAAGGAAGGAAGAAAGAAAGG
AAGGAAGGAAAGAATGAAGGAAGGAAGGAAGGGAGGGA Allele 35 (SEQ ID NO: 65)
GAGAGGAAGGAAAGAGAGGAAGAAAGGAAGGAAGGAAGGAAGGAAGGAAGGAAGAAAGGAAGG
AAGGAAAGAATGAAGGAAGGAAGGAAGGAAGGGAGGGA Allele 36 (SEQ ID NO: 66)
GAGAGGAAGGAAAGAGAGGAAGGAAGGAAGGAAGGAAGGAAGGAAGGAAGGAAGGAAGGAAGAA
AGGAAGGAAGGAAAGAATGAAGGAAGGAAGGAAGGAAGGGAGGGA Allele 37 (SEQ ID NO: 67)
GAGAGGAAGGAAAGAGAGGAAGGAAAGGAAGGAAGGAAGGAAGGAAGGAAGAAAGGAAGGAAGG
AAAGAATGAAGGAAGAAAGGAAGGAAGGGAGGGA Allele 38 (SEQ ID NO: 68)
GAGAGGAAGGAAAGGAAGGAAGGAAGGAAGGAAGGAAGGAAGGAAGGAAGGAAGGAAAGAATGA
AGGAAGGAAGGAAGGGAGGGA

TABLE S5

BV677278 allele frequencies in carriers of the CGCGAG and GACGAG haplotypes in the ALSPAC. Alleles belonging to Clade 1 are demarcated with a "1" in parentheses.

| Allele | BV677278 Allele Frequency, CGCGAG | BV677278 Allele Frequency, GACGAG |
|---|---|---|
| 1 | 0.323 | 0.367 |
| 2 | 0 | 0 |
| 3 | 0.024 | 0.029 |
| 4 | 0.055 | 0.048 |
| 5(1) | 0.473 | 0.061 |
| 6(1) | 0.038 | 0.393 |
| 7 | 0 | 0 |
| 8 | 0 | 0.001 |
| 9 | 0.002 | 0.004 |
| 10 | 0.027 | 0.022 |
| 11(1) | 0 | 0.008 |
| 12(1) | 0 | 0 |
| 13(1) | 0 | 0.009 |
| 14(1) | 0.007 | 0.009 |
| 15 | 0.002 | 0 |
| 16 | 0 | 0 |
| 17 | 0 | 0 |
| 18 | 0 | 0.001 |
| 19 | 0 | 0 |
| 20(1) | 0 | 0.005 |
| 21(1) | 0 | 0.003 |
| 22 | 0 | 0.001 |
| Del | 0.049 | 0.037 |

TABLE S6

P-values for ChIP-qPCR experiment (FIG. 2B). Values represent one-tailed paired T-tests for fold enrichment between each pair of ChIP conditions specified (three replicates each). STR: BV677278 STR amplicon; β-Actin: control amplicon from the β-actin gene; α-ETV6: ChIP with anti-ETV6 antibody; α-H3: ChIP with anti-variant histone H3 control antibody; NA: no-antibody control ChIP. P-values below 0.05 are shown in bold with an asterisk, p-values below 0.01 have two asterisks.

|  | α-ETV6, STR | α-ETV6, β-Actin | NA, STR | α-H3, STR | α-H3, β-Actin | NA, β-Actin |
|---|---|---|---|---|---|---|
| α-ETV6, STR | X | 0.00728\*\* | 0.01114\* | 0.07659 | 0.06967 | 0.01005\* |
| α-ETV6, β-Actin |  | X | 0.19296 | 0.05375 | 0.05228 | 0.11426 |
| NA, STR |  |  | X | 0.02079\* | 0.08653 | 0.42981 |
| α-H3, STR |  |  |  | X | 0.46893 | 0.01133\* |
| α-H3, β-Actin |  |  |  |  | X | 0.05509 |
| NA, β-Actin |  |  |  |  |  | X |

TABLE S7

One-way ANOVA between groups listed in FIG. 3A—carriers of
1) no risk haplotype, 2) the KIAA0319 risk haplotype, 3) either DCDC2
haplotype, and 4) a risk haplotype in both genes.

| Phenotype (Z-transformed) | ANOVA P-Value |
|---|---|
| Phoneme Deletion | 0.088 |
| Total IQ | 0.003 |
| Verbal IQ | 0.006 |
| Performance IQ | 0.043 |
| Verbal Comprehension (WOLD) | 0.562 |
| Nonword Repetition | 0.053 |
| Avg WOLD and NWR | 0.179 |

Example 2

Having established the association between DCDC2 risk haplotypes and KIAA0319 risk haplotypes, the relationship of READ1 (a functional RD/LI risk variant within DCDC2), and the KIAA0319 RD risk variant KIAHap (a haplotype covering the 5' half of the RD risk gene KIAA0319 and some of its upstream sequence and neighboring gene TDP2) was investigated. As described herein, READ1 is comprised of five discrete repeat units, each of which varies in number, giving rise to considerable polymorphism. Including the deletion, 39 READ 1 alleles have been described thus far, 6 of which are common, and 32 of which are rare (in individuals of European ancestry). These alleles vary in length from 81 bp to 114 bp. READ 1 does not appear to exist outside of the higher primates, and among higher primate species (and within Homo sapiens) its length is highly variable. It appears as though READ1 is a hypermutable, rapidly-evolving element that first appeared in primates and reached its full size in Homo sapiens (Powers et al., 2013).

To determine the effects of individual READ1 alleles in vivo, the association of READ 1 with reading and language was examined in the Avon Longitudinal Study of Parents and Children (ALSPAC), a large longitudinal birth cohort. Allele 5 of READ 1 was strongly associated with Severe RD, while allele 6 of READ1 was strongly associated with Severe LI (Table 1). Furthermore, those individuals who carried at least one copy of allele 5 performed worse on six different reading-related measures, on average, compared to non-carriers of allele 5 ($p<0.05$), while carriers of allele 6 performed worse on a composite language measure, on average, than non-carriers of allele 6 ($p<0.05$). These two relatively common alleles (allele frequencies of 3.6% and 5.0%, respectively) are structurally similar to each other, and cluster to the same clade phylogenetically. Compared to the most common allele (allele 1) both alleles have a GGAA insertion in the same position. By contrast, other common READ1 alleles appeared to have a protective effect on reading and language. Carriers of at least one copy of a shorter READ1 allele (an allele with only one iteration of repeat unit 1 or RU1, as opposed to two iterations in the majority of READ1 alleles) performed better on reading and language tasks relative to non-carriers, although the protective associations with Severe RD and LI were only suggestive (Table 1 of Example 2, below).

TABLE 1

Association results for READ1. This table shows the results of association
with READ1 single and compound alleles with Severe RD and Severe LI.
Associations were computed under an allelic model. Significant p-values
are bolded, and notable odds ratios for increased (#) and
reduced (*) risk are shown.

| Allele | Description | READ1 Alleles | MAF (ALSPAC) | P-Value, Severe RD | OR, Severe Rd | P-Value, Severe LI | OR, Severe LI |
|---|---|---|---|---|---|---|---|
| 3 | 3 only, protective | 3 | 0.0463 | 0.179 | 0.575* | 0.255 | 0.77 |
| 4 | 4 only | 4 | 0.0924 | 0.239 | 1.28 | 0.141 | 0.78 |
| 5 | 5 only, deleterious | 5 | 0.0355 | 0.000058 | 2.37# | 0.487 | 0.84 |
| 6 | 6 only, deleterious | 6 | 0.0496 | 0.0995 | 1.53# | 0.00595 | 1.65 |
| 10 | 10 only | 7 | 0.0502 | 0.795 | 0.919 | 0.603 | 0.9 |
| 5 + 6 | Major deleterious alleles | 5, 6 | 0.0851 | 0.000037 | 1.96# | 0.000074 | 1.73 |
| Shorter Alleles | Only one copy of RU1; major protective alleles | 2, 3, 9, 12, 25, 27, 38 | 0.0521 | 0.0957 | 0.506* | 0.292 | 0.8 |

As described herein, the READ1-binding protein was identified as the potent transcriptional repressor ETV6, whose binding sequence (GGAA) matches the insertion seen in risk alleles 5 and 6. This suggests that alleles 5 and 6 have more ETV6 binding sites available than neutral or protective alleles (particularly the protective shorter alleles). When the properties of ETV6 are considered, the peculiar behavior of READ1 alleles begins to make sense. In its monomeric state, ETV6 is incapable of binding DNA. It must at least homodimerize to displace an autoinhibitory domain blocking its DNA-binding domain in the monomeric state (Green et al., 2010), and is known to be capable of homopolymerization (Tognon et al., 2004). This property suggests an intriguing possibility—that READ1 alleles of different lengths bind different numbers of ETV6 monomers, and this alters the regulatory power of the complex (FIG. 3B).

Figure 5:
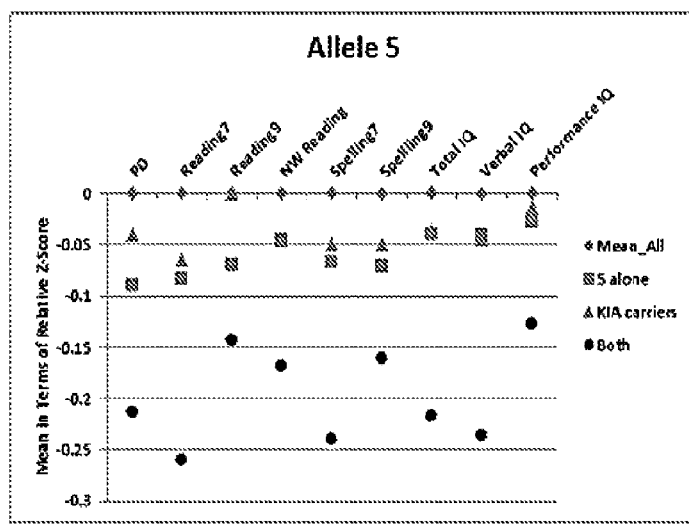
FIG. 5: Epistasis of READ1 over KIAA0319 Risk Haplotype. (A) This plot shows the effect of having at least one copy of the denoted READ1 allele alone (e.g., allele 5), at least one copy of KIAHap alone, and at least one copy of each (both), compared to all members of the ALSPAC. (B) This plot shows the protective effects of having a READ1 allele comprising a single copy of Repeat Unit 1 (RU1_1). Data points represent the z-transformed mean of each group, compared to the mean of the entire ALSPAC (Mean_All), on the indicated measures. Units of the y-axis are fractions of a standard deviation. Verbal, Performance, and Total IQ were measured at age 8 by the WISC-III. PD: phoneme deletion task at age 7; Reading 7: single-word reading task at age 7; Reading 9: single-word reading task at age 9; NW Reading: single non-word reading task at age 9, Spelling 7: spelling task at age 7; Spelling 9: spelling task at age 9.
Figure 5:
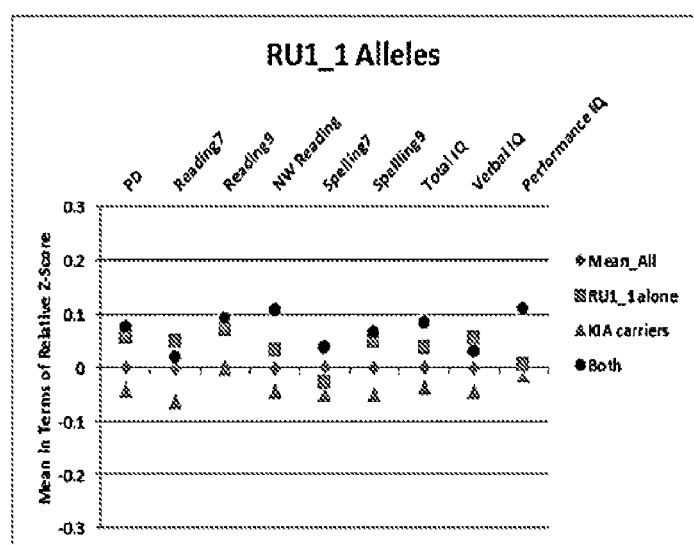

Likewise, KIAHap is thought to tag a functional promoter or promoter-proximal variant that alters KIAA0319 gene regulation. There is evidence that this functional variant is the SNP rs9461045. This SNP is in linkage disequilibrium with KIAHap and is associated with reduced reporter gene expression from the KIAA0319 promoter in both neuronal and non-neuronal cell lines (Dennis et al., 2009; Paracchini et al., 2006). The regulatory nature of KIAHap and the fact that READ1 appears to be an ETV6-binding regulatory element led to the question of whether READ1 risk alleles 5 and 6 interact with KIAHap to affect phenotype. Strikingly, carriers of both a READ 1 risk allele and KIAHap showed markedly worse performance in reading, language, and IQ tasks (FIG. 5A shows allele 5). This interaction is generally synergistic; that is, the effect of having two risk alleles is greater than the sum of the alleles' individual effects (FIG. 5A). Additionally, the protective, shorter alleles of READ1 (e.g., those comprising a single repeat unit 1, "RU1_1") appear to interact epistatically with KIAHap. In individuals with at least one copy of a shorter, RU1_1 allele of READ1, the deleterious effect of KIAHap is completely negated—mean performance of subjects with both an RU1_1 allele and KIAHap is generally slightly above the population average and resembles that of subjects with an RU1_1 allele alone (FIG. 5B). Therefore, it appears that KIAHap synergizes with deleterious READ 1 alleles to exacerbate their individual deleterious effects on reading and language, but is epistatically masked by protective READ 1 alleles. This suggests that ETV6 and READ1 form a regulatory complex that epistatically regulates KIAA0319, and possibly DCDC2 and other target genes.

Example 3

Figure 6:
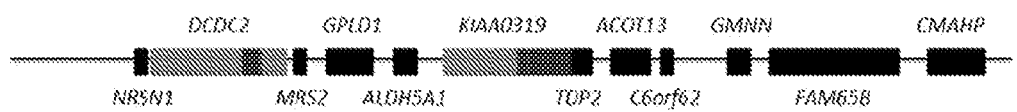
FIG. 6: (A) Schematic of the genes within the DYX2 locus on chromosome 6p21.3. Genes in light grey, DCDC2 and KIAA0319, have replicated associations with written and verbal language phenotypes, namely RD and LI. Regions in dark grey within the genes denote two functional variants, READ1 in DCDC2 and a risk haplotype with markers in KIAA0319 and TDP2, which have been functionally associated with RD and LI using animal models and molecular techniques. (B) An updated schematic of genes with markers that show replicated associations to RD, LI, and/or IQ. The genes (shown in light grey) have expanded to seven (DCDC2, KIAA0319, TDP2, ACOT13, C6orf62, FAM65B, and CMAHP), although linkage disequilibrium may account for multiple associations (particularly for KIAA0319, TDP2, ACOT13, and C6orf62).
Figure 6:
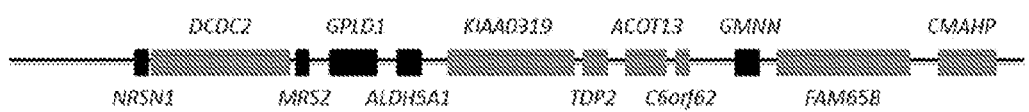

Characterization of the DYX2 Locus on Chromosome 6p22 with Reading Disability, Language Impairment, and Overall Cognition Introduction Described here is assessment of the relationship of the DYX2 locus with RD, LI, and cognition. A marker panel densely covering the 1.4Mb DYX2 locus was developed and used to assess the association with reading, language, and cognitive measures in subjects from the Avon Longitudinal Study of Parents and Children (ALSPAC). Associations were then replicated in three independent, selected cohorts. Confirming the results of the other Examples described herein, there were associations with known RD risk genes KIAA0319 and DCDC2 (FIG. 6A). In addition, other markers were identified in or near other DYX2 genes, including TDP2, ACOT13, C6orf62, FAM65B, and CMAHP. The LD structure of the locus suggests that association hits within TDP2, ACOT13, and C6orf62 are capturing a previously reported risk variant in KIAA0319. These results further substantiate KIAA0319 and DCDC2 as major effector genes in DYX2 and identify FAM65B and CMAHP as new DYX2 risk genes. Association of DYX2 with multiple neurobehavioral traits suggests risk variants have functional consequences affecting multiple neurological processes.

Methods

Subjects

The discovery cohort in this investigation was the Avon Longitudinal Study of Parents and Children (ALSPAC). The ALSPAC is a population-based birth cohort based in Avon, United Kingdom. Subjects were recruited before birth—a total of 15,458 fetuses were recruited, of whom 14,701 were alive at 1 year of age. Recruitment, participants, and study methodologies are described in detail elsewhere (bristol.ac.uk/alspac) (Boyd et al. 2012; Golding et al. 2001). DNA samples for genetic analysis were available for 10,259 subjects. Reading, language, and cognitive measures were performed at ages 7, 8, and 9 years. Subjects with IQ≤75 on the Wechsler Intelligence Scale for Children (WISC-III) Total IQ were excluded to prevent confounding effects of Intellectual Disability (Eicher et al. 2013a; Eicher et al. 2013b; Powers et al. 2013; Wechsler et al. 2002). To prevent population stratification in genetic analyses, subjects of non-European descent were also excluded. Samples with overall genotype call rates <0.85 were excluded from analyses, leaving a final sample size of 5579 individuals for LI analyses and 5525 individuals for RD analyses. Ethical approval was obtained from the ALSPAC Ethics and Law Committee, Local UK Research Ethics Committees, and the Yale Human Investigation Committee.

Reading, Language, and Cognitive Measures

Reading measures in the ALSPAC used in this investigation include a phoneme deletion task at age 7 years, single-word reading at ages 7 and 9 years, and single non-word reading at age 9 years (Table 1a). The phoneme deletion task, also known as the Auditory Analysis Test, measures phoneme awareness, a core deficit in RD (Rosner and Simon 1971). For the phoneme deletion task, the child listens to a word spoken aloud and is then asked to remove a specific phoneme from that word to make a new word. Single-word reading was assessed at age 7 years using the reading subtest of the Wechsler Objective Reading Dimensions (WORD) (Rust et al. 1993). At age 9 years, single-word reading was again assessed by asking the child to read ten real words and ten non-words aloud, a subset of a larger list of words and non-words (Nunes et al. 2003). To examine severe cases (Severe RD), cases were defined as having a score 2 or more standard deviations below the mean on the phoneme deletion task (Table 1b). Cases with Moderate RD were also defined as scoring at least 1 standard deviation below the mean on single-word reading at age 7 years, single-word reading at age 9 years, and single non-word reading at age 9 years (Table 1b). A threshold of 1 standard deviation was chosen as measures were included at three time points to isolate individuals with persistently poor decoding skills Different severity levels were examined because past studies in the DYX2 locus have shown differences in genetic association patterns depending on case severity, particularly with KIAA0319 associating with more moderate RD case definitions and DCDC2 with more severe definitions (Paracchini et al. 2008; Powers et al. 2013; Scerri et al. 2011).

Language measures were collected at age 8 years (Table 1a). An adaptation of the Nonword Repetition Task (NWR), in which subjects repeated recordings of nonwords, assessed short-term phonological memory and processing abilities (Gathercole and Baddeley 1996). Children also completed the Wechsler Objective Language Dimensions (WOLD) verbal comprehension task at age 8 years (Wechsler et al. 1996), where they answered questions about a paragraph read aloud by an examiner describing a presented picture. These measures were looked at because individuals with LI are known to perform consistently poorly on NWR and WOLD tasks (Bishop et al. 1996; Newbury et al. 2009). As with RD, the association of the DYX2 locus with severe and moderate case definitions of LI was also examined. To assess the risk imparted for severe LI, severe LI cases were defined as scoring 2 or more standard deviations below the sample mean on either task (Severe LI) (Table 1b). To assess more moderate deficits, cases were defined as scoring at least 1.5 standard deviations below the sample mean on each task (Moderate NWR and Moderate WOLD) (Table 1b). As fewer measures were used to assess LI related traits, the threshold for case definitions was increased to 1.5 standard deviations to assess more moderate deficits. Verbal, performance, and total IQ were assessed at age 8 years, using the Wechsler Intelligence Scale for Children (WISC-III) (Table 1a). IQ measures were examined as quantitative traits (Table 1b).

Genotyping and Genetic Analyses

A SNP marker panel was developed to capture the common variation in the DYX2 locus. TagSNPs in the locus were selected using the association study design server of Han et al. (Han et al. 2008). The final DYX2 panel contained 195 SNPs with an estimated average power of 83% and 68% to capture known common and rare variants, respectively, in the DYX2 locus spanning approximately 1.4 Mb. Markers were genotyped on the Sequenom platform (San Diego, Calif.), following manufacturer's guidelines, at the Yale Center for Genome Analysis (West Haven, Conn.).

Markers that deviated substantially from Hardy-Weinberg equilibrium, or that had an overall call rate <85%, were not used for haplotype-based analysis. In the discovery ALSPAC cohort, single marker SNP analyses of case-control statuses and quantitative traits were completed using SNP & Variation Suite (SVS) v7.6.4 (Bozeman, Mont.). Linkage disequilibrium was assessed and haplotype blocks were constructed using the four-gamete rule option in HaploView v4.2. Haplotype association tests were performed with haplotypes that had frequencies greater than or equal to 1% using PLINK v1.07 (Barrett et al. 2005; Purcell et al. 2007). Associations with p<0.001 are reported for the ALSPAC discovery cohort to present suggestive results. However, to correct for multiple testing, a Bonferroni threshold of 0.000256 (0.05 divided by 195 markers) was used for discovery association tests in the ALSPAC cohort.

Following discovery analyses in the ALSPAC, associated variants were assessed in three cohorts specifically recruited for either RD or LI: Iowa LI, Italian RD, and Colorado RD (Table 2). The Iowa LI cohort is comprised of 219 LI cases and 209 sex- and age-matched, unrelated controls collected at the University of Iowa. Subjects completed various language measures, including the Woodcock Johnson-III (WJ) and the Gray Oral Reading Test (GORT), which were used to derive a composite language score, which was then dichotomized into case-control status at −1.14 standard deviations (Eicher et al. 2013a; Weismer 2000). The Colorado Learning Disabilities Research Center (CLDRC) cohort consists of 1201 individuals in 293 nuclear families. Families were recruited to the study if at least one child had a history of reading problems. The Italian cohort consists of 878 individuals in 304 nuclear families; these families were recruited via a proband with clinically diagnosed RD. Ethical approval for recruitment and study methodologies were obtained from the Yale Human Investigation Committee and Institutional Review Boards at the University of Iowa, the University of Denver, and Italy. SNPs that had single marker or within-haplotype associations with p<0.001 in the ALSPAC were tested for replication in the Iowa LI, Italian RD, and Colorado RD cohorts. Iowa LI was analyzed using SNP & Variation Suite (SVS) v7.6.4 (Bozeman, Mont.), while the family-based Italian RD and Colorado RD cohorts were examined using PLINK v1.07 (Purcell et al. 2007). Suggestive ALSPAC results were moved forward for replication analyses in order to emphasize replication of associations over statistical corrections for multiple testing. Replications with p<0.05 in the Iowa LI, Italian RD, and Colorado RD cohorts are reported.

Results

Association with DYX2 markers was performed in three separate domains: (1) RD, (2) LI, and (3) IQ. For the sake of clarity, associations are presented domain-by-domain, with an emphasis on replication for strength of associations as opposed to correction for multiple testing.

RD

Associations with RD were performed using two different severity definitions: (1) Severe RD and (2) Moderate RD (Table 1b). For Severe RD, associations were found with DCDC2, KIAA0319, and TDP2 (Table 3). The association of DCDC2 and Severe RD is explored fully in Example 1; Powers et al. (2013). TDP2 marker rs2294691 did not replicate its association in any of the three replication cohorts (Table 5). KIAA0319 marker rs10456309 replicated in Iowa LI and Colorado RD cohorts (Table 5). With Moderate RD, there was an association between rs1562422 near the gene FAM65B and the pseudogene CMAHP, which was replicated in the Colorado RD cohort (Table 3, Table 5).

LI

Association tests were performed on three LI phenotypes: (1) Severe LI, (2) Moderate NWR, and (3) Moderate WOLD (Table 1b). As with Severe RD, there were associations between DCDC2 and Severe LI. The DCDC2 haplotype that associated with Severe LI is discussed in Example 1; Powers et al (2013). A marker within this DCDC2 haplotype, rs807694, showed association with Severe LI and was replicated in the Iowa LI cohort (Table 3, Table 5). With a more moderate case definition, associations were observed with ACOT13 and C6orf62 (Table 3), genes neighboring KIAA0319 and TDP2. Both rs3777663 in ACOT13 and rs3756814 in C6orf62 showed associations in the Italian RD and Iowa LI cohorts (Table 5).

IQ

Association tests were also performed between DYX2 markers and Verbal IQ, Performance IQ, and Total IQ (Table 1b). Verbal IQ associations included single markers and haplotypes covering the 5' half of KIAA0319, rs9348646 in FAM65B, and a haplotype spanning ACOT13 and C6orf62, with evidence of replication (Table 4a, Table 4b, Table 5). There was substantial overlap of DYX2 associations with Verbal IQ and associations with RD and LI. These similarities of associations are not unexpected, as the traits are highly correlated and known to capture similar domains (Table 6). The associations of DYX2 with Performance and Total IQ were weaker; there were no associations with Performance IQ and a single, non-replicated association of Total IQ with rs2328791, which is located in a large intergenic region telomeric to NRSN1 and DCDC2 (Table 4a, Table 4b, Table 5).

Linkage Disequilibrium within DYX2

In the analyses, replicated associations were observed in the following genes: DCDC2, KIAA0319, TDP2, ACOT13, C6orf62, FAM65B, and the pseudogene CMAHP. However, as these SNPs are in close proximity to each other, linkage disequilibrium (LD) was assessed among the marker panel to determine whether the associated SNPs were tagging the same variation in the locus. As described in Examples 1 and 2, DCDC2 associations tagged READ1 alleles. Within KIAA0319, there appear to be two clear LD blocks separating the gene into a 5' half and a 3' half (data not shown). The 5' half of KIAA0319 is in strong LD with TDP2, ACOT13, and C6orf62, indicating that associations within these genes may be capturing that same variation (data not shown). Associations in FAM65B and CMAHP appear to be tagging independent associations (data not shown). Although rs1562422 is located intergenic to FAM65B and CMAHP, this marker is in strong LD with other markers within the CMAHP pseudogene. Integration of the association analyses and LD structure indicate four independent association signals centered on (1) DCDC2, (2) the 5' half of KIAA0319, (3) FAM65B, and (4) CMAHP.

In this Example, the relationship of the DYX2 locus with RD, LI, and IQ is characterized (FIG. 6B). The results confirm the associations of RD risk genes KIAA0319 and DCDC2 to include LI. Additionally, FAM65B and CMAHP were identified as risk genes for linguistic traits. Markers within the DYX2 locus showed association with numerous communication traits, including RD, LI, and Verbal IQ. There was a marked absence of DYX2 associations with Total and Performance IQ, indicating that the DYX2 locus influences language-related processes to a much greater extent than overall cognitive traits.

The genetic association of DYX2 with RD, LI, and Verbal IQ is the latest example of various neurocognitive and communication processes sharing genetic associations. Applicant and others have shown that these neurobehavioral traits have common genetic contributors, including variants in FOXP2, KIAA0319, CMIP, ZNF385D, CNTNAP2, and DCDC2 (Eicher et al 2013b; Newbury et al. 2009; Newbury et al. 2011, Pennington and Bishop 2009, Peter et al. 2011; Pinel et al. 2012; Powers et al. 2013; Scerri et al. 2011; Wilcke et al. 2012). The expansion of DYX2's association from reading to include other language-related processes suggests that the causative variants may affect these traits in a pleiotropic manner, as opposed to influencing written or verbal language exclusively. The findings of this study collude with this 'generalist genes hypothesis,' which is also supported by a recent genome-wide complex trait analysis (GTCA) of cognitive and learning abilities (Trzaskowski et al. 2013). The strong correlations and relatedness among these neurocognitive measures (Table 6) suggest that these DYX2 genes affect central language processes, which in turn manifest themselves phenotypically in various ways, including reading, language, and cognition.

That multiple DYX2 genes showed association with the phenotypes in this study is interesting, and at first glance somewhat unexpected. One possibility is that one or two genes are not solely responsible for the consistent implication of this locus in reading, language, and cognitive phenotypes, as is largely believed. KIAA0319 and DCDC2 are currently known as the two major risk genes in the DYX2 locus. Both have been implicated in both RD and subclinical variation in reading performance, using both classical neurobehavioral measures, and more recently, neuro-imaging techniques (Eicher and Gruen 2013; Graham and Fisher 2013). Other genes in DYX2 have been associated with RD, but not nearly as often as DCDC2 and KIAA0319. However, with the dense SNP panel described herein, it was possible to observe associations with other DYX2 elements, including FAM65B and CMAHP.

Another possible explanation for the number of DYX2 genes observed associating with the phenotypes in this study is LD within the DYX2 locus. In fact, LD likely explains the cluster of associations around KIAA0319, TDP2, ACOT13, and C6orf62. As described herein, two major LD blocks span KIAA0319—one spans the 3' half of the gene, while the other spans the 5' region of KIAA0319 as well as ACOT13, TDP2, and part of C6orf62. Nearly all of the associations in this study localize to this 5' LD block, which also contains the previously reported KIAA0319 RD risk haplotype. Because of this LD structure, it is impossible to determine whether the associations in this region are independent, or are capturing the same functional variant. The latter possibility is considered the most likely, and it is believed that the associations in this region are likely tagging the same causative variant captured by the KIAA0319 RD risk haplotype. Functional study of this region—particularly of the less studied genes TDP2, ACOT13, and C6orf62—will be useful to determine whether these associations are independent or not.

By contrast, the markers within or near FAM65B and CMAHP appear to be capturing distinct association signals from two different LD blocks (data not shown). The SNP rs9348646, which showed association with Verbal IQ, is located within an intron of FAM65B in one LD block, while rs1562422, which showed association with Moderate RD, localized to a separate LD block. While rs1562422 is an intergenic marker located physically between FAM65B and CMAHP, it shows strong LD with markers in CMAHP (data not shown). The LD patterns within the DYX2 locus suggest that associations in KIAA0319, TDP2, ACOT13, and C6orf62 are tagging the same causative variant, while rs9348646 in FAM65B and rs1562422 are independent.

The other DYX2 genes, including FAM65B and CMAHP, have been studied far less than the risk genes DCDC2 and KIAA0319. Little is known about FAM65B in terms of biological function; however, there is evidence that FAM65B may influence migration in T lymphocytes (Rougerie et al. 2013). Animal models of DCDC2 and KIAA0319 have implicated these genes in migratory processes, albeit in a neural context. CMAHP, which encodes a key enzyme in the synthesis of the sialic acids Neu5Ac and Neu5Gc in other mammals, was rendered a pseudogene in humans by an inactivating microdeletion and subsequent fixation of the inactive allele in early human populations (Chou et al. 1998). Although ACOT13 appears to be tagging variation within KIAA0319, the preliminary functional studies of ACOT13 are intriguing. ACOT13 was recently associated with lower asymmetric activation of the posterior superior temporal sulcus during reading and phonology tasks (Pinel et al. 2012). The protein product encoded by ACOT13 has been co-localized with beta-tubulin on microtubules; microtubule binding is postulated to be important to RD, as DCDC2 contains two doublecortin domains that are thought to bind microtubules (Cheng et al. 2006).

Genes and regulatory elements within the DYX2 locus may contribute interactively to reading and language domains, as seen with the non-additive relationship between putative regulatory variants in DCDC2 and KIAA0319 (Example 1; Powers et al. 2013, Ludwig et al. 2008). These risk variants have been shown to influence gene expression, and to interact with each other to substantially influence performance on reading and language tasks. A complex regulatory network, where regulatory elements interact and co-regulate other DYX2 genes and elements, may contribute to reading, language, and cognition. If so, it is likely that the READ1 element in DCDC2 and the causative variant tagged by the KIAA0319 risk haplotype have the strongest effects upon gene expression and ultimate neurocognitive phenotype. Supporting this idea is the fact that so many of the association hits described herein—both single-marker and haplotype-based, and with all three phenotypes—localize to the same LD block as the KIAA0319 risk haplotype. This result, together with the KIAA0319 risk haplotype's association with reduced KIAA0319 expression and its synergistic interaction with a regulatory element in an intron of DCDC2, indicate the presence of at least one regulatory variant in this region that influences KIAA0319 expression. The locations of the only other independent hits in the locus (aside from READ1 in DCDC2)—an intron of FAM65B and downstream of a pseudogene—may suggest additional regulatory regions that influence gene expression. Based on work described herein, DCDC2 and KIAA0319 are the major effector genes responsible for DYX2's influence on RD and LI risk and alteration of gene expression levels or patterns is the mechanism by which this effect is exerted.

Replication of genetic associations in independent cohorts was emphasized in the work described herein, rather than reliance on statistical corrections for multiple testing, for validation of associations in the ALSPAC discovery cohort. The replications of genetic association with the neurocognitive traits of interest, particularly in the varied cohorts in this investigation, provide strong evidence that the results of this study are not due to Type I error. Uncorrected p-values and a statistical threshold correcting for 195 genetic markers (threshold of 0.000256) are also reported in order to present the context of the findings in terms of strength and reliability. Nonetheless, the three replication cohorts were not identical and had inherent differences among themselves and relative to the discovery cohort that may have prevented replication. These differences included: (1) the disorder for which each cohort was selected (RD vs. LI vs. unselected), (2) severity of case definition and recruitment, and 3) country of recruitment (UK vs. US vs. Italy), and language spoken (English vs. Italian). For instance, the use of a regular language such as Italian as opposed to an irregular language such as English may have allowed for easier detection of true reading and language deficiencies. This issue was likely avoided in the discovery ALSPAC cohort due to the large sample size. The observation of multiple replicated associations throughout the DYX2 locus described herein increases confidence in these results.

In summary, the analyses indicate four association signals for RD, LI, and Verbal IQ in the DYX2 locus: DCDC2, KIAA0319, FAM65B, and the pseudogene CMAHP. The association results within the DCDC2 and KIAA0319 (including TDP2, ACOT13, and C6orf62) areas are in LD with two previously reported risk variants: the READ 1 regulatory element in DCDC2 and the KIAA0319 risk haplotype in KIAA0319 and TDP2. These results point strongly to variation in KIAA0319 gene expression as a mediator of DYX2's effect on reading and language phenotypes.

REFERENCES

Barrett J C, et al. (2005) *Bioinformatics* 21:263-265.
Beaver K M, et al. (2010) *J Neural Transm* 117(7):827-30.
Bishop D V, et al. (2008) *Genes Brain Behav* 7(3):365-72.
Bishop D V, et al. (1996) *J Child Physiol Psychiatry* 37:391-403.
Boyd A, et al. (2012) *Int J Epidemiol* 42(1):111-27.
Cardon L R, et al. (1994) *Science* 266(5183):276-9.
Catts H W, et al. (2005) *J Speech Lang Hear Res* 48(6):1378-96.
Cheng Z, et al. (2006) *Biochem Biophys Res Commun* 350(4):850-3.
Chou H H, et al. (1998) *Proc Natl Acad Sci USA* 95(20): 11751-6.
Cope N, et al. (2005) *Am J Hum Genet* 76(4):581-91.
Couto J M, et al. (2010) *Am J Med Genet B Neuropsychatr Genet* 153B(2):447-62.
Deffenbacher K E, et al. (2004) *Hum Genet* 115(2):128-38.
Dennis M Y, et al. (2009) *PLoS Genet* 5(3):e1000436.
Eicher J D and Gruen J R. (2013) *Mol Genet Metab*, doi: 10.1016/j.ymgme.2013.07.001.
Eicher J D, et al. (2013a) *PLoS One* 8(5):e63762.
Eicher J D, et al. (2013b) *Genes Brain Behav*, in press.
Elbert A, et al. (2011) *Behav Genet* 41(1):77-89.
Francks C, et al. (2004) *Am J Hum Genet* 75(6):1046-1058.
Gathercole S, and Baddeley A D. (1990) *Journal of Memory and Language* 29:336-360.
Gathercole S E, and Baddeley A D. (1993) *Lawrence Erlbaum, Mahwah, N.J.*
Gathercole S E, and Baddeley A D. (1996) The Psychological Corportation, London.
Gayan J, et al. (1999) *Am J Hum Genet* 64(1):157-64.
Golding J, et al. (2001) *Paediatr Perinat Epidemiol* 15(1):74-87.
Graham S A, and Fisher S E. (2013) *Curr Opin Neurobiol* 23(1):43-51.
Han B, et al. (2008) *Ann Hum Genet* 72(Pt 6):834-847
Harold D, et al. (2006) *Mol Psychiatry* 11(12):1085-1091.
Kaminen N, et al. (2003) *J Med Genet* 40(5):340-5.
Kaplan D E, et al. (2002) *Am J Hum Genet* 70(5):1287-98.
Landi N, et al. (2013) *Dev Sci* 16(1):13-23.
Lind P A, et al. (2010) *Eur J Hum Genet* 18(6):668-73.
Lucano M, et al. (2007) *Biol Psychiatry* 62:811-817.
Ludwig K U, et al. (2008) *J Neural Transm* 115(11):1587-9.
Marino C, et al. (2012) *Psychiatr Genet* 22(1):25-30.
Meng H, et al. (2011) *Behav Genet* 41(1):58-66.
Meng H, et al. (2005) *Proc Natl Acad Sci USA* 102:17053-17058.
Newbury D F, et al. (2010) *Genome Med* 2(1):6.
Newbury D F, et al. (2011) *Behav Genet* 41(1):90-104.
Newbury D F, et al. (2009) *Am J Hum Genet* 85(2):264-72.
Nunes T, et al. (2003) *Scientific Studies of Reading* 7(3):289-307.
Paracchini S, et al. (2008). *Am J Psychiat* 165(12):1576-1584.
Paracchini S, et al. (2006) *Hum Mol Genet* 15(10):1659-1666.
Pennington B F. (2006) *Cognition* 101(2):385-413.
Pennington B F, and Bishop D V (2009) *Annual Review of Psychology* 60:283-306.
Peter B, et al. (2011) *J Neurodev Disord* 3(1):39-49.
Pinel P, et al. (2012) *J Neurosci* 32(3):817-25.
Plomin R, et al. (2004) *Mol Psychiatry* 9(6):582-6.
Powers N R, et al. (2013) *Am J Hum Genet* 93(1):19-28.
Purcell S, et al. (2007) *Am J Hum Genet* 81(3):559-575.
Rosner J, and Simon D P. (1971) *Journal of Learning Disabilities* 4(384):40-48.
Rougerie P, et al. (2013) *J Immunol* 190(2):748-55.
Rust J, et al. (1993) Psychological Corporation, Sidcup, UK.
Scerri T S, et al. (2011) *Biol Psychiatry* 70:237-245.
Schumacher J, et al. (2006) *Am J Hum Genet* 78(1):52-62.
Trzaskowski M, et al. (2013) *Behav Genet* 43(4):267-73.
Wechsler D. (1996) Psychological Corporation, London, UK.
Wechsler D, et al. (1992) Psychological Corporation, Sidcup, UK.
Weismer S E, et al. (2000) *J Speech Lang Hear Res* 43(4):865-78.

Wilcke A, et al. (2011) *Eur J Hum Genet* 20(2):224-9.
Wilcke A, et al. (2009) *Ann Dyslexia* 59(1):1-11.
Wise J C, et al. (2007) *J Speech Lang Hear Res* 50(4): 1093-9.
Wong P C, et al. (2013) *PLoS One* 8(5):e64983.
Viding E, et al. (2004) *J Child Psychol Psychiatry* 45(2): 315-25.
Zhong R, et al. (2013) *Mol Neurobiol* 47(1):435-42.
Zou L, et al. (2012) *Am J Med Genet B Neuropsychiatr Genet* 159B(8):970-6.

FIGURE LEGENDS

FIG. 1: Schematic of the genes within the DYX2 locus on chromosome 6p21.3. Genes in blue, DCDC2 and KIAA0319, have replicated associations with written and verbal language phenotypes, namely RD and LI. Regions in red mark two functional variants, READ1 in DCDC2 and a risk haplotype with markers in KIAA0319 and TDP2, which have been functionally associated with RD and LI using animal models and molecular techniques.

Figure 4:
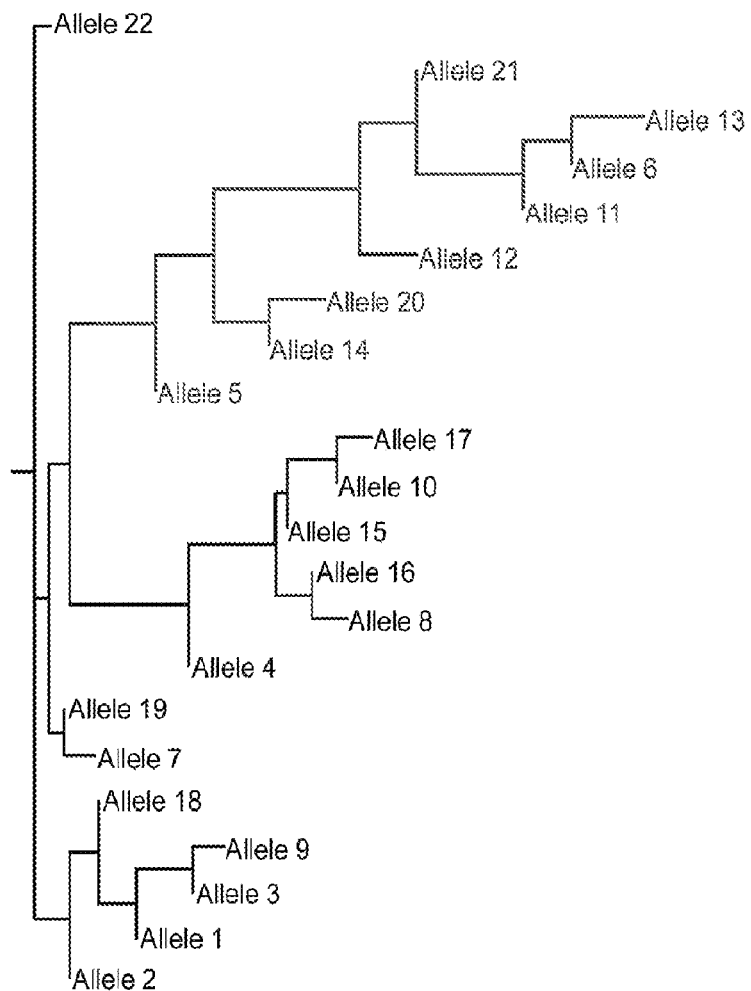
FIG. 4: Phylogenetic tree based on multiple alignment of 22 BV677278 alleles. The Clustal W algorithm was used, with default method parameters (IUB matrix, gap penalty=15, gap extension penalty=6.66). Clade 1, which contains risk alleles 5 and 6, is the top most branched grouping, in light grey (not including the branch for Allele 22).

FIG. 4: An updated schematic of genes in our study with markers that show replicated associations to RD, LI, and/or IQ. The list of these genes (shown in blue) has expanded to seven (DCDC2, KIAA0319, TDP2, ACOT13, C6orf62, FAM65B, and CMAHP), although linkage disequilibrium may account for multiple associations (particularly for KIAA0319, TDP2, ACOT13, and C6orf62).

Tables of Example 3

TABLE 1a

ALSPAC Phenotype Measures

| Measure | Domain |
|---|---|
| Phoneme Deletion (PD) Age 7 Years | Reading (RD) |
| Single Word Reading (SWR7) Age 7 Years | Reading (RD) |
| Single Nonword Reading (SNR) Age 7 Years | Reading (RD) |
| Single Word Reading (SWR9) Age 9 Years | Reading (RD) |
| Wechsler Objective Language Dimensions (WOLD) Verbal Comprehension Age 8 | Language (LI) |
| Nonword Repetition Task (NWR) Age 8 Years | Language (LI) |
| Wechsler Intelligence Scale for Children (WISC) Total IQ (TIQ) Age 8 Years | Cognition (IQ) |
| Wechsler Intelligence Scale for Children (WISC) Verbal IQ (VIQ) Age 8 Years | Cognition (IQ) |
| Wechsler Intelligence Scale for Children (WISC) Performance IQ (PIQ) Age 8 Years | Cognition (IQ) |

TABLE 1b

Phenotype Definitions for ALSPAC Analyses

| Reading (RD) | Phenotype Definition |
|---|---|
| Severe RD | 2 standard deviations below sample mean on the phoneme deletion task |
| Moderate RD | 1 standard deviation below sample mean on SWR7, SNR, and SWR tasks |
| Language (LI) | Phenotype Definition |
| Severe LI | 2 standard deviations below sample mean on either WOLD and/or NWR tasks |
| Moderate WOLD | 1.5 standard deviations below sample mean on the WOLD task |
| Moderate NWR | 1.5 standard deviations below sample mean on the NWR task |
| Cognition (IQ) | Phenotype Definition |
| Total IQ | Quantitative performance on WISC Total IQ task |
| Verbal IQ | Quantitative performance on WISC Verbal IQ task |
| Performance IQ | Quantitative performance on WISC Performance IQ task |

TABLE 2

Replication Cohorts

| | Iowa LI | Colorado RD | Italy RD |
|---|---|---|---|
| Number of Subjects | 428 | 1201 | 878 |
| Number of Families | N/A | 293 | 304 |
| Disorder | LI | RD | RD |
| Cohort-type | Case-control | Family-based | Family-based |
| Analysis | SVS | TDT (PLINK) | TDT (PLINK) |
| Association | Case-control | Case-control | Case-control |
| Conditioned on: | Status | Status and Discriminant Score | Status |
| Case Status Determined on: | Composite score on language measures | | Speed or Accuracy on text- or single-word reading task |

TABLE 3

Single marker genetic associations with various RD and LI case-control definitions.

| Phenotype | Marker | Gene | BP Location | Model | OR (95% CI) | P-value |
|---|---|---|---|---|---|---|
| Severe RD | rs2294691 | TDP2 | 24652843 | Allelic | 2.0 (1.3-2.9) | 0.00050 |
| Severe RD | rs2294691 | TDP2 | 24652843 | Additive | 1.9 (1.3-2.8) | 0.00053 |
| Severe RD | rs2294691 | TDP2 | 24652843 | Dominant | 2.3 (1.5-3.7) | 0.00018* |
| Severe RD | rs10456309 | KIAA0319 | 24589562 | Recessive | 10.5 (2.2-49.5) | 0.00020* |
| Moderate RD | rs1562422 | CMAHP | 25044577 | Dominant | 1.7 (1.2-2.2) | 0.00081 |
| Severe LI | rs807694 | DCDC2 | 24303383 | Additive | 1.8 (1.3-2.5) | 0.00057 |
| Severe LI | rs807694 | DCDC2 | 24303383 | Allelic | 1.8 (1.3-2.5) | 0.00050 |
| Severe LI | rs807694 | DCDC2 | 24303383 | Dominant | 1.9 (1.3-2.7) | 0.00062 |
| Moderate WOLD | rs3756814 | C6orf62 | 24705835 | Additive | 0.7 (0.6-0.9) | 0.00039 |
| Moderate WOLD | rs3756814 | C6orf62 | 24705835 | Allelic | 0.7 (0.6-0.9) | 0.00047 |
| Moderate WOLD | rs3777663 | ACOT13 | 24700235 | Additive | 0.6 (0.5-0.8) | 0.00039 |
| Moderate WOLD | rs3777663 | ACOT13 | 24700235 | Allelic | 0.7 (0.5-0.8) | 0.00041 |

*Genetic association survives correction for multiple testing

Table 4: Single marker (Table 4a) and haplotype based (Table 4b) genetic associations with quantitative measure of cognition.

TABLE 4a

Single marker genetic associations with cognition

| Phenotype | Marker | Gene | BP Location | Model | Slope | P-value |
|---|---|---|---|---|---|---|
| Verbal IQ | rs9295626 | KIAA0319 | 24587339 | Allelic | 1.40 | 0.00041 |
| Verbal IQ | rs9295626 | KIAA0319 | 24587339 | Additive | 1.39 | 0.00043 |
| Verbal IQ | rs7763790 | KIAA0319 | 24615063 | Allelic | −1.40 | 0.00045 |
| Verbal IQ | rs7763790 | KIAA0319 | 24615063 | Additive | −1.38 | 0.00048 |
| Verbal IQ | rs6935076 | KIAA0319 | 24644322 | Allelic | 1.16 | 0.00049 |
| Verbal IQ | rs6935076 | KIAA0319 | 24644322 | Additive | 1.15 | 0.00052 |
| Verbal IQ | rs9348646 | FAM65B | 24052526 | Allelic | −1.14 | 0.00066 |
| Verbal IQ | rs9348646 | FAM65B | 24052526 | Additive | −1.14 | 0.00066 |
| Total IQ | rs2328791 | N/A | 23736848 | Allelic | −1.21 | 0.00066 |
| Total IQ | rs2328791 | N/A | 23736848 | Additive | −1.18 | 0.00075 |
| Total IQ | rs2328791 | N/A | 23736848 | Recessive | −3.36 | 0.00042 |

TABLE 4b

Haplotype based genetic associations with cognition

| Markers | Haplotype | Gene | BP Location | Slope | P-value |
|---|---|---|---|---|---|
| rs2817201, rs9295626 | AT | KIAA0319 | 24585214, 24587339 | 1.42 | 0.000378 |
| rs10456309, rs4576240, rs17307478, rs9356939, rs7763790, rs6456621 | GGTCAC | KIAA0319 | 24589562, 24596478, 24605024. 24613354, 24615063, 24618511 | −1.40 | 0.000569 |
| rs6456624, rs6935076, rs2038137, | AGATA | KIAA0319 | 24639223, 24644322, 24645943, | 1.81 | 0.0000145* |
| rs3756821, rs1883593, rs3212236, rs3777663, rs3756814, rs6931809, rs6916186, rs6933328, rs17491647 | TGTGGA | ACOT13/ C6orf62 | 24646821, 24647191, 24648455 24700235, 24705835, 24706770, 24708523, 24710920, 24713723 | −1.56 | 0.000742 |

*Genetic association survives correction for multiple testing

TABLE 5

Replication of genetic associations in the Iowa, Italian, and Colorado cohorts.

| | | Iowa Case Control | | Italy Case Control | | Colorado Case Control | | Colorado Discriminant Score | |
|---|---|---|---|---|---|---|---|---|---|
| Marker | Gene | OR | p | OR | p | OR | p | Slope | p |
| rs2328791 | N/A | 1.0 | 0.813 | 1.0 | 1.000 | 0.9 | 0.646 | 0.087 | 0.447 |
| rs33914824[a] | DCDC2 | 2.2 | 0.034 | 0.9 | 0.768 | 1.1 | 0.847 | 0.023 | 0.934 |
| rs807694[a] | DCDC2 | 1.9 | 0.028 | 0.9 | 0.786 | 0.9 | 0.853 | −0.025 | 0.919 |
| rs707864[a] | DCDC2 | 1.6 | 0.017 | 1.0 | 0.840 | 1.2 | 0.446 | −0.246 | 0.101 |
| rs10456301[a] | DCDC2 | 0.9 | 0.553 | 1.1 | 0.811 | 1.5 | 0.289 | 0.221 | 0.162 |
| rs16889066[a] | DCDC2 | 1.2 | 0.517 | 1.0 | 0.884 | 1.2 | 0.622 | −0.304 | 0.150 |
| rs9379651[a] | DCDC2 | 1.1 | 0.602 | 1.3 | 0.225 | 0.6 | 0.059 | 0.205 | 0.141 |
| rs2817201 | KIAA0319 | 1.1 | 0.733 | 1.2 | 0.129 | 1.0 | 1.000 | 0.034 | 0.787 |
| rs9295626 | KIAA0319 | 1.1 | 0.579 | 0.6 | 0.0055 | 1.0 | 0.823 | −0.158 | 0.169 |
| rs10456309 | KIAA0319 | 0.5 | 0.073 | 0.7 | 0.189 | 0.4 | 0.206 | 0.628 | 0.00845 |
| rs4576240 | KIAA0319 | 1.1 | 0.825 | 1.9 | 0.0027 | 1.1 | 0.862 | −0.052 | 0.754 |
| rs17307478 | KIAA0319 | 1.0 | 0.996 | 1.3 | 0.292 | 0.8 | 0.555 | 0.039 | 0.803 |
| rs9356939 | KIAA0319 | 4.0 | 0.018 | 0.8 | 0.069 | 1.3 | 0.151 | −0.116 | 0.254 |
| rs7763790 | KIAA0319 | 1.0 | 0.831 | 1.1 | 0.627 | 1.4 | 0.163 | 0.014 | 0.910 |
| rs6456621 | KIAA0319 | 2.2 | 0.019 | 1.6 | 0.405 | 1.8 | 0.366 | −0.458 | 0.104 |
| rs3756821 | KIAA0319 | 1.2 | 0.278 | 1.0 | 0.842 | 1.2 | 0.327 | −0.033 | 0.734 |
| rs1883593 | KIAA0319 | 1.3 | 0.169 | 1.6 | 0.0052 | 1.3 | 0.239 | −0.108 | 0.395 |
| rs3212236 | KIAA0319 | 1.0 | 0.883 | 1.1 | 0.496 | 0.9 | 0.745 | −0.124 | 0.319 |
| rs2294691 | TDP2 | 1.1 | 0.779 | 1.9 | 0.0578 | 1.4 | 0.491 | −0.290 | 0.247 |
| rs3777663 | ACOT13 | 0.7 | 0.016 | 0.6 | 0.0052 | 1.0 | 0.908 | 0.101 | 0.345 |
| rs3756814 | C6orf62 | 0.7 | 0.005 | 0.7 | 0.023 | 0.9 | 0.600 | −0.003 | 0.980 |
| rs6931809 | C6orf62 | 1.4 | 0.023 | 1.4 | 0.017 | 1.2 | 0.491 | −0.096 | 0.382 |
| rs6916186 | C6orf62 | 0.9 | 0.757 | 1.2 | 0.413 | 1.2 | 0.547 | 0.112 | 0.490 |
| rs6933328 | C6orf62 | 0.9 | 0.612 | 0.9 | 0.613 | 1.0 | 0.827 | 0.215 | 0.0437 |

TABLE 5-continued

Replication of genetic associations in the Iowa, Italian, and Colorado cohorts.

| Marker | Gene | Iowa Case Control | | Italy Case Control | | Colorado Case Control | | Colorado Discriminant Score | |
|---|---|---|---|---|---|---|---|---|---|
| | | OR | p | OR | p | OR | p | Slope | p |
| rs17491647 | C6orf62 | 0.8 | 0.155 | 0.7 | 0.104 | 1.0 | 0.901 | 0.042 | 0.709 |
| rs9348646 | FAM65B | 0.9 | 0.358 | 1.1 | 0.535 | 1.4 | 0.144 | −0.415 | 0.00021 |
| rs1562422 | CMAHP | 1.0 | 0.793 | 1.0 | 0.796 | 0.6 | 0.093 | −0.030 | 0.840 |

[a]These markers are part of the six-marker risk haplotype in DCDC2 fully discussed in Powers et al. 2013.

TABLE 6

Phenotype correlations in the ALSPAC cohort*

| | NWR | WOLD | SWR7 | SWR9 | SNR | PD | TIQ | VIQ | PIQ |
|---|---|---|---|---|---|---|---|---|---|
| NWR | 1 | | | | | | | | |
| WOLD | 0.214 | 1 | | | | | | | |
| SWR7 | 0.403 | 0.259 | 1 | | | | | | |
| SWR9 | 0.351 | 0.202 | 0.722 | 1 | | | | | |
| SNR | 0.306 | 0.149 | 0.660 | 0.708 | 1 | | | | |
| PD | 0.362 | 0.165 | 0.688 | 0.550 | 0.538 | 1 | | | |
| TIQ | 0.324 | 0.386 | 0.500 | 0.387 | 0.343 | 0.406 | 1 | | |
| VIQ | 0.346 | 0.424 | 0.536 | 0.421 | 0.421 | 0.426 | 0.871 | 1 | |
| PIQ | 0.192 | 0.216 | 0.292 | 0.218 | 0.218 | 0.246 | 0.819 | 0.435 | 1 |

*All correlations were had p < 0.05

Example 4

Genome-Wide Association Study of Shared Components of Reading Disability and Language Impairment; ZNF385D influences Reading and Language Disorders.

Introduction

Both RD and LI are complex traits that frequently co-occur, leading to the hypothesis that these disorders share genetic etiologies. To test this, a genome wide association study (GWAS) was performed on individuals affected with both RD and LI in the Avon Longitudinal Study of Parents and Children. The strongest associations were seen with markers in ZNF385D (OR=1.81, p=5.45×10$^{-7}$) and COL4A2 (OR=1.71, p=7.59×10$^{-7}$). Markers within NDST4 showed the strongest associations with LI individually (OR=1.827, p=1.40×10$^{-7}$). Association of ZNF385D was replicated using receptive vocabulary measures in the Pediatric Imaging Neurocognitive Genetics study (p=0.00245). Diffusion tensor imaging fiber tract volume data on 16 fiber tracts was then used to examine the implications of replicated markers. ZNF385D was a predictor of overall fiber tract volumes in both hemispheres, as well as global brain volume. In this Example, evidence is presented for ZNF385D as a risk gene for RD and LI. The implication of transcription factor ZNF385D in RD and LI underscores the importance of transcriptional regulation in the development of higher order neurocognitive traits.

Methods

ALSPAC.

Subject recruitment and collection of phenotype and genetic data for the ALSPAC cohort was completed by the ALSPAC team. The ALSPAC is a prospective population-based, birth cohort based in the Avon region of the United Kingdom. It consists mainly of children of northern European descent, born in 1991 and 1992. Children were recruited before birth; recruitment of their pregnant mothers resulted in a total of 15,458 fetuses, of whom 14,701 were alive at 1 year of age. Details regarding the participants, recruitment, and study methodologies are described in detail elsewhere (http://www.bristol.ac.uk/alspac) (Boyd et al., 2012; Golding et al., 2001). The children of the ALSPAC have been extensively phenotyped from before birth to early adulthood. Ethical approval was obtained from the ALSPAC Ethics and Law Committee, Local UK Research Ethics Committees, and the Yale Human Investigation Committee.

Reading and Language Measures.

The reading, language, and cognitive measures used for this study were collected at ages 7, 8, and 9 years. Subjects with IQ≤75 on the Wechsler Intelligence Scale for Children (WISC-III) Total IQ, completed at age 8 years, were excluded from the presented analyses (Weschler et al. 1992). Reading measures in the ALSPAC include a phoneme deletion task at age 7, single-word reading at ages 7 and 9 years, single non-word reading at age 9 years, and reading passage comprehension at age 9 years. The phoneme deletion task measures phoneme awareness, widely considered to be a core deficit in both RD and LI (Pennington 2006; Pennington & Bishop, 2009). For the phoneme deletion task, also known as the Auditory Analysis Test, the child listens to a word spoken aloud, and is then asked to remove a specific phoneme from that word to make a new word (Rosner & Simon, 1971). Single-word reading was assessed at age 7 using the reading subtest of the Wechsler Objective Reading Dimensions (WORD). At age 9, single-word and nonword reading were assessed by asking the child to read ten real words and ten non-words aloud from a subset of a larger list of words and non-words taken from research conducted by Terezinha Nunes and colleagues (Rust et al., 1993). Reading comprehension scores were ascertained at age 9, using the Neale Analysis of Reading Ability (NARA-II) (Neale 1997).

Two additional language measures, nonword repetition and verbal comprehension tasks, were collected during clinical interviews at age 8 years. An adaptation of the Nonword Repetition Task (NWR), in which subjects repeated recordings of nonwords, was used to assess short-term phonological memory and processing (Gathercole & Baddeley, 1996). Children also completed the Wechsler Objective Language Dimensions (WOLD) verbal comprehension task, where they answered questions about a paragraph read aloud by an examiner describing a presented picture (Weschler 1996). Z-scores were calculated for each subject on each individual measure.

Case Definitions.

Applicant aimed to capture persistently poor performers in various reading and verbal language domains as RD and LI cases in the case definitions (Table 1). Therefore, RD cases were defined as having a z-score less than or equal to −1 on at least 3 out of the 5 following tasks: single word reading at age 7 years, phoneme deletion at age 7 years, single word reading at age 9 years, nonword reading at age 9 years, and reading comprehension at age 9 years. There were 527 subjects defined as RD cases. LI cases were defined as having a z-score less than or equal to −1 on at least 2 out of the 3 following tasks: phoneme deletion at age 7 years, verbal comprehension at age 8 years, and nonword repetition at age 8 years. There were 337 subjects defined as LI cases. As phoneme awareness is important in both RD and LI, it was inclouded as part of the case definition for both RD and LI to reflect clinical presentation. There were 174 individuals affected with both RD and LI, with a male to female ratio of 1.7:1. In the further characterization of observed associations, subsets of cases were created with no comorbidity. There were 163 LI cases excluding those with comorbid RD, and 353 RD cases excluding those with comorbid LI. For all analyses, controls were defined as ALSPAC subjects of European ancestry who completed all the necessary neurobehavioral assessments but did not meet the criteria for case status.

Genotyping and Analysis.

Subjects were genotyped on Illumina HumanHap 550 bead arrays (San Diego, Calif.). Subjects were excluded if the percentage of missing genotypes was greater than 2% (n=6). To prevent possible population stratification, only subjects of European ancestry were included. In the primary analysis of RD and LI individuals, there were 174 cases and 4117 controls. There were a total of 500,527 SNPs genotyped before quality assessment and quality control. Markers were removed if Hardy-Weinberg equilibrium p≤0.0001 (n=93) or if missingness was greater than 10% (n=19). All markers had a minor allele frequency greater than 0.01. All genetic analyses were performed using logistic regression in PLINK v1.07 (Purcell et al., 2007). To correct for multiple testing, a Bonferroni corrected threshold was set of $\alpha=1.00\times 10^{-7}=0.05/500{,}000$ markers tested.

Following the initial analyses examining cases with both RD and LI, RD and LI case definitions were further examined individually (e.g., LI excluding those with comorbid RD, and RD excluding those with comorbid LI). These analyses were completed to determine whether a single disorder (RD or LI) was driving association signals in the comorbid RD and LI analysis. The associations of markers within several previously identified RD and/or LI risk genes were also examined, including those recently reported in Luciano et al., in order to present their results with these phenotypic definitions. These genes included: ABCC13, ATP2C2, BCO307918, CMIP, CNTNAP2, DAZAP1, DCDC2, DYX1 C1, FOXP2, KIAA0319, KIAA0319L, PRKCH, ROBO1, and TDP2.

Gene-based analyses were performed on each phenotype (comorbid RD and LI, as well as RD and LI individually) using the VEGAS program, similar to the Luciano et al. study (Liu et al., 2010; Luciano et al., 2013). To correct for multiple testing, a Bonferroni corrected threshold was set of $\alpha=2.84\times 10^{-6}=0.05/17{,}610$ genes tested.

PING Replication Analyses.

Replication analyses were completed in the PING study. Details on the recruitment, ascertainment, neurobehavioral, genetic, and neuroimaging methods and data acquisition in the PING study are described in detail elsewhere, but are summarized briefly below (Akshoomoff et al., 2013, Brown et al., 2012; Fjell et al., 2012; Walhovd et al., 2012). The PING study is a cross-sectional cohort of typically developing children between the ages of 3 and 20 years. Subjects were screened for history of major developmental, psychiatric, and/or neurological disorders, brain injury, or medical conditions that affect development. However, subjects were not excluded due to learning disabilities such as RD and LI. The human research protections programs and institutional review boards at the 10 institutions (Weil Cornell Medical College, University of California at Davis, University of Hawaii, Kennedy Krieger Institute, Massachusetts General Hospital, University of California at Los Angeles, University of California at San Diego, University of Massachusetts Medical School, University of Southern California, and Yale University) participating in the PING study approved all experimental and consenting procedures. For individuals under 18 years of age, parental informed consent and child assent (for those 7 to 17 years of age) were obtained. All participants age 18 years and older gave their written informed consent.

Subjects completed the validated study version of the NIH Toolbox Cognition Battery, in which two language- and reading-related tasks were completed: the Oral Reading Recognition Test and Picture Vocabulary Test (Akshoomoff et al., 2013; Weintraub et al., 2013). In the Oral Reading Recognition Test, a word or letter is presented on the computer screen and the participant is asked to read it aloud. Responses are recorded as correct or incorrect by the examiner, who views accepted pronunciations on a separate computer screen. The Picture Vocabulary Test is a measure of receptive vocabulary and administered in a computerized adaptive format. The participant is presented with an auditory recording of a word and four images on the computer screen; the task is to touch the image that most closely represents the meaning of the word.

Subjects were genotyped on the Illumina Human660W-Quad BeadChip (San Diego, Calif.), with markers used for replication analyses passing quality control filters (sample call rate >98%, SNP call rate >95%, minor allele frequency >5%). A reference panel was constructed as described elsewhere (Brown et al., 2012; Fjell et al., 2012; Walhovd et al., 2012). To assess ancestry and admixture proportions in the PING participants, a supervised clustering approach implemented in the ADMIXTURE software (Alexander et al., 2009) was used and clustered participant data into six clusters corresponding to six major continental populations: African, Central Asian, East Asian, European, Native American, and Oceanic. Implementation of ancestry and admixture proportions in the PING subjects is described in detail elsewhere (Brown et al., 2012; Fjell et al., 2012; Walhovd et al., 2012). To prevent possible population stratification, only subjects with a European genetic ancestry factor (GAF) of 1 were included in genetic analysis of behavior. These 440 individuals of European ancestry (mean age of 11.5 [standard deviation=4.8] years, 53.0% male) were analyzed using quantitative performance on the Oral Reading Recognition and Picture Vocabulary scores with PLINK v1.07, with age included as a covariate (Purcell et al., 2007). To correct for multiple testing (20 total tests=10 SNPs×2 language measures), we set statistical thresholds using the false discovery rate with $\alpha=0.05$ (Benjamini & Hochberg, 1995).

PING Imaging Analysis.

PING imaging techniques, data acquisition, and analyses are discussed in depth elsewhere and briefly below (Brown et al., 2012; Fjell et al., 2012; Walhovd et al., 2012). Across the ten sites and 12 scanners, a standardized multiple modality high-resolution structural MRI protocol was implemented, involving 3D T1- and T2-weighted volumes and a set of diffusion-weighted scans. At the University of California at San Diego, data were obtained on a GE 3T SignaHD× scanner and a 3T Discovery 750× scanner (GE Healthcare) using eight-channel phased array head coils. The protocol included a conventional three-plane localizer, a sagittal 3D inversion recovery spoiled gradient echo T1-weighted volume optimized for maximum gray/white matter contrast (echo time=3.5 ms, repetition time=8.1 ms, inversion time=640 ms, flip angle=8°, receiver bandwidth=±31.25 kHz, FOV=24 cm, frequency=256, phase=192, slice thickness=1.2 mm), and two axial 2D diffusion tensor imaging (DTI) pepolar scans (30-directions bvalue=1,000, TE=83 ms, TR=13,600 ms, frequency=96, phase=96, slice thickness=2.5 mm). Acquisition protocols with pulse sequence parameters identical or near identical to those protocols used at the University of California at San Diego were installed on scanners at the other nine sites. Data were acquired on all scanners to estimate relaxation rates and measure and correct for scanner-specific gradient coil nonlinear warping. Image files in DICOM format were processed with an automated processing stream written in MATLAB (Natick, Mass.) and C++ by the UCSD Multimodal Imaging Laboratory. T1-weighted structural images were corrected for distortions caused by gradient nonlinearities, coregistered, averaged, and rigidly resampled into alignment with an atlas brain. Image postprocessing and analysis were performed using a fully automated set of tools available in the FreeSurfer software suite (http://surfer.nmr.mgh.harvard.edu/) as well as an atlas-based method for delineating and labeling WM fiber tracts (Fischl, 2012).

Diffusion Tensor Imaging.

Diffusion-weighted images were corrected for eddy current distortion using a least squares inverse and iterative conjugate gradient descent method to solve for the 12 scaling and translation parameters describing eddy current distortions across the entire diffusion MRI scan, explicitly taking into account the orientations and amplitudes of the diffusion gradient (Zhuang et al., 2006). Head motion was corrected by registering each diffusion-weighted image to a corresponding image synthesized from a tensor fit to the data (Hagler et al., 2009). Diffusion MRI data were corrected for spatial and intensity distortions caused by B0 magnetic field in-homogeneities using the reversing gradient method (Holland et al., 2010). Distortions caused by gradient nonlinearities were corrected by applying a predefined, scanner-specific, nonlinear transformation (Jovicich et al., 2006). Diffusion-weighted images were automatically registered to T1-weighted structural images using mutual information (Wells et al., 1996) and rigidly resampled into a standard orientation relative to the T1-weighted images with isotropic 2-mm voxels. Cubic interpolation was used for all resampling steps. Conventional DTI methods were used to calculate diffusion measures (Basser et al., 1994; Pierpaoli et al., 1996). Scanning duration for the DTI sequence was 4:24 min. White matter fiber tracts were labeled using a probabilistic-atlas based segmentation method (Hagler et al., 2009). Voxels containing primarily gray matter or cerebral spinal fluid, identified using FreeSurfer's automated brain segmentation, were excluded from analysis (Fischl et al., 2002). Fiber tract volumes were calculated as the number of voxels with probability greater than 0.08, the value that provided optimal correspondence in volume between atlas-derived regions of interest and manually traced fiber tracts.

Statistical Analyses.

Imaging-genetics analyses were performed in individuals of European genetic ancestry. Scanner, age, handedness, socioeconomic status, and sex were included as covariates in all analyses (Akshoomoff et al., 2013; Brown et al., 2012; Fjell et al., 2012; Walhovd et al., 2012). 332 subjects of European genetic ancestry had completed imaging measures that passed PING quality control. Fiber tract volumes in 16 tracts of interest were tested by multiple regression analyses in R using the PING data portal (https://mmil-dataportal.ucsd.edu).

Results

SNP and Gene-Based Associations

The ten strongest GWAS associations with comorbid RD and LI in ALSPAC are presented in Table 2. The strongest associations were observed with ZNF385D (OR=1.81, $p=5.45 \times 10^{-7}$) and COL4A2 (OR=1.71, $p=7.59 \times 10^{-7}$) (Table 2). Next, RD and LI were examined individually—with no comorbid cases included—determining whether one disorder was driving these associations. The ten strongest associations for RD cases and LI cases individually are presented in Table 3 and Table 4, respectively. The strongest associations with LI were with markers in NDST4 (OR=1.83, $p=1.40 \times 10^{-7}$) (Table 3). Markers on chromosome 10 (OR=1.43, $p=5.16 \times 10^{-6}$), chromosome 8 (OR=1.70, $p=5.85 \times 10^{-6}$), and the OPA3 gene (OR=1.53, $p=6.92 \times 10^{-6}$) had the strongest associations with RD (Table 4). Markers with p<0.01 within genes previously implicated in RD and/or LI are presented in Supplemental Table 1 for each phenotype. The strongest associations with these markers were seen for KIAA0319 with comorbid RD and LI (rs16889556, p=0.0005177), FOXP2 with comorbid RD and LI (rs1530680, 0.0001702), CNTNAP2 with LI (rs6951437, p=0.0000462) and DCDC2 with LI (rs793834, 0.0002679) (Supplemental Table 1a-1c). Gene-based analyses were completed on each phenotype (comorbid RD and LI, RD individually, and LI individually), and the ten strongest gene-based associations are presented in Supplemental Table 2. None of the gene-based associations survived correction for multiple-testing; however, the strongest associations were seen with: (1) OR5H2, OR5H6, and RRAGA with comorbid RD and LI, (2) NEK2, DLEC1, and NARS with LI, and (3) MAP4, OR2L8, and CRYBA4 with RD. Markers with the strongest p-values in discovery analyses in ZNF385D, COL4A2, and NDST4 were carried forward for replication analysis in PING. We observed replication of two markers within ZNF385D and performance on the Picture Vocabulary Test (p=0.00245 and 0.004173) (Table 5). However, markers did not replicate with the Oral Reading Recognition Test (p>0.05).

Imaging-Genetics of ZNF385D

To follow-up on the replicated associations of ZNF385D, the effects of these variants on fiber tract volumes previously implicated in written and verbal language were examined. Before doing so, fiber tract volume was first determined as a predictor of performance on Oral Reading Recognition and Picture Vocabulary Tests (data not shown). Within subjects of only European genetic ancestry, ZNF385D genotypes were predictors of overall fiber tract volume and as well as fiber tract volumes in the right and left hemispheres (Table 6). ZNF385D SNPs were also predictors bilaterally within the inferior longitudinal fasiculus (ILF), inferior fronto-occipto fasiculus (IFO), and temporal superior longitudinal fasiculus (tSLF) in this subset (Table 6). To discern whether these associations between ZNF385D and fiber tract volumes reflect global brain volume differences among genotype, the relationship of ZNF385D with both total brain segmentation and total cortical volumes was examined. Associations for both measures were found with rs1679255 (p=0.00072 and 0.00027, respectively) and rs12636438 (p=0.000259 and 0.000069, respectively). The effects appeared to be additive in nature, with heterozygous individuals having intermediate phenotypes relative to those homozygous for the major allele and to those homozygous for the minor allele. In fact, when these total brain volume measures were inserted into the model as a covariate, ZNF385D associations with DTI fiber tract volumes were no longer present.

As described herein, genes were identified that contribute to the common co-occurrence of RD and LI. In the discovery analyses, associations of ZNF385D and COL4A2 were found in comorbid cases, and of NDST4 with LI. Next, associations of ZNF385D with performance were observed on a vocabulary measure, but not on an oral reading measure, in PING. Association with performance on a vocabulary measure, although not exactly recapitulating the comorbidity phenotype, does provide further evidence for the contribution of ZNF385D to language. To gain functional understanding, the effects of replicated ZNF385D markers on the volumes of language-related fiber tracts were interrogated. ZNF385D markers associated bilaterally with overall fiber tract volumes, as well as with overall brain volume.

Studies have shown that RD and LI share genetic contributors (Trzaskowski et al. 2013). However, specific genes that contribute to both RD and LI have only recently begun to be examined. These studies have only used a candidate gene approach to examine this shared genetic etiology. Such an approach has been successful in showing the shared contribution of DCDC2, KIAA0319, FOXP2, CNTNAP2, among others, to both RD and LI (Eicher & Gruen, 2013; Graham & Fisher, 2013; Newbury et al., 2009; Newbury et al., 2010; Pinel et al., 2012; Rice et al., 2009; Scerri et al., 2011). In fact, markers within KIAA0319, FOXP2, and CNTNAP2 (along with BC0307918) showed nominal association with comorbid RD and LI in the analyses (p<0.01) described herein. RD/LI risk genes also showed a tendency to associate with LI individually (DCDC2, KIAA0319, and CNTNAP2) and with RD individually (CNTNAP2 and CMIP) (p<0.01). The lack of replication for other RD/LI risk genes and differences specifically between this study and those of Scerri et al. (2011) and Luciano et al. (2013) are likely a results of different case definitions and numbers, as the instant case classifications were designed to capture as wide a range as possible of reading- and language-impaired subjects as opposed to using highly specific neurocognitive measures.

A glaring omission in the genetic investigations of RD and LI is the lack of hypothesis-free methods. These methods allow for discovery of new genes because they do not rely on pre-selected candidates. Here, the GWAS analyses indicate that ZNF385D contributes to comorbid RD and LI. This study is not the first to perform a GWAS on reading- and language-related traits. Luciano et al. (2013) recently reported a GWAS of quantitative measures of written and verbal language measures in two population-based cohorts, including ALSPAC. They found strong evidence that ABCC13, BC0307918, DAZAP1, among others contribute to performance on these measures, although the instant analyses did not provide strong evidence for them. The analytical strategies differed in two ways: (1) the use of dichotomous rather than quantitative measures to condition genetic associations and (2) examining reading and language together as opposed to individually. Past association studies of RD and LI have shown differences in results depending on whether genetic data were conditioned on dichotomous or quantitative phenotypes. For instance, KIAA0319 tends to associate more readily with quantitative measures, while DCDC2 associates more often with dichotomized variables (Paracchini et al., 2008; Powers et al., 2013; Scerri et al., 2011). The present study, which examines comorbidity, and that of Luciano et al., which examined performance on reading and language tasks individually, conditioned genetic associations on different traits, which can lead to different statistical associations. Both analytical strategies are valid and have gleaned separate, yet related insight into the genetic underpinnings of written and verbal language. They demonstrate the importance of creative and careful examination of phenotypes when examining neurocognitive and other complex traits.

Following the primary analysis of comorbid RD and LI, RD and LI were examined individually to determine whether a single disorder was driving the association signals. ZNF385D did not associate with either RD or LI individually, indicating that ZNF385D contributes to processes related to both RD and LI, as opposed to only one of these disorders. Within the PING cohort, associations of ZNF385D markers were observed with performance on the Picture Vocabulary Test and not the Oral Reading Recognition Test. Measures of receptive vocabulary (e.g. the Picture Vocabulary Test) are related to both written and verbal language tasks (Scarborough 1990, Wise et al., 2007), while performance on decoding measures (e.g. the Oral Reading Recognition Test) appear to be specific to reading. Therefore, the Picture Vocabulary Test may reflect the comorbid RD and LI phenotype used for association in ALSPAC better than the Oral Reading Recognition Test and explain the association pattern of ZNF385D in PING. In addition to ZNF385D, suggestive associations of COL4A2 with comorbid RD/LI and NDST4 with LI were observed. Neither of these associations replicated with the measures in PING, but future studies should attempt to replicate these associations, particularly due to the known involvement of COL4A2 in porencephaly and white matter lesions (Verbeek et al., 2012, Yoneda et al., 2011).

Gene-based analyses did not reveal any associations that survived correction for multiple testing. Nonetheless, there were intriguing gene associations that should be investigated in future studies. For instance, with LI, there were suggestive associations with several genes on chromosome 19—1L4I1, ATF5, NUP62, and SIGLEC11—which may correspond to the SLI2 linkage peak (Monaco, 2007; SLI Consortium, 2002), Luciano et al. (2013) found a similar accumulation of suggestively associated genes approximately 5Mb away from the genes identified herein. Additionally, MAP4, a microtubule assembly gene, was the strongest associated gene with RD. There is evidence that microtubule function plays a key role in reading development as aberrant neuronal migration is thought to contribute to the etiology of RD and other RD candidate genes are thought to interact with microtubules (e.g. DCDC2 and ACOT13) (Cheng et al., 2006). These findings can be validated in an independent cohort, using methods described herein and known methods to conclude they are involved in RD and LI.

The strongest observed associations in this study were with markers within ZNF385D. ZNF385D has previously been implicated in schizophrenia and attention deficit hyperactivity disorder (ADHD) (Poelmans et al., 2011; Xu et al., 2013). Both schizophrenia and ADHD are neurobehavioral disorders thought to have core impairments in common with RD and LI, including comprehension and semantic processing (Gilger et al., 1992; Li et al., 2009; Willcutt et al., 2005). Additionally, the observed association of ZNF385D, as described herein, on global brain volume may indicate that ZNF385D influences various neurocognitive traits through its effect on the entire brain.

There is little known regarding the function of ZNF385D, although its zinc finger domain suggests it is a transcriptional regulator. The importance of transcriptional regulation in written and verbal language is not a new concept. The most widely studied language gene, FOXP2, is a potent transcription factor that has been shown to regulate another language gene, CNTNAP2 (Vernes et al., 2007; Vernes et al., 2011). Additionally, in the DYX2 locus, two risk variants, READ1 within DCDC2 and the KIAA0319 risk haplotype, appear to have the capacity to regulate gene expression (Couto et al., 2010; Dennis et al., 2009; Meng et al., 2011) and possibly interact (Ludwig et al. 2008; Example 1; Powers et al., 2013). ZNF385D variants now join this list of putative transcriptional variants that influence written and verbal language skills The characterization of target genes of ZNF385D and of its transcriptional effects on these targets will be an important next step. Additionally, the identification of target genes may generate therapeutic candidates for treatment and remediation of RD and LI. To gain further insight into ZNF385D, imaging-genetics analyses of ZNF385D and fiber tract volumes of language-related tracts were performed. ZNF385D appears to modulate fiber tract and total brain volumes, which may subsequently affect the connectivity and functionality of brain regions important in the efficient, fluent integration of written and verbal language. Thus, identification of target genes and how the modulation of their expression during neural development yields differences in fiber tract and total brain volumes will be vital for dissecting not only the mechanism of ZNF385D, but also for the development of core language skills in children.

Characteristics of the population. First, although the overall sample size of the ALSPAC is formidable, the number of cases for each definition is relatively small. This is expected in a cross-sectional cohort of the general population as the prevalence of these disorders ranges between 5-17% (Pennington & Bishop, 2009). The ALSPAC cohort would not be expected to be enriched for RD and/or LI cases. Small sample size could have hindered the statistical power and ability to identify risk genes with small effect size. Second, the reading and language measures performed in the ALSPAC and PING studies were not identical. Phenotypes in PING were treated as a quantitative trait rather than a dichotomous variable as in ALSPAC. Therefore, attempts to replicate associations observed in the ALSPAC cohort may have been hampered as reading/language measures in PING may have captured different skills than those in ALSPAC. However, the associations observed in the PING indicate that ZNF385D plays a substantial, consistent role in overall language processes. Third, atlas-derived tract volume measures, like volumes derived from manually traced fiber tracts, are likely underestimates of true fiber volume for most tracts. However, fiber tract volumes were derived consistently for all subjects and likely reflect inter-individual differences. Nonetheless, the strength and independent replication of the associations described herein and the relationship with brain imaging phenotypes strongly implicate ZNF385D in core language processes underlying RD and LI.

In conclusion, ZNF385D was identified as a novel gene contributing to both RD and LI, as well as fiber tract and overall brain volume. The implication of another transcription factor in communication disorders underscores the importance of transcriptional regulation in neural development of language domains in the brain. Future studies should aim to further characterize the molecular functionality of ZNF385D and replicate this association, as well as our non-replicated associations—NDST4 and COL4A2—in RD, LI, and other related disorders.

REFERENCES

Akshoomoff N., et al. (2013) *J Int Neuropsychol Soc* Under Review.

Alexander D. H., et al. (2009) *Genome Res* 19(9), 1655-64.

Basser P. J., et al. (1994) *Biophys J* 66(1), 259-267.

Benjamini Y, et al. (1995) *J R Statst Soc* B 57(1): 289-300.

Boyd A., et al. (2012) *Int J Epidemiol* 42(1), 111-27.

Brown T. T., et al. (2012) *Curr Biol* 22(18), 1693-8.

Catts H. W., et al. (2005) *J Speech Lang Hear Res* 48(6), 1378-96.

Cheng Z, et al. (2006) *Biochem Biophys Res Commun* 350(4), 850-3.

Cope N., et al. (2012) *Neuroimage* 63(1), 148-56.

Couto J. M., et al. (2010) *Am J Med Genet B Neuropsychiatr Genet* 153B(2), 447-62.

Darki F., et al. (2012) *Biol Psychiatry* 72(8), 671-6.

Dennis, M. Y., et al. (2009). *PLoS Genet* 5, e1000436.

Eicher J. D. and Gruen J. R. (2013) *Mol Genet Metab*, doi: 10.1016/j.ymgme.2013.07.001.

Fischl B. (2012) FreeSurfer. *Neuroimage* 62(2), 774-81.

Fischl B., et al. (2002) *Neuron* 33(3), 41-55.

Fjell A. M., et al. (2012) *Proc Natl Acad Sci USA* 109(48), 19620-5.

Gathercole S., and Baddeley A. D. (1990) *Journal of Memory and Language* 29, 336-360.

Gathercole S. E., and Baddeley A. D. (1996) The Psychological Corportation, London.

Gilger J. W., et al. (1992) *J Am Acad Child Adolesc Psychiatry* 31(2), 343-8.

Golding J., et al. (2001) I. Study methodology. *Paediatr Perinat Epidemiol* 15(1), 74-87.

Graham S. A., and Fisher S. E. (2013) *Curr Opin Neurobiol* 23(1), 43-51.

Hagler D J, Jr., et al. (2009) *Hum Brain Mapp* 30(5): 1535-1547.

Holland D., et al. (2010) *Neuroimage* 50(1), 175-183.

Jovicich J., et al. (2006) *Neuroimage* 30(2): 436-443.

Li X., et al. (2009) *Curr Opin Psychiatry* 22(2), 131-9.

Liegeois F., et al. (2003) *Nat Neurosci* 6(11), 1230-7.

Liu J. Z., et al. (2010) *Am J Hum Genet* 87(1), 139-45.

Luciano M., et al. (2013) *Genes Brain Behav*, doi: 10.1111/gbb.12053.

Ludwig K. U., et al. (2008) *J Neural Transm* 115(11), 1587-9.

Meng H., et al. (2011) *Behav Genet* 41(1), 58-66.

Monaco A. P. (2007) *Ann Hum Genet* 71(Pt5), 660-73.

Newbury D. F., et al. (2009) *Am J Hum Genet* 85(2), 264-72.

Newbury D. F., et al. (2010) *Behav Genet* 41(1), 90-104.

Neale M. D. (1997) *Neale Analysis of Reading Ability—Revised: Manual for Schools,* NFER-Nelson.

Paracchini S., et al. (2008) *Am J Psychiat* 165(12), 1576-84.

Peterson R. L., and Pennington, B. F. (2012) *Lancet* 379, 1997-2007.

Pennington B. F., and Bishop D. V. (2009) *Annu Rev Psychol* 60, 283-306.

Pennington B F. (2006) *Cognition* 101(2), 385-413.

Pierpaoli C., et al. (1996) *Radiology* 201(3), 637-648.

Pinel P., et al. (2012) *J Neurosci* 32(3), 817-25.

Poelmans G., et al. (2011) *Am J Psychiatry* 168(4), 365-77.

Powers N. R., et al. (2013) *Am J Hum Genet* 93(1), 19-28.

Purcell S., et al. (2007) *Am J Hum Genet* 81(3), 559-575.

Rice M. L., et al. (2009) *J Neurodev Disord* 1(4), 264-82.

Rosner J., and Simon D. P. (1971) *Journal of Learning Disabilities* 4(384), 40-48.

Rust J., et al. (1993) WORD: *Wechsler Objective Reading Dimensions Manual.* Psychological Corporation, Sidcup, UK.

Scarborough H. S. (1990) *Child Dev* 61(6), 1728-43.

Scerri T. S., et al. (2012) *PLoS One* 7(11), e50312.

Scerri T. S., et al. (2011) *Biol Psychiatry* 70(3), 237-45.

Scerri T. S., and Schulte-Korne G. (2010) *Eur Child Adolesc Psychiatry* 19(3), 179-97.

Scott-Van Zeeland A. A., et al. (2010) *Sci Transl Med* 2(56), doi: 10.1126/scitranslmed.3001344.

Shaywitz S. E., and Shaywitz B. A. (2008) *Dev Psychopathol* 20(4), 1329-49.

SLI Consortium. (2002) *Am J Hum Genet* 70(2), 384-98.

Tan G. C., et al. (2010) *Neuroimage* 53(3), 1030-42.

Trzaskowski M., et al. (2013) *Behav Genet* 43(4), 267-73.

Vandermosten M., et al. (2012) *Brain* 135(Pt 3), 935-48.

Verbeek E., et al. (2012) *Eur J Hum Genet* 20(8), 844-51.

Vernes S. C., et al. (2011) *PLoS Genet* 7(7), e1002145.

Vernes S. C., et al. (2007) *Am J Hum Genet* 81(6), 1232-50.

Walhovd K. B., et al. (2012) *Proc Natl Acad Sci U S A* 109(49), 20089-94.

Wechsler D. (1996) *Wechsler objective language dimensions (WOLD).* The Psychological Corporation, London.

Wechsler D., et al. (1992) *WISC-IIIUK: Wechsler Intelligence Scale for Children.* Psychological Corporation, Sidcup, UK.

Weintraub S., et al. (2013) *Neurology* 90(11 Suppl 3), S54-64.

Wells W. M. 3rd, et al. (1996) *Med Image Anal* 1(1), 35-51.

Wilcke A., et al. (2011) *Eur J Hum Genet* 20(2), 224-9.

Willcutt E. G., et al. (2005) *Dev Neuropsychol* 27(1), 35-78.

Wise J. C., et al. (2007) *J Speech Lang Hear Res* 50(4), 1093-9.

Xu C., et al. (2013) *PLoS One* 8(1), e51674.

Yoneda Y., et al. (2012) *Am J Hum Genet* 90(1), 86-90.

Zhuang J., et al. (2006)

Tables of Example 4

TABLE 1

Reading and language measures used to define Reading Disability (RD) and Language Impairment (LI) Cases

| Reading Disability (RD) (n = 527)* | Language Impairment (LI) (n = 337)** |
| --- | --- |
| Phoneme Deletion Age 7 Years | Phoneme Deletion Age 7 Years |
| Single Word Reading Age 7 Years | Verbal Comprehension Age 8 Years |
| Single Word Reading Age 9 Years | Nonword Repetition Age 8 Years |
| Nonword Reading Age 9 Years | |
| Reading Comprehension Age 9 Years | |

*RD Cases had a z-score of less than or equal to −1 on at least 3 out of the 5 reading measures
**LI Cases had a z-score of less than or equal to −1 on at least 2 out of the 3 language measures

TABLE 2

Associations with comorbid RD and LI cases in ALSPAC (n = 174)

| Marker | Chr | Base Pair | Minor Allele | MAF Aff | MAF Unaff | Gene | Odds Ratio | P-value |
| --- | --- | --- | --- | --- | --- | --- | --- | --- |
| rs12636438 | 3 | 22038281 | G | 0.3017 | 0.1927 | ZNF385D | 1.811 | $5.45 \times 10^{-7}$ |
| rs1679255 | 3 | 22022938 | C | 0.3006 | 0.1923 | ZNF385D | 1.805 | $6.87 \times 10^{-7}$ |
| rs9521789 | 13 | 109917621 | C | 0.5201 | 0.3879 | COL4A2 | 1.71 | $7.59 \times 10^{-7}$ |
| rs1983931 | 13 | 109916103 | G | 0.5201 | 0.3896 | COL4A2 | 1.698 | $1.06 \times 10^{-6}$ |
| rs9814232 | 3 | 21948179 | A | 0.2931 | 0.1886 | ZNF385D | 1.784 | $1.30 \times 10^{-6}$ |
| rs7995158 | 13 | 109909718 | A | 0.5201 | 0.3911 | | 1.687 | $1.44 \times 10^{-6}$ |
| rs6573225 | 14 | 58354640 | C | 0.1965 | 0.1122 | | 1.935 | $1.56 \times 10^{-6}$ |
| rs4082518 | 10 | 17103032 | T | 0.3103 | 0.2049 | CUBN | 1.746 | $2.17 \times 10^{-6}$ |
| rs442555 | 14 | 58365937 | C | 0.1983 | 0.1149 | | 1.905 | $2.38 \times 10^{-6}$ |
| rs259521 | 3 | 21942154 | T | 0.2902 | 0.1885 | ZNF385D | 1.761 | $2.42 \times 10^{-6}$ |

Chr, Chromosome;

MAF Aff, Minor allele frequency in affected subjects;

MAF Unaff, Minor allele frequency in unaffected subjects

TABLE 3

Associations with LI cases in ALSPAC, excluding comorbid RD cases (n = 163)

| Marker | Chr | Base Pair | Minor Allele | MAF Aff | MAF Unaff | Gene | Odds Ratio | P-value |
|---|---|---|---|---|---|---|---|---|
| rs482700 | 4 | 116286939 | G | 0.3896 | 0.2588 | NDST4 | 1.827 | $1.40 \times 10^{-7}$ |
| rs7695228 | 4 | 116309516 | T | 0.3920 | 0.2636 | NDST4 | 1.801 | $2.94 \times 10^{-7}$ |
| rs1940309 | 4 | 116306410 | T | 0.3865 | 0.2606 | NDST4 | 1.788 | $4.14 \times 10^{-7}$ |
| rs505277 | 4 | 116248257 | T | 0.3773 | 0.2528 | NDST4 | 1.791 | $4.35 \times 10^{-7}$ |
| rs476739 | 4 | 116248997 | A | 0.3773 | 0.2529 | NDST4 | 1.79 | $4.41 \times 10^{-7}$ |
| rs867036 | 4 | 116381578 | C | 0.3957 | 0.2696 | NDST4 | 1.774 | $5.31 \times 10^{-7}$ |
| rs867035 | 4 | 116381423 | C | 0.3957 | 0.2697 | NDST4 | 1.773 | $5.45 \times 10^{-7}$ |
| rs2071674 | 4 | 2366882 | T | 0.0920 | 0.0389 | ZFYVE28 | 2.503 | $1.90 \times 10^{-6}$ |
| rs7694946 | 4 | 116413588 | C | 0.3620 | 0.2526 | NDST4 | 1.678 | $8.95 \times 10^{-6}$ |
| rs4823324 | 22 | 44616787 | C | 0.2914 | 0.4143 | ATXN10 | 0.581 | $9.30 \times 10^{-6}$ |

Chr, Chromosome;
MAF Aff, Minor allele frequency in affected subjects;
MAF Unaff, Minor allele frequency in unaffected subjects

TABLE 4

Associations with RD cases in ALSPAC, excluding comorbid LI cases (n = 353)

| Marker | Chr | Base Pair | Minor Allele | MAF Aff | MAF Unaff | Gene | Odds Ratio | P-value |
|---|---|---|---|---|---|---|---|---|
| rs180950 | 10 | 115697957 | G | 0.456 | 0.369 |  | 1.431 | $5.16 \times 10^{-6}$ |
| rs2590673 | 8 | 126037337 | G | 0.133 | 0.083 |  | 1.697 | $5.85 \times 10^{-6}$ |
| rs892100 | 19 | 50772522 | C | 0.228 | 0.162 | OPA3 | 1.526 | $6.92 \times 10^{-6}$ |
| rs1792745 | 18 | 51955991 | T | 0.187 | 0.129 |  | 1.558 | $1.22 \times 10^{-5}$ |
| rs12546767 | 8 | 126151747 | C | 0.152 | 0.099 | KIAA0196 | 1.618 | $1.32 \times 10^{-5}$ |
| rs12634033 | 3 | 146524529 | C | 0.135 | 0.087 |  | 1.646 | $1.80 \times 10^{-5}$ |
| rs892270 | 12 | 105002956 | G | 0.534 | 0.451 | NUAK1 | 1.395 | $2.16 \times 10^{-5}$ |
| rs10887149 | 10 | 124156994 | A | 0.278 | 0.357 | PLEKHA1 | 0.069 | $2.25 \times 10^{-5}$ |
| rs10041417 | 5 | 33218502 | T | 0.226 | 0.164 |  | 1.489 | $2.58 \times 10^{-5}$ |
| rs6792971 | 3 | 68468217 | C | 0.111 | 0.068 | FAM19A1 | 1.703 | $2.59 \times 10^{-5}$ |

Chr, Chromosome;
MAF Aff, Minor allele frequency in affected subjects;
MAF Unaff, Minor allele frequency in unaffected subjects

TABLE 5

Replication of associations in PING (n = 440)

| Marker | Minor Allele | MAF | Gene | Oral Reading Test | | Picture Vocabulary Test | |
|---|---|---|---|---|---|---|---|
| | | | | Beta | P-value | Beta | P-value |
| rs12636438 | G | 0.161 | ZNF385D | −0.1867 | 0.9452 | −2.88 | 0.004173* |
| rs1679255 | G | 0.292 | ZNF385D | −1.84 | 0.5016 | −3.048 | 0.002445** |
| rs9521789 | G | 0.4370 | COL4A2 | −0.3411 | 0.7332 | 0.8647 | 0.3877 |
| rs476739 | A | 0.265 | NDST4 | 0.5406 | 0.5891 | 0.5159 | 0.6062 |
| rs505277 | A | 0.280 | NDST4 | 0.5406 | 0.5891 | −0.3452 | 0.7301 |
| rs482700 | G | 0.278 | NDST4 | 0.5498 | 0.5828 | −0.05341 | 0.9574 |
| rs7695228 | A | 0.295 | NDST4 | 0.6258 | 0.5318 | 0.09991 | 0.9205 |
| rs867036 | G | 0.378 | NDST4 | 0.2605 | 0.7946 | −0.1414 | 0.8876 |
| rs867035 | G | 0.377 | NDST4 | 0.2961 | 0.7673 | −0.1565 | 0.8757 |
| rs1940309 | A | 0.281 | NDST4 | 0.6049 | 0.5456 | 0.1296 | 0.8969 |

*P-value less than FDR-adjusted statistical threshold (FDR-adjusted threshold = 0.05 × (2/19) = 0.00526
**P-value less than FDR-adjusted statistical threshold (FDR-adjusted threshold = 0.05 × (1/20) = 0.00250
MAF, Minor allele frequency in full PING sample

TABLE 6

ZNF385D Associations with DTI Fiber Tract Volumes in subjects with 100% European Genetic Ancestry (n = 332)

| Fiber Tract | rs1679255 Slope | rs1679255 P-value | rs12636438 Slope | rs12636438 P-value |
|---|---|---|---|---|
| All | −3329.9 | 0.044* | −3717.9 | 0.023* |
| Right All | −1731.4 | 0.039* | −1965 | 0.017* |
| Left All | −1616.3 | 0.055 | −1775.6 | 0.033* |
| Right ILF | −251.3 | 0.011* | −234.4 | 0.016* |
| Left ILF | −256.9 | 0.0088** | −254.6 | 0.009** |
| Right IFO | −200.8 | 0.032* | −190 | 0.041* |
| Left IFO | −221 | 0.012* | −226.3 | 0.009** |
| Right SLF | −168.1 | 0.06 | −206 | 0.02* |
| Left SLF | −199.5 | 0.022* | −212.9 | 0.013* |
| Right tSLF | −170.8 | 0.011* | −180.7 | 0.0068** |
| Left tSLF | −163.1 | 0.023* | −169.9 | 0.016* |
| Right pSLF | −153.1 | 0.079 | −182.4 | 0.034* |
| Left pSLF | −112.2 | 0.18 | −125.3 | 0.131 |
| Right SIFC | −148.8 | 0.052 | −165.6 | 0.029* |
| Left SIFC | −34.54 | 0.66 | −54.3 | 0.48 |
| CC | −977.1 | 0.15 | −1181.6 | 0.081 |

*p ≤ 0.05
**p ≤ 0.01
Abbreviations:
All (All Fiber Tracts),
ILF (Inferior Longitudinal Fasiculus),
IFO (Inferior Fronto-occipital Fasiculus),
SLF (Superior Longitudinal Fasiculus),
tSLF (Temporal Superior Longitudinal Fasiculus),
pSLF (Parietal Superior Longitudinal Fasiculus),
SIFC (Striatal Inferior Frontal Cortex),
CC (Corpus Callosum)

Supplement Tables

Supplemental Table 1: Associations of markers within genes previously implicated in RD and/or LI with (a) Comorbid RD and LI, (b) LI individually, and (c) RD individually.

| Marker | Gene | Chr. | Base Pair | P-value |
|---|---|---|---|---|
| a) Comorbid RD and LI | | | | |
| rs16889556 | KIAA0319 | 6 | 24749584 | 0.0005177 |
| rs1047782 | TDP2 | 6 | 24758710 | 0.006515 |
| rs1530680 | FOXP2 | 7 | 114194632 | 0.0001702 |
| rs12667130 | FOXP2 | 7 | 114213035 | 0.003033 |
| rs6965855 | CNTNAP2 | 7 | 145348483 | 0.006804 |
| rs985080 | CNTNAP2 | 7 | 145359118 | 0.006157 |
| rs4726782 | CNTNAP2 | 7 | 145425012 | 0.005341 |
| rs1718101 | CNTNAP2 | 7 | 145753721 | 0.0008707 |
| rs10487689 | CNTNAP2 | 7 | 146835482 | 0.008787 |
| rs1918296 | CNTNAP2 | 7 | 147655135 | 0.00616 |
| rs737533 | BC0307918 | 10 | 3353137 | 0.001008 |
| b) LI | | | | |
| rs793845 | DCDC2 | 6 | 24296970 | 0.005511 |
| rs2799373 | DCDC2 | 6 | 24303738 | 0.0009664 |
| rs793862 | DCDC2 | 6 | 24315179 | 0.002443 |
| rs793834 | DCDC2 | 6 | 24342912 | 0.0002679 |
| rs2792682 | DCDC2 | 6 | 24380363 | 0.006634 |
| rs807704 | DCDC2 | 6 | 24408825 | 0.001988 |
| rs707864 | DCDC2 | 6 | 24413827 | 0.001266 |
| rs12193738 | KIAA0319 | 6 | 24676372 | 0.00974 |
| rs2817198 | KIAA0319 | | 24683073 | 0.00559 |
| rs10456309 | KIAA0319 | 6 | 24697541 | 0.002258 |
| rs985080 | CNTNAP2 | 7 | 145359118 | 0.006735 |
| rs1554690 | CNTNAP2 | 7 | 145377266 | 0.006486 |
| rs2533096 | CNTNAP2 | 7 | 146037312 | 0.004782 |
| rs6951437 | CNTNAP2 | 7 | 146037340 | 0.0000462 |
| rs344470 | CNTNAP2 | 7 | 146044430 | 0.001697 |
| rs344468 | CNTNAP2 | 7 | 146050259 | 0.003965 |
| c) RD | | | | |
| rs4725745 | CNTNAP2 | 7 | 147032172 | 0.002407 |
| rs12444778 | CMIP | 16 | 80330728 | 0.003148 |
| rs1444186 | CMIP | 16 | 80330745 | 0.00482 |

Supplemental Table 2: Gene-based analyses of comorbid RD and LI, LI individually, and RD individually. The top ten gene-based associations for each are shown.

| Gene | Ch | Start Position | Stop Position | No. SNPS in Gene | p-value |
|---|---|---|---|---|---|
| RD and LI | | | | | |
| OR5H2 | 3 | 99484421 | 99485366 | 16 | 0.000072 |
| OR5H6 | 3 | 99465818 | 99466796 | 19 | 0.000127 |
| RRAGA | 9 | 19039371 | 19041021 | 30 | 0.000276 |
| OR6B3 | 2 | 240633166 | 240634162 | 36 | 0.000294 |
| UMOD | 16 | 20251873 | 20271538 | 29 | 0.000307 |
| A26C1A | 2 | 131692393 | 131738886 | 1 | 0.000389 |
| FAM29A | 9 | 19043140 | 19092902 | 44 | 0.000406 |
| CHRNA1 | 2 | 175320568 | 175337446 | 23 | 0.000420 |
| IFIT5 | 10 | 91164418 | 91170733 | 27 | 0.000475 |
| LOC643905 | 2 | 240629902 | 240631072 | 39 | 0.000562 |
| LI | | | | | |
| NEK2 | 1 | 209902744 | 209915590 | 28 | 0.000117 |
| DLEC1 | 3 | 38055699 | 38139232 | 20 | 0.000171 |
| NARS | 18 | 53418891 | 53440175 | 36 | 0.000203 |
| IL4I1 | 19 | 55084722 | 55124574 | 22 | 0.000305 |
| PKD2 | 4 | 89147843 | 89217953 | 34 | 0.000313 |
| ATF5 | 19 | 55123785 | 55129004 | 18 | 0.000344 |
| NUP62 | 19 | 55101893 | 55124598 | 19 | 0.000402 |
| SIGLEC11 | 19 | 55144061 | 551556241 | 49 | 0.000578 |
| ACAN | 15 | 87147677 | 87219589 | 43 | 0.000633 |
| PGD | 1 | 10381671 | 10402788 | 12 | 0.000668 |
| RD | | | | | |
| MAP4 | 3 | 47867188 | 48105715 | 18 | 0.000085 |
| OR2L8 | 1 | 246178782 | 246179721 | 19 | 0.000139 |
| CRYBA4 | 22 | 25347927 | 25356636 | 40 | 0.000219 |
| OR2T8 | 1 | 246150942 | 246151881 | 24 | 0.000225 |
| KIAA1622 | 14 | 93710401 | 93815825 | 42 | 0.000255 |
| OR2AK2 | 1 | 246195256 | 246196264 | 15 | 0.000315 |
| DHX30 | 3 | 47819654 | 47866687 | 11 | 0.000316 |
| GEMIN6 | 2 | 38858830 | 38862610 | 8 | 0.000351 |
| C20orf10 | 20 | 43435933 | 43440371 | 23 | 0.000450 |
| PPIF | 10 | 80777225 | 38862610 | 22 | 0.000493 |

What is claimed is:

1. A method of detecting markers in a variant doublecortin domain containing 2 (DCDC2) gene in the DYX2 locus on chromosome 6p in a sample obtained from a human, wherein the sample comprises nucleic acids, the method comprising:
   (1) combining the sample with separate polynucleotides, each of which hybridizes under highly stringent conditions to
      (a) one allele of the CGCGAG haplotype in the DCDC2 gene at positions rs33914824, rs807694, rs707864, rs10456301, rs16889066, and rs9379651, respectively; or
      (b) one allele of the GACGAG haplotype in the DCD2 gene at positions rs33914824, rs807694, rs707864, rs10456301, rs16889066, and rs9379651, respectively; or
      (c) one allele of the CGCGAG haplotype in the DCDC2 gene at positions rs33914824, rs807694, rs707864, rs10456301, rs16889066, and rs9379651, respectively and to one allele of the GACGAG haplotype in the DCDC2 gene at positions rs33914824, rs807694, rs707864, rs10456301, rs16889066, and rs9379651, respectively,
   maintaining the combination under highly stringent conditions; and
   (2) detecting whether hybridization occurs in (1), wherein when hybridization of the polynucleotides of (a) occurs, the sample contains the CGCGAG haplotype of the DCDC2 gene; when hybridization of the polynucleotides of (b) occurs, the DCDC2 gene in the sample contains the GACGAG haplotype; and when hybridization of the polynucleotides of (c) occurs, the DCDC2 genes in the sample comprise one of each of the CGCGAG and GACGAG haplotypes.

2. The method of claim 1, wherein in (1) the sample is contacted with an array comprising the separate polynucleotides, each of which hybridizes under highly stringent conditions to (a) or (b) or (c).

3. The method of claim 1, wherein the sample is blood, cells or tissue.

4. The method of claim 1, wherein if the sample comprises any one of (a)-(c), the method further comprises monitoring the individual from whom the nucleic acid sample was obtained to assess whether development of a learning disability occurs and if development occurs, treating the individual for the learning disability, wherein treating comprises providing interventions, including services and materials, including but not limited to: using special teaching techniques; making classroom modifications; using books on tape; using word-processing programs with spell-check features; helping the individual learn through multi-sensory experiences; teaching coping tools; and providing services to strengthen the individual's ability to recognize and pronounce words.

5. The method of claim 1, further comprising in (1):
   combining the sample with
      (d) a polynucleotide that hybridizes to allele 5 of DCDC2 gene (SEQ ID NO:35) in the DYX2 locus; and
      (e) a polynucleotide that hybridizes to allele 6 of DCDC2 gene (SEQ ID NO:36) in the DYX2 locus; and
   further comprising in (2), detecting whether hybridization occurs in (1), wherein when hybridization of the polynucleotide of (d) occurs, the sample contains allele 5 of the DCDC2 gene and when hybridization of the polynucleotide of (e) occurs, the sample contains allele 6 of the DCDC2 gene.

6. The method of claim 5, wherein the sample is blood, cells or tissue.

7. The method of claim 5, wherein in (1) the sample is combined with an array comprising the separate polynucleotides, each of which hybridizes under highly stringent conditions to at least one of (a), (b), (c), (d), and (e).

8. The method of claim 5, wherein if the sample comprises any one of (a)-(e), the method further comprises monitoring the individual from whom the nucleic acid sample was obtained to assess whether development of a learning disability occurs and if development occurs, treating the individual for the learning disability, wherein treating comprises providing interventions, including services and materials, including but not limited to: using special teaching techniques; making classroom modifications; using books on tape; using word-processing programs with spell-check features; helping the individual learn through multisensory experiences; teaching coping tools; and providing services to strengthen the individual's ability to recognize and pronounce words.

9. A method comprising:
(1) performing hybridization-based methods, nucleic acid sequencing techniques, or both on a sample obtained from a human, wherein the sample comprises nucleic acids; and
(2) detecting:
(a) the CGCGAG haplotype in the DCDC2 gene of the human with positions rs33914824, rs807694, rs707864, rs10456301, rs16889066, and rs9379651, respectively; or
(b) the GACGAG haplotype in the DCDC2 gene of the human with positions rs33914824, rs807694, rs707864, rs10456301, rs16889066, and rs9379651, respectively; or
(c) each of the CGCGAG haplotype and the GACGAG haplotype in the DCDC2 genes of the human with positions rs33914824, rs807694, rs707864, rs10456301, rs16889066, and rs9379651, respectively.

10. The method of claim 9, wherein the method comprises: combining the sample with:
(i) separate polynucleotides, each of which hybridizes to one allele of the CGCGAG haplotype of (a); or
(ii) separate polynucleotides, each of which hybridizes to one allele of the GACGAG haplotype of (b); or
(iii) separate polynucleotides, each of which hybridizes to one allele of the CGCGAG haplotype of (a) and separate polynucleotides, each of which hybridizes to one allele of the GACGAG haplotype of (b); and
detecting whether hybridization of the polynucleotides of (i), (ii), or (iii) occurs, wherein the occurrence of hybridization of each of (i), (ii), or (iii) indicates the DCDC2 gene in the sample contains the CGCGAG haplotype, the DCDC2 gene in the sample contains the GACGAG haplotype, and the DCDC2 genes in the sample comprise one of each of the CGCGAG and GACGAG haplotypes, respectively.

11. The method of claim 9, wherein the sample is blood, cells or tissue.

12. The method of claim 10, wherein the sample is combined with an array comprising the separate polynucleotides of (i); or separate polynucleotides of (ii); or separate polynucleotides of (iii).

13. The method of claim 9, further comprising detecting in the sample:
(d) allele 5 of DCDC2 gene (SEQ ID NO:35) in the DYX2 locus; and
(e) allele 6 of DCDC2 gene (SEQ ID NO:36) in the DYX2 locus.

14. The method of claim 13, comprising combining the sample with:
(i) separate polynucleotides, each of which hybridizes to one allele of the CGCGAG haplotype of (a); or
(ii) separate polynucleotides, each of which hybridizes to one allele of the GACGAG haplotype of (b); or
(iii) separate polynucleotides, each of which hybridizes to one allele of the CGCGAG haplotype of (a) and separate polynucleotides, each of which hybridizes to one allele of the GACGAG haplotype of (b); and
combining the sample with:
(iv) a polynucleotide that hybridizes with all or a portion of allele 5 of DCDC2 gene (SEQ ID NO:35) in the DYX2 locus; and
(v) a polynucleotide that hybridizes with all or a portion of allele 6 of DCDC2 gene (SEQ ID NO:36) in the DYX2 locus;
and
determining whether hybridization of the polynucleotides of (i)-(v) occurs, wherein the occurrence of hybridization of each of (i)-(v) indicates the presence of the CGCGAG haplotype, the GACGAG haplotype, the CGCGAG and GACGAG haplotypes, allele 5 of the DCDC2 gene, and allele 6 of the DCDC2 gene, respectively.

15. The method of claim 13, wherein the sample is blood, cells or tissue.

16. A method of assaying a sample obtained from a human for a variant gene in the DYX2 locus, comprising:
obtaining a sample comprising nucleic acid from the human, and using genomic sequencing to detect:
(a) the CGCGAG haplotype in the DCDC2 gene of the human with positions rs33914824, rs807694, rs707864, rs10456301, rs16889066, and rs9379651, respectively; or
(b) the GACGAG haplotype in the DCDC2 gene of the human with positions rs33914824, rs807694, rs707864, rs10456301, rs16889066, and rs9379651, respectively; or
(c) each of the CGCGAG haplotype and the GACGAG haplotype in the DCDC2 genes of the human with positions rs33914824, rs807694, rs707864, rs10456301, rs16889066, and rs9379651, respectively;
wherein detection of (a) or (b) or (c) indicates that the sample comprises a variant DCDC2 gene in the DYX2 locus.

17. The method of claim 16, further comprising:
using genomic sequencing to detect: whether the sample comprises:
(d) allele 5 of DCDC2 gene in the DYX2 locus; or
(e) allele 6 of DCDC2 gene in the DYX2 locus,
wherein detection of either (d) or (e), indicates that the sample comprises a variant DCDC2 gene in the DYX2 locus.

18. The method of claim 16, wherein the sample is blood, cells or tissue.

19. The method of claim 17, wherein the sample is blood, cells or tissue.

20. The method of claim 4, wherein the classroom modifications comprise providing extra time to complete tasks or taped tests to permit the individual to hear, rather than read, the tests.

21. The method of claim 8, wherein the classroom modifications comprise providing extra time to complete tasks or taped tests to permit the individual to hear, rather than read, the tests.

* * * * *